United States Patent
Verpoort

(10) Patent No.: US 10,160,828 B2
(45) Date of Patent: Dec. 25, 2018

(54) GROUP 8 TRANSITION METAL CATALYSTS AND METHOD FOR MAKING SAME AND PROCESS FOR USE OF SAME IN METATHESIS REACTION

(71) Applicant: GUANG MING INNOVATION COMPANY (WUHAN), Wuhan, Hubei (CN)

(72) Inventor: Francis W. C. Verpoort, Hubei (CN)

(73) Assignee: GUANG MING INNOVATION COMPANY (WUHAN), Wuhan, Hubei (CN)

( * ) Notice: Subject to any disclaimer, the term of this patent is extended or adjusted under 35 U.S.C. 154(b) by 0 days.

(21) Appl. No.: 15/323,578

(22) PCT Filed: Jul. 3, 2014

(86) PCT No.: PCT/CN2014/081605
§ 371 (c)(1),
(2) Date: Jan. 3, 2017

(87) PCT Pub. No.: WO2016/000242
PCT Pub. Date: Jan. 7, 2016

(65) Prior Publication Data
US 2017/0145152 A1    May 25, 2017

(51) Int. Cl.
| | |
|---|---|
| *B01J 31/28* | (2006.01) |
| *C08F 4/80* | (2006.01) |
| *C08G 61/08* | (2006.01) |
| *B01J 31/24* | (2006.01) |
| *C07F 15/00* | (2006.01) |
| *B01J 31/22* | (2006.01) |
| *C07C 2/86* | (2006.01) |
| *C08G 61/02* | (2006.01) |
| *B01J 31/18* | (2006.01) |
| *C07C 67/333* | (2006.01) |
| *C07C 67/475* | (2006.01) |
| *C07C 1/213* | (2006.01) |
| *C07C 6/04* | (2006.01) |

(52) U.S. Cl.
CPC ............ *C08G 61/08* (2013.01); *B01J 31/181* (2013.01); *B01J 31/1805* (2013.01); *B01J 31/2226* (2013.01); *B01J 31/2265* (2013.01); *B01J 31/2278* (2013.01); *B01J 31/24* (2013.01); *B01J 31/2404* (2013.01); *C07C 1/213* (2013.01); *C07C 2/862* (2013.01); *C07C 6/04* (2013.01); *C07C 67/333* (2013.01); *C07C 67/475* (2013.01); *C07F 15/0046* (2013.01); *C08G 61/02* (2013.01); *B01J 2231/12* (2013.01); *B01J 2231/44* (2013.01); *B01J 2231/54* (2013.01); *B01J 2531/80* (2013.01); *B01J 2531/821* (2013.01); *B01J 2531/825* (2013.01); *C07C 2531/22* (2013.01); *C07C 2531/24* (2013.01); *C07C 2601/10* (2017.05); *C08G 2261/11* (2013.01); *C08G 2261/3323* (2013.01); *C08G 2261/3325* (2013.01); *C08G 2261/418* (2013.01)

(58) Field of Classification Search
CPC .. B01J 31/28; B01J 2231/54; B01J 2531/821; C08F 4/80
See application file for complete search history.

(56) References Cited

U.S. PATENT DOCUMENTS

| | | | |
|---|---|---|---|
| 4,717,785 A | 1/1988 | Paxson | |
| 8,507,398 B2 * | 8/2013 | Meca | B01J 31/2265 502/152 |
| 2015/0367338 A1 * | 12/2015 | Verpoort | C08F 4/72 526/171 |

FOREIGN PATENT DOCUMENTS

| | | | | |
|---|---|---|---|---|
| CN | 101371991 A | 2/2009 | | |
| WO | 03044060 A3 | 2/2004 | | |
| WO | 2004035596 A1 | 4/2004 | | |
| WO | WO 2011/100022 A2 * | 8/2011 | | B01J 31/22 |
| WO | 2011117571 A1 | 9/2011 | | |
| WO | WO 2013/029079 A1 * | 3/2013 | | C07D 215/30 |

OTHER PUBLICATIONS

International Search Report (ISR) issued by the State Intellectual Property Office of the Peoples Republic of China dated Apr. 3, 2015 for PCT/CN2014/081605, China.

* cited by examiner

*Primary Examiner* — Rip A Lee
(74) *Attorney, Agent, or Firm* — Tim Tingkang Xia, Esq.; Locke Lord LLP

(57) ABSTRACT

Metal catalyst compounds are disclosed. The catalyst compound are represented by the formula (I-II and VII): wherein M is a Group 8 metal; X is an anionic ligand; L is a neutral two electron donor ligand; K 2 (A-E) is a ditopic or multitopic ligand. Also disclosed is an easy applicable catalyst synthesis and the application in different olefin metathesis processes, e.g. Reaction Injection Molding (RIM), rotational molding, vacuum infusion, vacuum forming, process for conversion of fatty acids and fatty acid esters or mixtures thereof, in -olefins, dicarboxylic acids or dicarboxylic esters, etc.

42 Claims, 3 Drawing Sheets

GROUP 8 TRANSITION METAL CATALYSTS AND METHOD FOR MAKING SAME AND PROCESS FOR USE OF SAME IN METATHESIS REACTION

FIELD OF THE INVENTION

This invention relates to Group 8 transition metal catalysts and method for making same and process for use of same in metathesis reaction.

BACKGROUND OF THE INVENTION

Olefin metathesis is a catalytic process including, as a key step, a reaction between a first olefin and a first transition metal alkylidene complex, thus producing an unstable intermediate metallocyclobutane ring which then undergoes transformation into a second olefin and a second transition metal alkylidene complex according to equation (1) hereunder. Reactions of this kind are reversible and in competition with one another, so the overall result heavily depends on their respective rates and, when formation of volatile or insoluble products occurs, displacement of equilibrium.

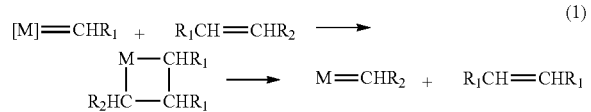

Metathesis reactions are extensively applied in the field of chemical reactions, e.g. Ring closing metathesis (RCM), Cross metathesis (CM), Ring opening metathesis (ROM), Ring opening metathesis polymerization (ROMP), acyclic diene metathesis (ADMET), self-metathesis, conversion of olefins with alkynes (enyne metathesis), polymerization of alkynes, and so on.

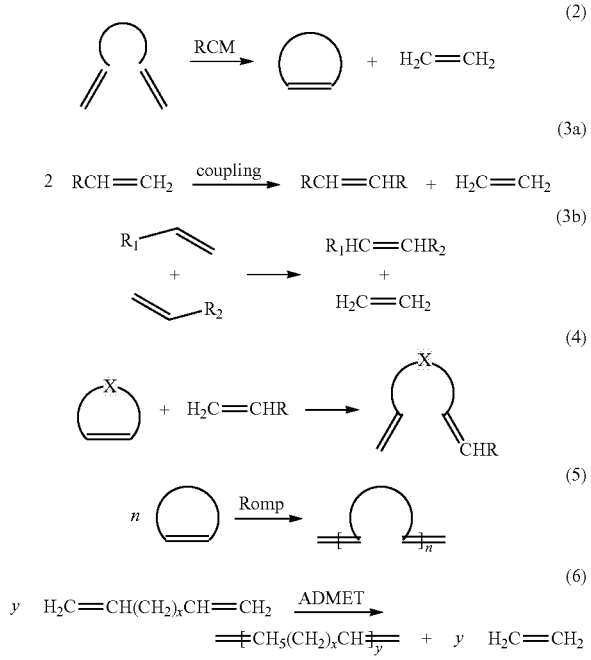

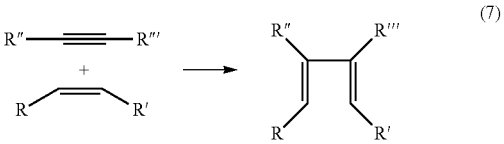

Typical applications of olefin metathesis but not limited are Reaction Injection Molding (RIM), filament winding, pultrusion of dicyclopentadiene (DCPD), which is an example of the ring opening metathesis polymerization. Industrial application in DCPD polymerization requires latent catalysts, which can allow for longer handling of a monomer-catalyst mixture before the polymerization starts. Other examples of ring opening metathesis polymerization are ROMP of norbornene and its derivatives, copolymerization of different cyclic olefins. Ethenolysis, a chemical process in which internal olefins are degraded using ethylene as the reagent, is an example of cross metathesis; CM of ethene with 2-butene; depolymerization of unsaturated polymers and so fort.

Although homo-coupling (equation 3a) is of high interest, the same is true for cross-coupling between two different terminal olefins (equation 3b). Coupling reactions involving dienes lead to linear and cyclic dimers, oligomers, and, ultimately, linear or cyclic polymers (equation 6). In general, the latter reaction is favoured in highly concentrated solutions or in bulk, while cyclisation is favoured at low concentrations. When intra-molecular coupling of a diene occurs so as to produce a cyclic alkene, the process is called ring-closing metathesis (equation 2). Cyclic olefins can be opened and oligomerised or polymerised (ring opening metathesis polymerisation shown in equation 5). When the alkylidene catalyst reacts more rapidly with the cyclic olefin (e.g. a norbornene or a cyclobutene) than with a carbon-carbon double bond in the growing polymer chain, then a "living ring opening metathesis polymerisation" may result, i.e. there is little termination during or after the polymerization reaction. Strained rings may be opened using an alkylidene catalyst with a second alkene following the mechanisms of the Cross Metathesis. The driving force is the relief of ring strain. As the products contain terminal vinyl groups, further reactions of the Cross Metathesis variety may occur. Therefore, the reaction conditions (time, concentrations, . . . ) must be optimized to favour the desired product (equation 4). The enyne metathesis is a metalcarbene-catalysed bond reorganization reaction between alkynes and alkenes to produce 1,3-dienes. The intermolecular process is called Cross-Enyne Metathesis (7), whereas intramolecular reactions are referred as Ring-Closing Enyne Metathesis (RCEYM).

The cross-metathesis of two reactant olefins, where each reactant olefin comprises at least one unsaturation site, to produce new olefins, which are different from the reactant olefins, is of significant commercial importance. One or more catalytic metals, usually one or more transition metals, usually catalyse the cross-metathesis reaction.

One such commercially significant application is the cross-metathesis of ethylene and internal olefins to produce alpha-olefins, which is generally referred to as ethenolysis. More specific, the cross-metathesis of ethylene and an internal olefin to produce linear α-olefins is of particular commercial importance. Linear α-olefins are useful as monomers or co-monomers in certain (co)polymers poly α-olefins and/or as intermediates in the production of epoxides, amines, oxo alcohols, synthetic lubricants, synthetic fatty acids and alkylated aromatics. Olefins Conversion Technology™, based upon the Phillips Triolefin Process, is an example of an ethenolysis reaction converting ethylene and 2-butene into propylene. These processes apply heterogeneous catalysts based on tungsten and rheniumoxides, which have not proven effective for internal olefins containing functional groups such as cis-methyl oleate, a fatty acid methyl ester.

1-Decene is a co-product typically produced in the cross-metathesis of ethylene and methyl oleate. Alkyl oleates are fatty acid esters that can be major components in biodiesel produced by the transesterification of alcohol and vegetable oils. Vegetable oils containing at least one site of unsaturation include canola, soybean, palm, peanut, mustard, sunflower, tung, tall, perilla, grapeseed, rapeseed, linseed, safflower, pumpkin, corn and many other oils extracted from plant seeds. Alkyl erucates similarly are fatty acid esters that can be major components in biodiesel. Useful biodiesel compositions are those, which typically have high concentrations of oleate and erucate esters. These fatty acid esters preferably have one site of unsaturation such that cross-metathesis with ethylene yields 1-decene as a co-product.

Vegetables oils used in food preparation (fritting of meat, vegetables, . . . ) can be recuperated and after purification, be converted applying e.g. ethenolysis into useful products applicable in biodiesel.

Biodiesel is a fuel prepared from renewable sources, such as plant oils or animal fats. To produce biodiesel, triacylglycerides, the major compound in plant oils and animal fats, are converted to fatty acid alkyl esters (i.e., biodiesel) and glycerol via reaction with an alcohol in the presence of a base, acid, or enzyme catalyst. Biodiesel fuel can be used in diesel engines, either alone or in a blend with petroleum-based diesel, or can be further modified to produce other chemical products.

Several metal-carbene complexes are known for olefin metathesis however the difference between those structures can be found in the carbene part. Patents WO-A-96/04289 and WO-A-97/06185 are examples of metathesis catalysts having the general structure

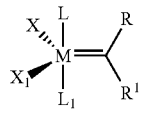

Where:

M is Os or Ru, R and R$^1$ organic parts from the carbene fragment which have a great structural variability, X and X$_1$ are anionic ligands and L and L$_1$ represents neutral electron donors. "Anionic ligands" are, according the literature in the field of olefin metathesis catalysts, ligands which are negative charged and thus bearing a full electron shell when they are removed from the metal center A well-known example of this class of compounds is the Grubbs 1$^{st}$ generation catalysts (G1)

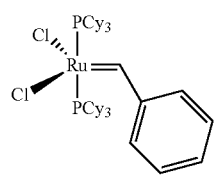

Another well-known example of this class of compounds is the Grubbs' 2$^{nd}$ generation catalyst which is described in WO-A-0071554 and the hexa-coordinated "Grubbs 3$^{rd}$ generation catalyst described in WO-A03/011455.

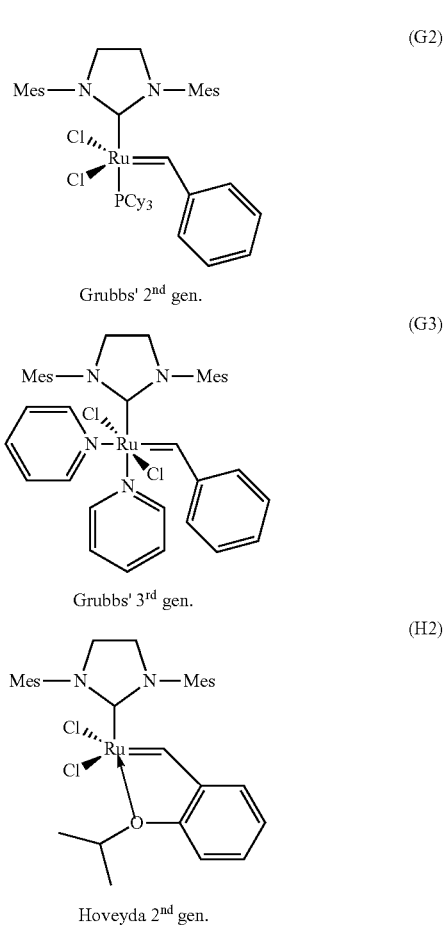

There are still some other well-known catalysts described in literature which are very useful in the area of olefin metathesis, and which serve as background information for this application.

Furthermore, other catalysts are known where both carbon atoms of the carbene fragment are bridged; a few of these representatives are given:

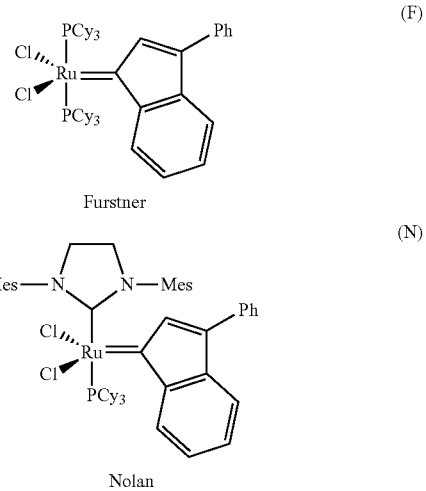

The bridged carbene fragment was firstly synthesized by Hill et al. (K. J. Harlow, A. F. Hill, J. D. E. T. Wilton-Ety, J. Chem. Soc. Dalton Trans. 1999, 285-291), however the structure was wrongly interpreted. Fürstner et al. corrected this misinterpretation (J. Org. Chem. 1999, 64, 8275-8280)

and a full characterization was described. It followed that reorganization takes place whereby the carbon atoms of the carbene fragment are bridged and generating in this specific case a "3-phenyl-indenylidene carbene" (Chem. Eur. J. 2001, 7, No 22, 4811-4820). Analogues of this catalyst bearing one NHC-ligand and one phosphine ligand where described by Nolan in WO-A-00/15339. These types of compounds are not only catalysts for the olefin metathesis; they also can be used as starting product to produce other ruthenium-carbene compounds via cross metathesis (WO-A-2004/112951).

Furthermore, in US-A-2003/0100776 on page 8, paragraph [0087] are catalysts described where the carbon atoms of the carbene part are bridged and whereby the newly formed cyclic group can be aliphatic or aromatic and can bear substituents or hetero atoms. Additionally, it is said that the generated ring structure is constructed of 4 to 12 and preferable 5 to 8 atoms contains. However, no explicit ring structures or examples are described or given.

For some processes it is desirable that catalyst initiation be controllable. Much less work has focused on decreasing the initiation rate of ruthenium-based catalysts. In these cases, the use of a trigger such as light activation (e.g. photoirradiation), chemical activation (e.g. acid addition), temperature activation (e.g. heating of the sample) or mechanical activation (e.g. ultrason) can help to control initiation. Efficient ring-opening metathesis polymerization (ROMP) reactions require adequate mixing of monomer and catalyst before polymerization occurs. For these applications, catalysts that initiate polymerization at a high rate only upon activation are desirable. However, both Grubbs $2^{nd}$ gen and Hoveyda $2^{nd}$ gen. are competent metathesis catalysts at or below room temperature, so alone are not suited for applications where catalyst latency is beneficial (Org. Lett. 1999, 1, 953-956; J. Am. Chem. Soc. 2000, 122, 8168-8179; Tetrahedron Lett. 2000, 41, 9973-9976).

Experimental studies have shown that, for the majority of ruthenium catalysts, dissociation of a donor ligand provides entry to the catalytic cycle. Several design strategies for slowing ligand dissociation can be envisioned. An important consideration is that the method used to slow initiation should not disrupt the catalyst activity. The addition of excess phosphine to the reaction can serve to slow initiation as shown in case I (Scheme 1)(J. Am. Chem. Soc. 1997, 119, 3887-3897). Unfortunately the addition of phosphine commonly results in propagation rates also being reduced.

Scheme 1: Strategies to control catalyst initiation.

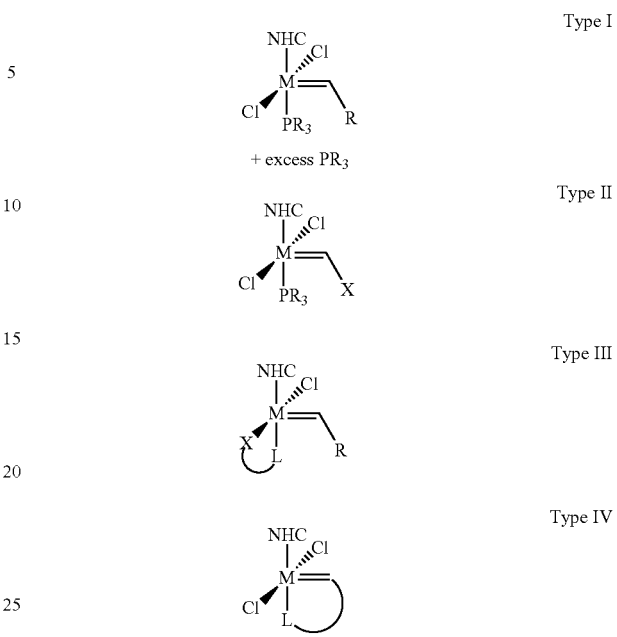

Another strategy to slow catalyst initiation is to replace the Schrock-type ruthenium carbene with a Fischer carbene (Type II, Scheme 1). This approach has been used to generate several latent metathesis catalysts with Fischer carbenes featuring oxygen, sulphur, and nitrogen substitution. (Organometallics 2002, 21, 2153-2164; J. Organomet. Chem. 2000, 606, 65-74). In some cases, the decrease in activity with these systems is so great that they are considered metathesis-inactive. In fact, addition of ethyl vinyl ether to form a Fischer carbene complex is a standard method of quenching ROMP reactions.

Van der Schaaf and co-workers followed another approach (type IV, scheme 1) to develop the temperature activated, slow initiating olefin metathesis catalyst ($PR_3$) $(Cl)_2Ru(CH(CH_2)_2$—C,N-2-$C_5H_4N$) (1 in Scheme 2) in which initiation temperatures were tuned by changing the substitution pattern of the pyridine ring (J. Organomet. Chem. 2000, 606, 65-74). Unfortunately, activities of the reported complexes were undesirably low; restricted to 12000 equiv DCPD. Later, Ung reported on analogous tunable catalytic systems obtained by partially isomerizing trans-(SIMes)($Cl)_2Ru(CH(CH_2)_2$—C,N-2-$C_5H_4N$) (2 in scheme 2) into the cis analogue (Organometallics 2004, 23, 5399-5401). However, none of these catalysts allowed for storage in DCPD monomer for long time as the ROMP of DCPD is completed in 25 minutes after catalyst introduction.

Scheme 2: Examples of type IV systems to control the initiation.

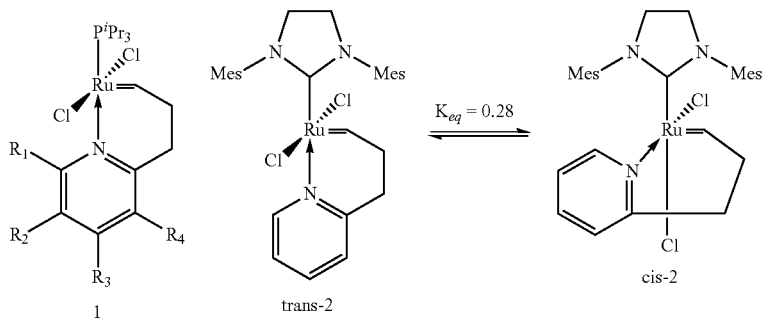

In another methodology towards rationally designed thermally stable olefin metathesis catalyst for DCPD polymerization, efforts were directed towards the development of an O,N-bidentate Schiff base ligated Ru-carbene catalysts elaborated by Grubbs (U.S. Pat. No. 5,977,393; Scheme 3, 4 wherein L=PR$_3$) and Verpoort (WO 03/062253; Scheme 3, 4 wherein L=SIMes and 5 wherein L=PR$_3$, SIMes). It was shown that such complexes are extremely inactive at room temperature towards the polymerization of low-strain, cyclic olefins, allow for storage in DCPD for months and can be thermally activated to yield increased activity for the bulk-polymerization of DCPD, but from industrial point of view, catalysts of which their performance is easy tunable by a simple straightforward modification are not described (EP1468004; J. Mol. Cat. A: Chem. 2006, 260, 221-226).

Scheme 3: Examples of type III systems to control the initiation

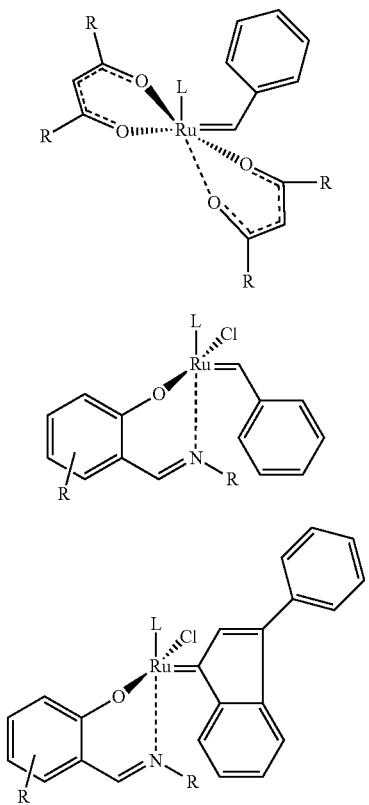

Recently a series of latent olefin metathesis catalysts bearing bidentate K$^2$—(O,O) ligands were synthesized (Scheme 3, 3). Complex 3, proved to be inactive for the solvent-free polymerization of DCPD. It was furthermore illustrated that complex 3 (Scheme 3, L=PCy$_3$, SIMes) is readily activated upon irradiation of a catalyst/monomer mixture containing a photoacid generator and was found applicable in ROMP of DCPD (WO 99/22865). Nevertheless irradiation of a solution of DCPD and 3 (L=SIMes) in a minimal amount of CH$_2$Cl$_2$ resulted in complete gelation within 1 h but solidified and cross-linked monomer was not obtained.

This indicates low catalyst activity and the operation on a low amount of the active species. Summarizing, the latent catalysts are of prominent importance for Ring-Opening Metathesis Polymerizations of low-strained cyclic olefins, as they allow for mixing of monomer and catalyst without concomitant gelation or microencapsulation of the precatalyst.

All the above-described catalysts bearing an indenylidene carbene part are based on a non-chelating phenyl-indenylidene structure without any substituents or functional groups. Catalysts with a chelating phenyl-indenylidene structure have been described in PCT/US2010/059703 (WO 2011/100022 A2) an indenylidene based catalyst is described whereby one phosphine ligand is substituted by a neutral donor ligand which is linked to the indenylidene carbene. The resulting catalyst is a 3-phenylindenylidene Hoveyda analogue catalyst.

In PCT/US2011/029690 (WO 2011/119778 A2) a hexa-coordinated catalyst is claimed, however in this document no catalysts were isolated; a synthetic method for the in-situ generation of olefin metathesis catalysts is disclosed since according to Schrödi the synthesis of these complexes is relatively cumbersome. The synthesis usually involves more than one step and requires isolation of the catalysts to remove catalyst-inhibiting byproducts such as liberated phosphines. The resulting in-situ generated catalysts are all phenylindenylidene Hoveyda analogue catalysts.

Other non-chelating indenylidene catalysts bearing functional groups or substituents on the indenylidene part, different from phenylindenylidene, are until now not known.

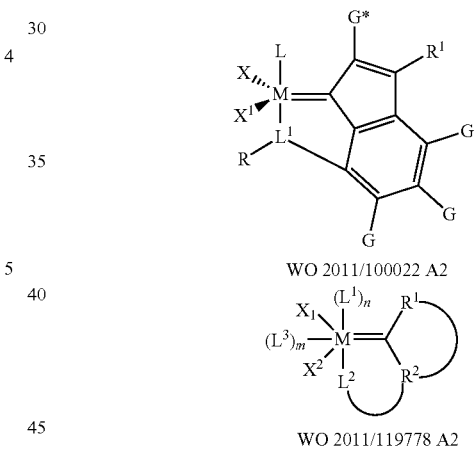

In WO 2011/009721 A1 bis-Schiff base catalysts are described on page 18-20 "via route B" starting from 5 with L=SIMes wherein it is said that the reaction mixture was investigated with $^1$H and $^{31}$P NMR revealing a quantitative transformation to the desired bis-Schiff Base catalyst. However, none of those compounds contain any P-ligand. Furthermore, the catalysts prepared via "route A" were investigated with $^1$H and $^{31}$P NMR revealing a quantitative transformation to the desired bis-Schiff Base catalyst, though, no values are given.

Moreover, it is said that the bis-Schiff base catalyst (catalyst 4 on page 22) has an extreme latent character even at 200° C. (catalyst 4/DCPD ratio: 1/15000) as was proven with DSC. However, it is well-know that DCPD when heated above 150° C., undergoes a retro-Diels-Alder reaction to yield cyclopentadiene and the boiling point is 170° C.

Additionally, it is said in the "summary of the invention" page 4 that the catalysts are obtained by a simple, efficient, green and highly yielding synthetic process. However, the catalysts procedure for the catalysts synthesis is 72 h (without purification steps) which can not be called "efficient" or industrial attractive. Besides of all the synthesized catalysts no yield is mentioned.

The ruthenium carbene part (indenylidene) in WO 2011/009721 A1 is defined as in WO 00/15339. The most preferably carbene part is a phenylindenylidene ligand. Yet, no substituted phenylindenylidene ligands are claimed.

Despite the advances achieved in the preparation and development of olefin metathesis catalysts, a continuing need exists for new improved synthetic methods and new catalysts. Of particular interest are methods that provide the preparation of new catalysts, which easily can be prepared on industrial scale.

Notwithstanding the different available catalysts, from industrial point of view, catalysts of which their performance is easy tunable by a simple straightforward modification are highly desired. Of particular interest are catalysts which can be modified from completely latent to highly active; latent catalysts find easily application in ROMP e.g. DCPD polymerization via RIM, highly active catalysts find easily application in cross metathesis e.g. ethenolysis.

Moreover, easy tunable catalysts can be obtained by tuning of the electron density of the catalyst by variation of the alkylidene (e.g. indenylidene) in combination with ligands (e.g. ditopic or multitopic ligands). However, the combination of non-chelating substituted/functionalised indenylidene with ditopic or multitopic ligands is still not existing and offers extra advantage in terms of initiation tunability which results in catalysts which can be varied from real latent to highly active.

Additionally, the catalysts of present invention afford latent catalysts stable in the monomer and highly active after an industrially acceptable activation process, a property of which there is still a high demand.

Furthermore, the instant invention's metathesis catalyst compounds provide both a mild and commercially economical and an "atom-economical" route to desirable olefins, which in turn may be useful in the preparation of linear alpha-olefins, unsaturated polymers, cyclic olefins, etc. . . . .

Another important parameter for the evaluation of metathesis catalysts is the need for catalysts that can be separated from the final metathesis product easily. For applications of metathesis reactions in pharmaceutical industry, the ruthenium level in drugs must not exceed 5 ppm. (http://www.e-mea.europa.eu/pdfs/human/swp/444600en.pdf for EMEA regulations) Up to date, different protocols were reported to remove ruthenium from metathesis products to meet these criteria. The employed protocols include removal of ruthenium by oxidation reactions ($H_2O_2$, $PPh_3O$, DMSO or $Pb(OAc)_4$, water extraction, scavengers, supported phosphine ligands, or treatment with active charcoal combined with chromatography. These protocols only decreased the ruthenium concentration in the final product to 100-1200 ppm, which is far from the required criteria for pharmaceutical applications. The immobilization of catalysts (organic or inorganic support) gave promising results with moderate success for efficient removal of ruthenium. As another strategy, modification of the ligands by more polar groups or alternation of their steric hindrance to ease their separation from metathesis products was also reported. Grela successfully modified Hoveyda-Grubbs type catalysts with ionic-tagged ligands which exhibits a good affinity towards silica gel. (Green Chem., 2012, 14, 3264.) However, the synthesis of an ionic-tagged ligand is cumbersome. The catalysts of this invention, obtained via a straightforward synthesis procedure, show an extremely high affinity for silica especially catalysts bearing multitopic ligands making them extremely useful and attractive for pharmaceutical and fine chemical applications.

The synthesis of $RuCl_2(PCy_3)_2$(3-phenylindenylidene) has proven useful in providing an easy route to ruthenium alkylidenes which avoids costly diazo preparations (Platinum Metals Rev. 2005, 49, 33).

In order to obtain an economically viable process for linear α-olefins (e.g. 1-decene) production via the cross-metathesis of ethylene and biodiesel (such as animal or vegetable oils), higher activity catalysts or more stable catalysts must be developed. Moreover, there is still a need for the development of catalysts with equivalent or better performance characteristics but synthesized directly from less expensive and readily available starting materials.

As there is a continuous need in the art for improving catalyst efficiency, i.e. improving the yield of the reaction catalysed by the said catalyst component after a certain period of time under given conditions (e.g. temperature, pressure, solvent and reactant/catalyst ratio) or else, at a given reaction yield, providing milder conditions (lower temperature, pressure closer to atmospheric pressure, easier separation and purification of product from the reaction mixture) or requiring a smaller amount of catalyst (i.e. a higher reactant/catalyst ratio) and thus resulting in more economic and environment-friendly operating conditions. This need is still more stringent for use in reaction-injection molding (RIM) processes such as, but not limited to, the bulk polymerisation of endo- or exo-dicyclopentadiene, or formulations thereof.

There is also a specific need in the art, which is yet another goal of this invention, for improving reaction-injection molding (RIM) processes, resin transfer molding (RTM) processes and reactive rotational molding (RRM) processes such as, but not limited to, the bulk polymerisation of endo- or exo-dicyclopentadiene, or copolymerization thereof with other monomers, or formulations thereof. More specifically there is a need to improve such processes which are performed in the presence of multicoordinated transition metal complexes, in particular ruthenium complexes. All the above needs constitute the various goals to be achieved by the present invention; nevertheless other advantages of this invention will readily appear from the following description.

SUMMARY OF THE INVENTION

The present invention is directed to addressing one or more of the above-mentioned issues. The invention is based on the unexpected finding that improved metathesis of unsaturated compounds such as olefins and alkynes can be obtained by catalysts having a general structure of formula (I-II) and (VII) by modifying the alkylidene part of group 8 catalysts of the prior art in combination with a ditopic or multitopic ligand(s).

The present invention provides catalysts which can be easily and efficiently activated by a chemical activator (Brønsted and Lewis acids) or a photo-activator (Photo acid generator, PAG) showing exceptional activity after activation. The catalysts of present invention can also be activated by in-situ generation of a Brønsted acid by combining a Lewis acid, which at least contains one halogen atom, with any —OH or —SH containing molecule(s) (liquid or solid, organic or inorganic).

In a preferred embodiment of the invention, unsaturated carboxylic acids and/or esters of unsaturated carboxylic acids individually and/or mixtures of the unsaturated carboxylic acids or mixtures of esters of unsaturated carboxylic acids can be converted. The catalysts of this invention are preferably used in concentrations of less than or equal to 1000 ppm, in particular in the range from 1 to 1000 ppm, preferably 5 to 200 ppm. The inventive method can be carried out at temperatures between 0 to 100° C., preferably between 20 to 90° C., are carried out in particular between 40 to 80° C.

The method can be performed using conventional solvents, in which the reactant(s) and the catalyst are dissolved, e.g. hydrocarbons or alcohols. In a preferred embodiment of the invention the method may be carried out solventless.

Via this inventive method unsaturated α,ω dicarboxylic acids and unsaturated α,ω dicarboxylic acid diesters are obtained together with the corresponding unsaturated hydrocarbons. A separation of the mixture can be done, for example, by distillation, by fractionated crystallization or by extraction. These products produced by the inventive method unsaturated α,ω dicarboxylic acids and unsaturated α,ω dicarboxylic acid diester can be used in e.g. cosmetic preparations. If necessary, the products thus obtained can be subjected to hydrogenation.

The present invention is also based on the unexpected finding that the synthesis time of the organometallic compounds of formula (I-II) and (VII) can be reduced to 4 hours or less while maintaining high to excellent yields.

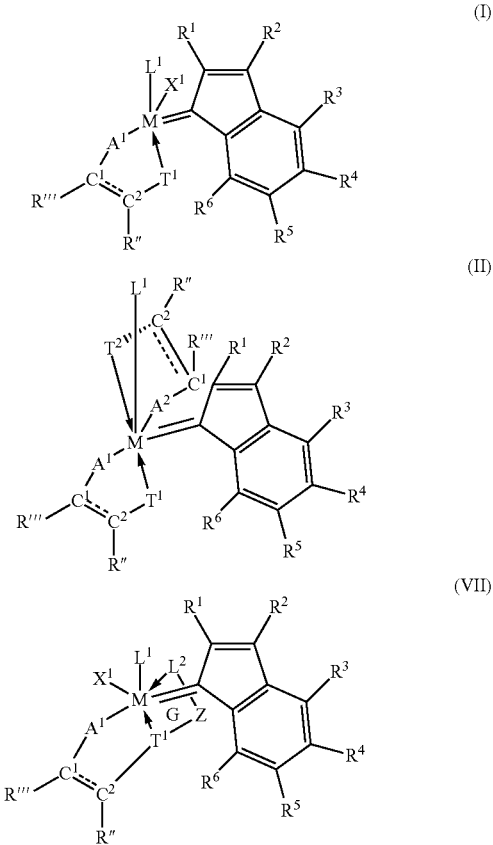

The organometallic catalyst compounds of the present invention can be prepared by contacting a Group 8 metal precursor compound with at least one ditopic ligand which alternatively can bear at least an extra chelating moiety.

Wherein,

M is a Group 8 metal, preferably ruthenium or osmium;

$R^1$-$R^6$ are identical or different and selected from H, hydrocarbyl, substituted hydrocarbyl, heteroatom containing hydrocarbyl, substituted heteroatom-containing hydrocarbyl, and functional groups, except that $R^2$ does not represent phenyl when $R^1$=$R^3$=$R^4$=$R^5$=$R^6$=H;

wherein alternatively in each case two directly adjacent radicals from the group of $R^1$-$R^6$, including the ring carbon atoms to which they are attached by a cyclic bridging group, generating one or more cyclic structures, including aromatic structures;

$X^1$ preferably represents an anionic ligand;

$L^1$ preferably represents a neutral electron donor;

$L^1$ and $X^1$ may be joined to form a multidentate monoanionic group and may form single ring of up to 30 non-hydrogen atoms or a multinuclear ring system of up to 30 non-hydrogen atoms;

$A^1$-$A^2$ are identical or different and are selected from the group consisting of oxygen, sulphur, selenium, NR"", PR"", POR"", AsR"", AsOR"", SbOR"" and SbR"";

$T^1$-$T^2$ are identical or different and are selected from the group consisting of:

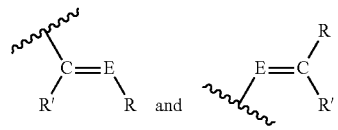

wherein E preferably represents a donor atom selected from the group consisting of nitrogen, phosphor, oxygen, sulphur, and selenium; wherein for the group

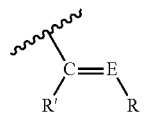

in case of oxygen, sulphur and selenium, R is omitted for double bonded E or R remains for a single bonded E; wherein for the group

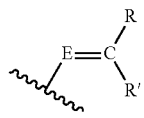

in case of oxygen, sulphur and selenium, the E-C bound is a single bond and the C atom contains an extra R group or the C—R' is a double bond or the C—R is a double bond.

R, R', R", R'" and R"" are identical or different and selected from H, hydrocarbyl, substituted hydrocarbyl, heteroatom containing hydrocarbyl, substituted heteroatom-containing hydrocarbyl, and functional groups;

wherein alternatively in each case two directly adjacent radicals from the group of R, R', R", R'" and R"", including the carbon atoms to which they are attached, generating one or more cyclic structures, including aromatic structures.

$C^1$-$C^2$ are carbon atoms linked to each other via a single or double bond wherein in case of a single bond each carbon atom bears an extra substituent $R^{C1}$ and $R^{C2}$; $R^{C1}$ and $R^{C2}$ are identical or different and are as defined for R', R", R'" and R"".

In an extra aspect, the invention provides a method for performing a catalytic metathesis reaction comprising contacting at least one olefin or olefinic compound with the metathesis catalyst of the invention. An olefin includes a single olefin, multi-olefin as well as a combination or mixture of two or more olefins, reference to "a substituent" encompasses a single substituent as well as two or more substituents, and the like.

In a further aspect the present invention is based on the unexpected finding that superior catalysts (I-II, VII) useful in the metathesis of unsaturated compounds such as olefins and alkynes, their activity can even be extra enhanced by bringing into contact a metal complex (I-II, VII) with an activating compound (hereinafter also referred as "activator") selected from Brønsted acids (Brønsted acids are proton donors, which is the commonly accepted practice among chemists). The nature of the Brønsted acid can be liquid, solid, inorganic or organic. Well-know representative compounds of Brønsted acids, but not limited, are HCl, HBr, $H_2SO_4$, $CH_3COOH$, sulphonic acid resins, etc.

In a further aspect the present invention is based on the unexpected finding that superior catalysts useful in the metathesis of unsaturated compounds such as olefins and alkynes can be obtained by bringing into contact a metal complex (I-II, VII) with an activating compound (hereinafter also referred as "activator") selected from the group consisting of:

$M^a$(I) halides.

compounds represented by the formula $M^a X_{2-y} R^a_y$ (0≤y≤2).

wherein $R^a$ is equal to $R^1$-$R^6$ defined as herein-above,

X is atom of the halogen group and identical or different in case more then one halogen atom is present, and $M^a$ is an atom having an atomic mass from 27 to 124 and being selected from the group consisting of groups IB, IIB, IIIA, IVB, IVA and VA of the Periodic Table of elements under conditions such that at least partial cleavage of a bond between the metal and the ditopic or multitopic ligand of said catalyst occurs.

compounds represented by the formula $M^a X_{3-y} R^a_y$ (0≤y≤3) wherein $R^a$, X and $M^a$ defined as herein-above.

compounds represented by the formula $M^a X_{4-y} R^a_y$ (0≤y≤4) wherein $R^a$, X and $M^a$ defined as herein-above.

compounds represented by the formula $M^a X_{5-y} R^a_y$ (0≤y≤5) wherein $R^a$, X and $M^a$ defined as herein-above.

compounds represented by the formula $M^a X_{6-y} R^a_y$ (0≤y≤6) wherein $R^a$, X and $M^a$ defined as herein-above.

In yet another specific embodiment, the present invention is based on the unexpected finding that useful catalytic species can be suitably obtained by reacting an activator such as defined hereinabove, provided that said activator includes at least one halogen atom, in the presence of at least one further reactant having the formula RYH, wherein Y is selected from the group consisting of oxygen, sulphur and selenium, and R as defined hereinabove. According to this specific embodiment, a strong acid (such as a hydrogen halide) may be formed in situ by the reaction of said activator, with said further reactant having the formula RYH, and said strong acid if produced in sufficient amount may in turn be able:

in a first step, to protonate the ditopic (or multitopic) ligand and decoordinate $T^1$ (in case of structure (I)) or $T^1$ or $T^2$ or both (in case of structure (II)) of said ditopic (or multitopic) ligand from the complexed metal, and in a second step, to decoordinate the further heteroatom of said ditopic (or multitopic) ligand from the complexed metal.

In this specific embodiment, at least partial cleavage of a bond between the metal and the ditopic (or multitopic) ligand of said metal complex occurs like in the absence of the further reactant having the formula RYH, but coordination of $T^1$ or $T^2$ or both atoms of the ditopic (or multitopic) ligand to the activator occurs less frequently because it competes unfavourably with the protonation/decoordination mechanism resulting from the in situ generation of a strong acid (such as a hydrogen halide). This alternative mechanism is however quite effective in the catalysis of metathesis reactions of olefins and alkynes since it provides a more random distribution of the strong acid in the reaction mixture than if the same strong acid is introduced directly in the presence of catalyst (I-II,VII).

The new catalytic species of the invention may be produced extra-temporaneously, separated, purified and conditioned for separate use in organic synthesis reactions later on, or they may be produced in situ during the relevant chemical reaction (e.g. metathesis of unsaturated organic compounds) by introducing a suitable amount of the activator into the reaction mixture before, simultaneously with, or alternatively after the introduction of the starting catalyst compound. The present invention also provides catalytic systems including, in addition to said new catalytic species or reaction products, a carrier suitable for supporting said catalytic species or reaction products.

The present invention also provides methods and processes involving the use of such new catalytic species or reaction products, or any mixture of such species, or such catalytic systems, in a wide range of organic synthesis reactions including the metathesis of unsaturated compounds such as olefins and alkynes and In particular, this invention provides an improved process for the ring opening polymerization of strained cyclic olefins such as, but not limited to, dicyclopentadiene.

In the context of this invention, all the above and below mentioned, general or preferred ranges of definitions, parameters or elucidations among one another, or also between the respective ranges and preferred ranges can be combined in any manner.

In the context of this invention, related to the different types of metathesis catalysts, the term "substituted" means that a hydrogen atom or an atom is replaced by a specified group or an atom, and the valence of the atom indicated is not exceeded and the substitution leads to a stable compound.

DETAILED DESCRIPTION

Terminology and Definitions

Figure 1:
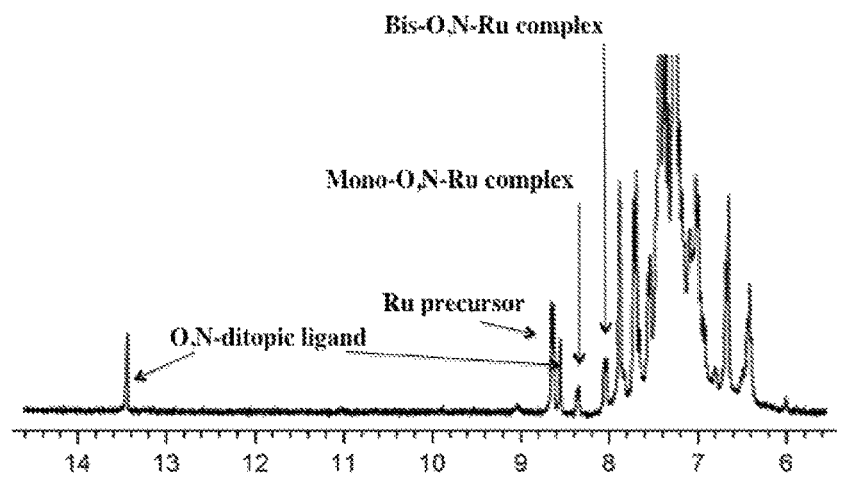
FIG. 1 is reaction progress after 1 h during the synthesis of catalyst 12.

Unless otherwise mentioned, the invention is not limited to specific reactants, substituents, catalysts, reaction conditions, or the like, as such may vary. It is also to be understood that the terminology used herein is for the purpose of describing particular embodiments only and is not intended to be limiting.

In this specification and in the claims that follow, reference will be made to a number of terms, which shall be defined to have the following meanings:

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "$C_1$-$C_6$-alkyl" intends an alkyl group of 1 to 6 carbon atoms, and the specific term "cycloalkyl" intends a cyclic alkyl group, typically having 3 to 8 carbon atoms.

The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the term "alkyl" includes linear, branched, cyclic, unsubstituted, substituted, and/or heteroatom-containing alkyl.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, and the like. Preferred alkenyl groups herein contain 2 to about 12 carbon atoms. The term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the term "alkenyl" include linear, branched, cyclic, unsubstituted, substituted, and/or heteroatom-containing alkenyl.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the term "alkynyl" include linear, branched, unsubstituted, substituted, and/or heteroatom-containing alkynyl respectively.

The term "alkoxy" as used herein intends an alkyl group bound through a single, terminal ether linkage; that is, an "alkoxy" group may be represented as —O-alkyl where alkyl is as defined above. Analogously, "alkenyloxy" refers to an alkenyl group bound through a single, terminal ether linkage, and "alkynyloxy" refers to an alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxyphenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms. Alkaryl groups include, but not limit to, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)aryl, or —O(CO)-aralkyl, wherein "alkyl," "aryl," and "aralkyl" are as defined above.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic.

The terms "halo" and "halogen" are used in the conventional sense to refer to a chloro, bromo, fluoro, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated, and unsaturated species, such as alkyl groups, alkenyl groups, aryl groups, and the like. The term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyalkyl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, 1,2,3 triazolyl, tetrazolyl, etc., and examples of heteroatom containing alicyclic groups are pyrrolidino, morpholino, piperazino, piperidino, etc.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2C_{24}$ alkylcarbonyl (—CO-alkyl) and $C_6$-$C_{24}$ arylcarbonyl (—CO-aryl)), acyloxy (—O-acyl, including $C_2C_{24}$ alkylcarbonyloxy (—O—CO-alkyl) and $C_6$-$C_{24}$ arylcarbonyloxy (—O—CO-aryl)), $C_2C_{24}$ alkoxycarbonyl (—(CO)—O—alkyl), $C_6$-$C_{24}$ aryloxycarbonyl (—(CO)—O-aryl), halocarbonyl (—CO)X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO⁻), carbamoyl (—(CO)—NH$_2$), mono-($C_1$-$C_{24}$ alkyl) substituted carbamoyl (—(CO)—NH($C_1$-$C_{24}$ alkyl)), di-($C_1$-$C_{24}$ alkyl)-substituted carbamoyl (—(CO)N($C_1$-$C_{24}$ alkyl)$_2$), mono-($C_5$-$C_{24}$ aryl)-substituted carbamoyl (—(CO)—NH-aryl), di-($C_5$-$C_{24}$ aryl) substituted carbamoyl (—(CO)—N($C_5$-$C_{24}$ aryl)$_2$), M($C_1$-$C_{24}$ alkyl) ($C_5$-$C_{24}$ aryl))-substituted carbamoyl, thiocarbamoyl (—(CS)—NH$_2$), mono-($C_1$-$C_{24}$ alkyl)-substituted thiocarbamoyl (—(CS)NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl ((CS)—N($C_5$-$C_{24}$ aryl)$_2$), N—($C_1$-$C_{24}$ alkyl)N—($C_5$-$C_{24}$ aryl)-substituted thiocarbamoyl, carbamido (NH—(CO)—NH$_2$), cyano (—C≡N), cyanato (—O—C≡N), thiocyanato (—S—C≡N), formyl (—(CO)—H), thio-formyl (—(CS)—H), amino (—NH$_2$), mono-($C_1$-$C_{24}$ alkyl)-substituted amino, di-($C_1$-$C_{24}$ alkyl) substituted amino, mono-($C_5$-$C_{24}$ aryl)-substituted amino, di-($C_5$-$C_{24}$ aryl)-substituted amino, $C_2$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N (alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N (aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O⁻), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_5$-$C_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O⁻)$_2$), phosphinato (—P(O)(O⁻)), phosphor (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{24}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

By "functionalized" as in "functionalized hydrocarbyl", "functionalized alkyl", "functionalized olefin", "functionalized cyclic olefin", and the like, is meant that in the hydrocarbyl, alkyl, olefin, cyclic olefin, or other moiety, at least one hydrogen atom bound to a carbon (or other) atom is replaced with one or more functional groups such as those described hereinabove.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

The present invention comprises a novel family of metathesis catalyst compounds useful for the different types of olefin and alkyne metathesis reactions, including but not limited to Ring closing metathesis (RCM), Cross metathesis (CM), Ring opening metathesis (ROM), Ring opening metathesis polymerization (ROMP), acyclic diene metathesis (ADMET), self-metathesis, conversion of olefins with alkynes (enyne metathesis), polymerization of alkynes, ethylene cross-metathesis and so on.

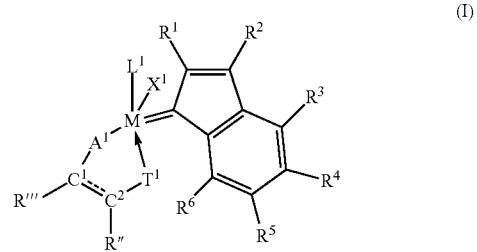

(I)

-continued

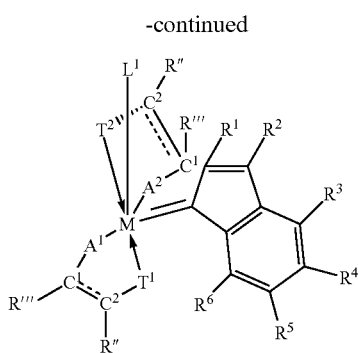

(II)

M is a Group 8 metal, preferably ruthenium or osmium, $R^1$-$R^6$ are identical or different and represents hydrogen, halogen, hydroxyl, aldehyde, keto, thiol, $CF_3$, nitro, nitroso, cyano, thiocyano, isocyanates, carbodiimide, carbamate, thiocarbamate, dithiocarbamate, amino, amido, imino, ammonium, silyl, sulphonate (—$SO_3^-$), —$OSO_3^-$, —$PO_3^-$ or —$OPO_3^-$, acyl, acyloxy or represents alkyl, cycloalkyl, alkenyl, cycloalkenyl, substituted alkenyl, heteroalkenyl, heteroatom-containing alkynyl, alkenylene, alkynyl, substituted alkynyl, aryl, substituted aryl, heteroaryl, carboxylate, alkoxy, alkenyloxy, alkynyloxy, aryloxy, alkaryl, aralkyl, alkaryloxy, aralkyloxy, alkoxycarbonyl, alkylamino-, alkylthio-, arylthio, alkyl sulfonyl, alkylsulfinyl, dialkylamino, alkylammonium, alkyl silyl or alkoxysilyl, where these radicals may each optionally all be substituted by one or more aforementioned groups defined for $R^1$-$R^6$, and except that $R^2$ does not represent phenyl when $R^1$=$R^3$=$R^4$=$R^5$=$R^6$=H;

or alternatively in each case two directly adjacent radicals from the group of $R^1$-$R^6$, including the ring carbon atoms to which they are attached by a cyclic bridging group, generating one or more cyclic structures, including aromatic structures.

$C_1$-$C_6$ alkyl is, but not limited to, for example methyl, ethyl, n-propyl, iso-propyl, n-butyl, sec-butyl, tert-butyl, n-pentyl, 1-methylbutyl, 2-methylbutyl, 3-methylbutyl, neopentyl, 1-ethyl-propyl and n-hexyl.

$C_3$-$C_8$ cycloalkyl includes, but not limited to, cyclopropyl, cyclobutyl, cyclopentyl, cyclohexyl, cycloheptyl and cyclooctyl.

$C_6$-$C_{24}$ aryl includes an aromatic radical having 6 to 24 skeletal carbon atoms. Preferred mono-, bi- or tricyclic carbocyclic aromatic radicals have 6 to 10 skeletal carbon atoms, for example but not limited to, phenyl, biphenyl, naphthyl, phenanthrenyl or anthracenyl.

$X^1$ preferably represents an anionic ligand.

In the general formulas $X^1$ can be for example, hydrogen, halogen, pseudohalogen, straight-chain or branched $C_1$-$C_{30}$ alkyl, $C_6$-$C_{24}$ aryl, $C_1$-$C_{20}$ alkoxy, $C_6$-$C_{24}$ aryloxy, $C_3$-$C_{20}$ alkyl diketonate, $C_6$-$C_{24}$ aryl diketonate, $C_1$-$C_{20}$ carboxylate, $C_1$-$C_{20}$ alkylsulfonate, $C_6$-$C_{24}$ aryl sulfonate, $C_1$-$C_{20}$ alkyl thiol, $C_6$-$C_{24}$ aryl thiol, $C_1$-$C_{20}$ alkyl sulfonyl or $C_1$-$C_{20}$ alkylsulfinyl-radicals.

The abovementioned radical $X^1$ may further be substituted by one or more additional residues, for example by halogen, preferably fluorine, $C_1$-$C_{20}$ alkyl, $C_1$-$C_{20}$-alkoxy or $C_6$-$C_{24}$ aryl, where these groups may optionally be in turn be substituted by one or more substituents from the group comprising halogen, preferable fluorine, $C_1$-$C_5$ alkyl, $C_1$-$C_5$ alkoxy, and phenyl.

$L^1$ and $X^1$ may be joined to form a multidentate monoanionic group and may form a single ring of up to 30 non-hydrogen atoms or a multinuclear ring system of up to 30 non-hydrogen atoms;

In a preferred embodiment, $X^1$ denote halogen, in particular, fluorine, chlorine, bromine or iodine, benzoate, nitrate, $C_1$-$C_5$ carboxylate, $C_1$-$C_5$ alkyl, phenoxy, $C_1$-$C_5$ alkoxy, $C_1$-$C_5$ alkyl thiol, $C_6$-$C_{24}$ arylthiol, $C_6$-$C_{24}$ aryl or $C_1$-$C_5$ alkyl sulfonate.

In a particularly preferred embodiment, $X^1$ is chlorine, $CF_3COO$, $CH_3COO$, $CFH_2COO$, $(CH_3)_3CO$, nitrate, $(CF_3)_2(CH_3)CO$, $(CF_3)(CH_3)_2CO$, PhO (phenoxy), $C_6F_5O$ (pentafluorophenoxy), MeO (methoxy), EtO (ethoxy), tosylate (p-$CH_3$—$C_6H_4$—$SO_3$), mesylate (2,4,6-trimethylphenyl) or $CF_3SO_3$ (trifluoromethanesulfonate).

$A^1$-$A^2$ are identical or different and are selected from the group consisting of oxygen, sulphur, selenium, NR"", PR"", POR"", AsR"", AsOR"", SbOR"" and SbR"".

$T^1$-$T^2$ are identical or different and selected from the group consisting of

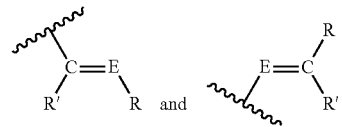

and

Wherein E preferably represents a donor atom selected from the group consisting of nitrogen, phosphor, oxygen, sulphur, and selenium; wherein for the group

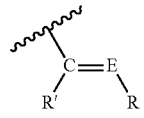

in case of oxygen, sulphur and selenium, R is omitted for double bonded E or R remains for a single bonded E; wherein for the group

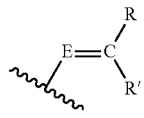

in case of oxygen, sulphur and selenium, the E-C bound is a single bond and the C atom contains an extra R group or the C—R' is a double bond or the C—R is a double bond.

R, R', R", R'" and R"" are identical or different and represents hydrogen, halogen, hydroxyl, aldehyde, keto, thiol, $CF_3$, nitro, nitroso, cyano, thiocyano, isocyanates, carbodiimide, carbamate, thiocarbamate, dithiocarbamate, amino, amido, imino, ammonium, silyl, sulphonate (—$SO_3^-$), —$OSO_3^-$, —$PO_3^-$ or —$OPO_3^-$, acyl, acyloxy or represents alkyl, cycloalkyl, alkenyl, cycloalkenyl, substituted alkenyl, heteroalkenyl, heteroatom-containing alkynyl, alkenylene, alkynyl, substituted alkynyl, aryl, substituted aryl, heteroaryl, carboxylate, alkoxy, alkenyloxy, alkynyloxy, aryloxy, alkaryl, aralkyl, alkaryloxy, aralkyloxy, alkoxycarbonyl, alkylamino-, alkylthio-, arylthio, alkyl sulfonyl, alkylsulfinyl, dialkylamino, alkylammonium, alkyl silyl or alkoxysilyl, where these radicals may each optionally all be substituted by one or more aforementioned groups defined for R, R', R", R''' and R'''', wherein alternatively in each case two directly adjacent radicals from the group of R, R', R", R''' and R'''', including the atoms to which they are attached, generating one or more cyclic structures, including aromatic structures.

$C_1$-$C_6$ alkyl is, but not limited to, for example methyl, ethyl, n-propyl, iso-propyl, n-butyl, sec-butyl, tert-butyl, n-pentyl, 1-methylbutyl, 2-methylbutyl, 3-methylbutyl, neopentyl, 1-ethyl-propyl and n-hexyl.

$C_3$-$C_8$ cycloalkyl includes, but not limited to, cyclopropyl, cyclobutyl, cyclopentyl, cyclohexyl, cycloheptyl and cyclooctyl.

$C_6$-$C_{24}$ aryl includes an aromatic radical having 6 to 24 skeletal carbon atoms. Preferred mono-, bi- or tricyclic carbocyclic aromatic radicals have 6 to 10 skeletal carbon atoms, for example but not limited to, phenyl, biphenyl, naphthyl, phenanthrenyl or anthracenyl.

Alternatively R is optionally substituted with a neutral donor ligand ($L^2$) as defined by $L^1$.

$C^1$-$C^2$ are carbon atoms linked to each other via a single or double bond wherein in case of a single bond each carbon atom bears an extra substituent $R^{C1}$ and $R^{C2}$.

$R^{C1}$ and $R^{C2}$ are identical or different and are as defined for R', R", R''' and R''''.

$L^1$ preferably represent neutral electron donor.

The ligand $L^1$ may, for example, represent a phosphine, sulphonated phosphine, phosphate, phosphinite, phosphonite, phosphite, arsine, stibine, ether, amine, amide, sulfoxide, carboxyl, nitrosyl, pyridine, substituted pyridine, pyrazine, thiocarbonyl, thioether, triazole carbene, mesionic carbene (MIC), N-Heterocyclic carbene ("NHC"), substituted NHC, or cyclic alkyl amino carbene (CAAC) or substituted CAAC.

Preferably, ligand $L^1$ represents a phosphine ligand having the formula $P(Q^1)_3$ with $Q^1$ are identical or different and are alkyl, preferably $C_1$-$C_{10}$ alkyl, more preferably $C_1$-$C_5$-alkyl, cycloalkyl-, preferably $C_3$-$C_{20}$ cycloalkyl, more preferably $C_3$-$C_8$ cycloalkyl, preferably cyclopentyl, cyclohexyl, and neopentyl, aryl, preferably $C_6$-$C_{24}$ aryl, more preferably phenyl or toluyl, $C_1$-$C_{10}$ alkyl-phosphabicyclononane, $C_3$-$C_{20}$ cycloalkyl phospha-bicyclononane, a sulfonated phosphine ligand of formula $P(Q^2)_3$ wherein $Q^2$ represents a mono- or poly-sulfonated $Q^1$-ligand; $C_6$-$C_{24}$ aryl or $C_1$-$C_{10}$ alkyl-phosphinite ligand, a $C_6$-$C_{24}$ aryl or $C_1$-$C_{10}$ alkyl phosphonite ligand, a $C_6$-$C_{24}$aryl or $C_1$-$C_{10}$ alkyl phosphite-ligand, a $C_6$-$C_{24}$ aryl $C_1$-$C_{10}$ alkyl arsine ligand, a $C_6$-$C_{24}$ aryl or $C_1$-$C_{10}$ alkyl amine ligands, a pyridine ligand, a $C_6$-$C_{24}$ aryl or $C_1$-$C_{10}$ alkyl-sulfoxide ligand, a $C_6$-$C_{24}$ aryl or $C_1$-$C_{10}$ alkyl ether ligand or a $C_6$-$C_{24}$ aryl or $C_1$-$C_{10}$ alkyl amide ligands which all can be multiply substituted, for example by a phenyl group, wherein these substituents are in turn optionally substituted by one or more halogen, $C_1$-$C_5$ alkyl or $C_1$-$C_5$ alkoxy radicals.

The term "phosphine" includes, for example, $PPh_3$, P(p-Tol)$_3$, P(o-Tol), $PPh(CH_3)_2$, $P(CF_3)_3$, P(p-FC$_6$H$_4$)$_3$, P(p-CF$_3$C$_6$H$_4$)$_3$, P(C$_6$H$_4$—SO$_3$Na)$_3$, P(CH$_2$C$_6$H$_4$—SO$_3$Na)$_3$, P(iso-Propyl)$_3$, P(CHCH$_3$(CH$_2$CH$_3$))$_3$, P(cyclopentyl)$_3$, P(cyclohexyl)$_3$, P(Neopentyl)$_3$ and cyclohexyl-phosphabicyclononane.

The term "phosphinite" includes for example triphenylphosphinite, tricyclohexylphosphinite, triisopropylphosphinite and methyldiphenylphosphinite.

The term "phosphite" includes, for example, triphenyl phosphite, tricyclohexyl phosphite, tri-tert-butyl phosphite, triisopropyl phosphite and methyldiphenylphosphite.

The term "stibine" includes, for example triphenylstibine, tricyclohexylstibine and Trimethylstibene.

The term "sulfonate" includes, for example, trifluoromethanesulfonate, tosylate and mesylate.

The term "sulfoxide" includes, for example, $CH_3S(=O)CH_3$ and $(C_6H_5)_2SO$.

The term "thioether" includes, for example $CH_3SCH_3$, $C_6H_5SCH_3$, $CH_3OCH_2CH_2SCH_3$ and tetra-hydrothiophene.

The term "pyridine" in this application is a generic term and includes all the unsubstituted and substituted nitrogen-containing ligands described in WO-A-03/011455 and U.S. Pat. No. 6,759,537 B2. Examples are: pyridine, picolines (α-, β-, and γ-picoline), lutidines (2,3-, 2,4-, 2,5-, 2,6-, 3,4- and 3,5-lutidine), collidine (2,4,6-trimethylpyridine), trifluoromethylpyridine, phenylpyridine, 4-(dimethylamino) pyridine, chloropyridines (2-, 3- and 4-chloropyridine), bromopyridines (2-, 3- and 4-bromopyridine), nitropyridines (2-, 3- and 4-nitropyridine), bipyridine, picolylimine, gamma-pyran, phenanthroline, pyrimidine, bipyrimide, pyrazine, indole, coumarine, carbazole, pyrazole, pyrrole, imidazole, oxazole, thiazole, dithiazole, isoxazole, isothiazole, quinoline, bisquinoline, isoquinoline, bisisoquinoline, acridine, chromene, phenazine, phenoxazine, phenothiazine, triazine, thianthrene, purine benzimidazole, bisimidazole, bisoxazole, pyrrole, imidazole and phenylimidazole.

In other useful embodiment ligand $L^1$ represents a N-Heterocyclic carbene (NHC) usually having a structure of the formulas (IIIa) or (IIIb):

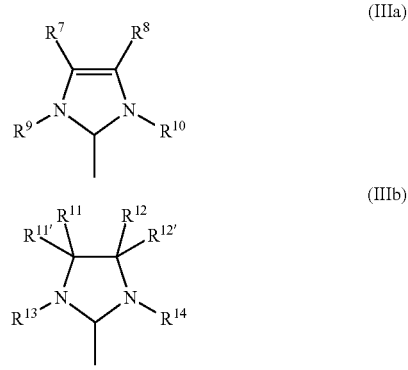

by which
$R^7$-$R^{14}$, $R^{11'}$, $R^{12'}$ are identical or different and are hydrogen, halogen, hydroxyl, aldehyde, keto, thiol, $CF_3$, nitro, nitroso, cyano, thiocyano, isocyanates, carbodiimide, carbamate, thiocarbamate, dithiocarbamate, amino, amido, imino, ammonium, silyl, sulphonate (—$SO_3^-$), —$OSO_3^-$, —$PO_3^-$ or —$OPO_3^-$, acyl, acyloxy or represents alkyl, cycloalkyl, alkenyl, cycloalkenyl, substituted alkenyl, heteroalkenyl, heteroatom-containing alkynyl, alkenylene, alkynyl, substituted alkynyl, aryl, substituted aryl, heteroaryl, carboxylate, alkoxy, alkenyloxy, alkynyloxy, aryloxy, alkaryl, aralkyl, alkaryloxy, aralkyloxy, alkoxycarbonyl, alkylammonium, alkylamino-, alkylthio-, arylthio, alkylsulfonyl, alkylsulfinyl, dialkylamino, alkylsilyl or alkoxysilyl, where these radicals may each optionally all be substituted by one or more aforementioned groups defined for $R^1$-$R^6$.

Optionally, one or more of the radicals $R^7$-$R^{14}$, $R^{11'}$, $R^{12'}$ independently of one another can be substituted by one or more substituents, preferably straight or branched $C_1$-$C_{10}$ alkyl, $C_3$-$C_8$ cycloalkyl, $C_1$-$C_{10}$ alkoxy or $C_6$-$C_{24}$ aryl, where these aforementioned substituents may in turn be substituted by one or more radicals, preferably selected from the group comprising halogen, especially chlorine or bromine, $C_1$-$C_5$ alkyl, $C_1$-$C_5$ alkoxy and phenyl.

Just for clarification, the depicted structures of the N-Heterocyclic carbene in the general formulas (IIIa) and (IIIb) are equal with the N-Heterocyclic carbenes described in the literature, where frequently the structures (IIIa') and (IIIb') are used, which highlighting the carbene character of N-Heterocyclic carbene. This also applies to the corresponding preferred, structures shown below (IVa)-(IVf)

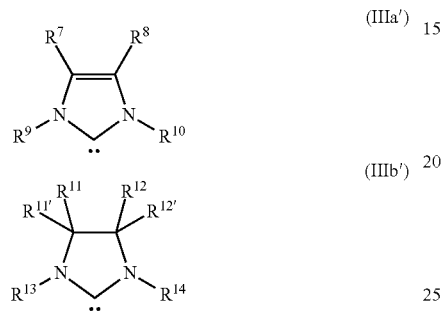

In a preferred embodiment of the catalysts the general formulas (IIIa) and (IIIb) $R^7$, $R^8$, $R^{11}$, $R^{11'}$ $R^{12}$ and $R^{12'}$ are independently of one another denote hydrogen, $C_6$-$C_{24}$-aryl, particularly preferably phenyl, straight or branched $C_1$-$C_{10}$ alkyl, particularly preferably propyl or butyl, or together with the inclusion of the carbon atoms to which they are attached form a cycloalkyl or aryl radical, where all the abovementioned radicals are optionally substituted may be substituted by one or more further radicals selected from the group comprising straight or branched $C_1$-$C_{10}$ alkyl, $C_1$-$C_{10}$ alkoxy, $C_6$-$C_{24}$ aryl, and a functional group selected from the group consisting of hydroxy, thiol, thioether, ketone, aldehyde, ester, ether, amine, imine, amide, nitro, carboxylic acid, disulfide, carbonate, isocyanate, carbodiimide, carboalkoxy, carbamate, and halogen.

In a particularly preferred embodiment, the catalysts of the general formulas (I-II) have one N-Heterocyclic carbene (NHC) as ligand $L^1$, where the radicals $R^9$, $R^{10}$, $R^{13}$ and $R^{14}$ are identical or different and are straight or branched $C_1$-$C_{10}$ alkyl, particularly preferably i-propyl or neopentyl, $C_3$-$C_{10}$ cycloalkyl, preferably adamantyl, $C_6$-$C_{24}$ aryl, particularly preferably phenyl, $C_1$-$C_{10}$ alkylsulfonate, particularly preferably methanesulphonate, $C_1$-$C_{10}$ aryl sulphonate, particularly preferably p-toluenesulfonate.

If necessary, the above-mentioned residues are substituted as the meanings of $R^9$, $R^{10}$, $R^{13}$ and $R^{14}$ by one or more further radicals selected from the group comprising straight or branched $C_1$-$C_5$ alkyl, especially methyl, $C_1$-$C_5$ alkoxy, aryl and a functional group selected from the group consisting of hydroxy, thiol, thioether, ketone, aldehyde, ester, ether, amine imine, amide, nitro, carboxylic acid, disulfide, carbonate, isocyanate, carbodiimide, carboalkoxy, carbamate, and halogen.

In particular, the radicals $R^9$, $R^{10}$, $R^{13}$ and $R^{14}$ can be identical or different and denote i-propyl, neopentyl, adamantyl, mesityl or 2,6-diisopropylphenyl.

Particularly preferred N-Heterocyclic carbenes (NHC) have the following structure (IVa)-(IVf), in which Mes stands for a 2,4,6-trimethylphenyl radical or alternatively, in all cases, for a 2,6-diisopropylphenyl radical.

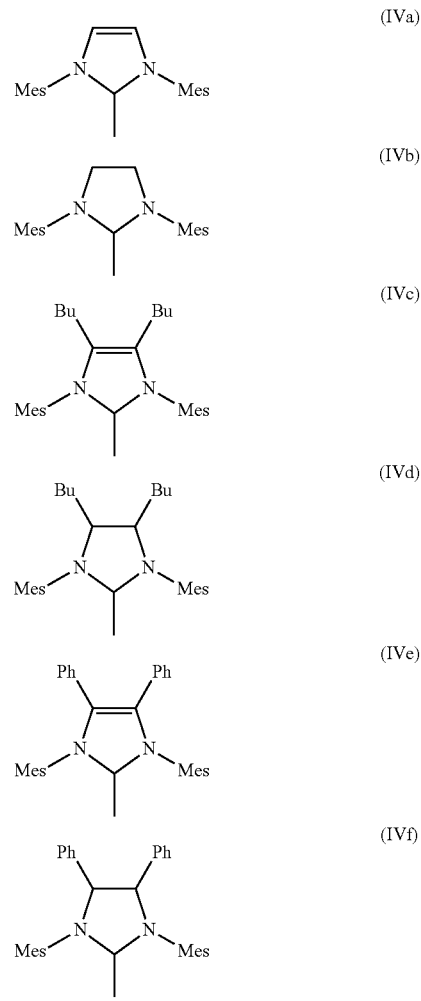

In alternative embodiment, the neutral ligand L may be selected from a ligand of any of the formulas (Va-Vc):

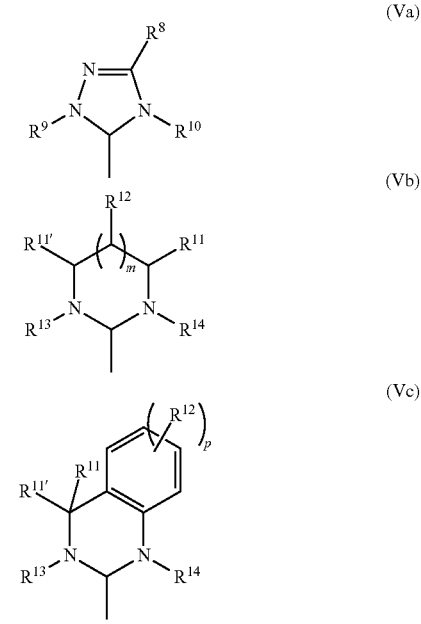

$R^8$, $R^9$, $R^{10}$, $R^{11}$, $R^{11'}$, $R^{12}$, $R^{13}$, $R^{14}$ are identical or different and are equal to $R^3$-$R^6$ defined as herein-above. Any adjacent group of $R^{11}$, $R^{11'}$ and $R^{12}$ in structure (Vb) and (Vc) may form a 3, 4, 5, 6, or 7 membered cycloalkyl, alkylene bridge, or aryl.

In other useful embodiments, one of the N groups bound to the carbene in Formula (IIIa) or (IIIb) is replaced with another heteroatom, preferably S, O or P, preferably an S heteroatom. Other useful N-heterocyclic carbenes include the compounds described in *Chem. Eur. J* 1996, 2, 772 and 1627; *Angew. Chem. Int. Ed.* 1995, 34, 1021; *Angew. Chem. Int. Ed.* 1996, 35, 1121; and Chem. Rev. 2000, 100, 39.

For purposes of this invention and claims thereto, "cyclic alkyl amino carbenes" (CAACs) are represented by the Formula (VI):

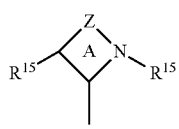

(VI)

Wherein the ring A is a 4-, 5-, 6-, or 7-membered ring, and Z is a linking group comprising from one to four linked vertex atoms selected from the group comprising C, O, N, B, Al, P, S and Si with available valences optionally occupied by hydrogen, oxo or R-substituents, wherein R is independently selected from the group comprising $C_1$ to $C_{12}$ hydrocarbyl groups, substituted $C_1$ to $C_{12}$ hydrocarbyl groups, and halides, and each $R^{15}$ is independently a hydrocarbyl group or substituted hydrocarbyl group having 1 to 40 carbon atoms, preferably methyl, ethyl, propyl, butyl (including isobutyl and n-butyl), pentyl, cyclopentyl, hexyl, cyclohexyl, octyl, cyclooctyl, nonyl, decyl, cyclodecyl, dodecyl, cyclododecyl, mesityl, adamantyl, phenyl, benzyl, toluyl, chlorophenyl, phenol, or substituted phenol.

Some particularly useful CAACs include:

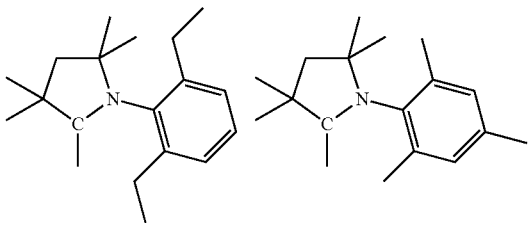

Other useful CAACs include the compounds described in U.S. Pat. No. 7,312,331 and in *Angew. Chem. Int. Ed.* 2005, 44, 7236-7239.

For the case that the R group present in $T^1$ or $T^2$ of the inventive catalysts with the general formula (I) is further substituted with a neutral donor ligand, the following examples can be generated with the structures of the general formula (VII).

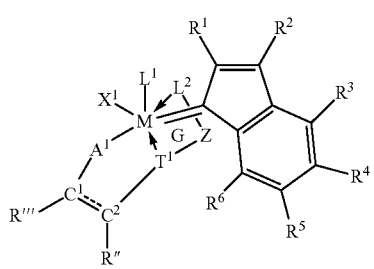

(VII)

Wherein the ring G is a 4-, 5-, 6-, 7-, 8-, 9- or 10-membered ring, and Z is a linking group comprising from one to seven linked vertex atoms selected from the group comprising C, O, N, P, S and Si with available valences optionally occupied by hydrogen, halogen, hydroxyl, aldehyde, keto, thiol, $CF_3$, nitro, nitroso, cyano, thiocyano, isocyanates, carbodiimide, carbamate, thiocarbamate, dithiocarbamate, amino, amido, imino, ammonium, silyl, sulphonate ($-SO_3^-$), $-OSO_3^-$, $-PO_3^-$ or $-OPO_3^-$, acyl, acyloxy or represents alkyl, cycloalkyl, alkenyl, cycloalkenyl, substituted alkenyl, heteroalkenyl, heteroatom-containing alkynyl, alkenylene, alkynyl, substituted alkynyl, aryl, substituted aryl, heteroaryl, carboxylate, alkoxy, alkenyloxy, alkynyloxy, aryloxy, alkaryl, aralkyl, alkaryloxy, aralkyloxy, alkoxycarbonyl, alkylamino-, alkylthio-, arylthio, alkyl sulfonyl, alkylsulfinyl, dialkylamino, alkylammonium, alkylsilyl or alkoxysilyl, where these vertex atoms may each optionally all be substituted by one or more aforementioned groups defined for R, R'', R''' and R'''', or alternatively in each case two directly adjacent vertex atoms from Z generate one or more cyclic structures, including aromatic structures.

$L^1$ and $L^2$ are identical or different ligands, preferably represent neutral electron donors, and $L^2$ has the same meaning as $L^1$ as defined in structures (I-II)

wherein M, $X^1$, $A^1$, $T^1$, $L^1$, $R^1$-$R^6$ and R', R'', R''' and R'''' have the same meanings as defined in the general structures (I-II).

As examples of the catalysts of the invention, the following structures may be mentioned:

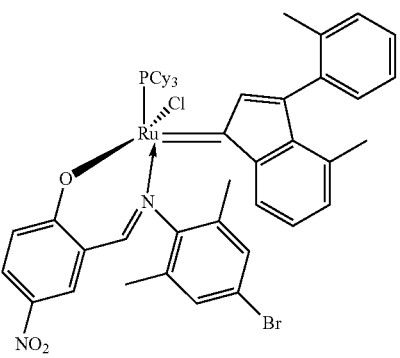

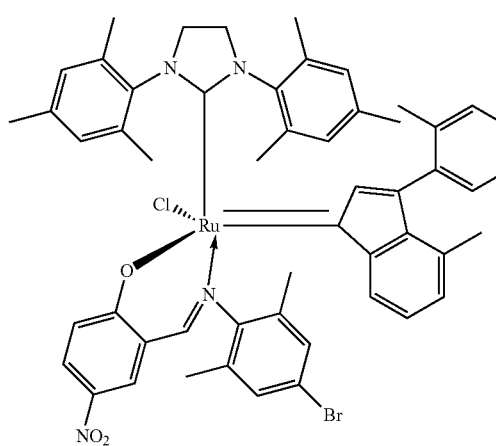

-continued
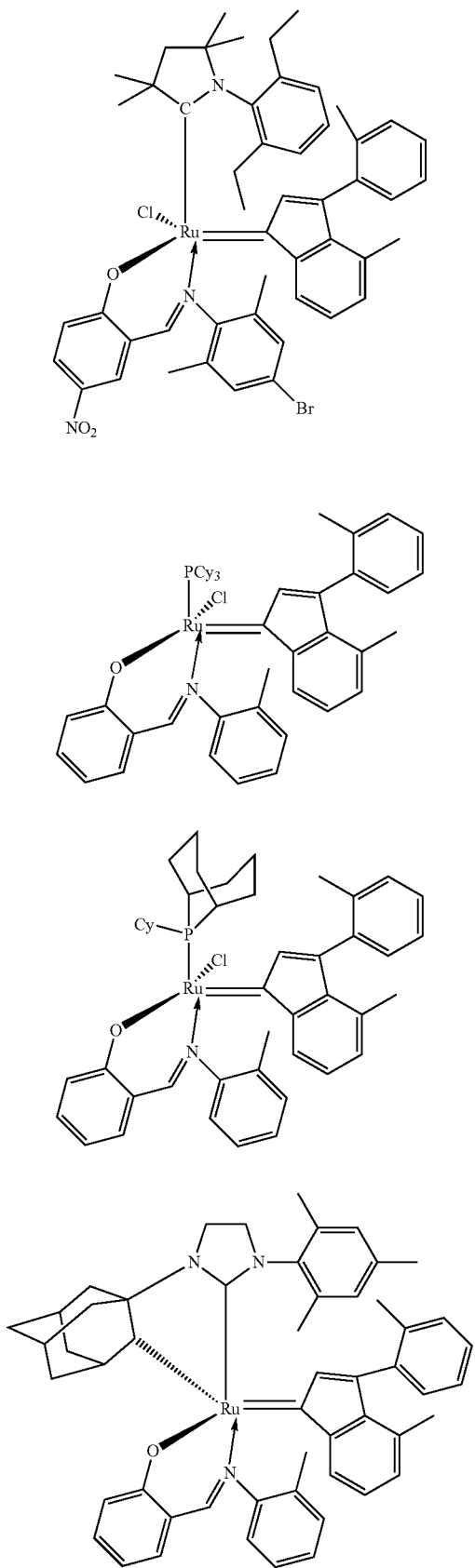
-continued
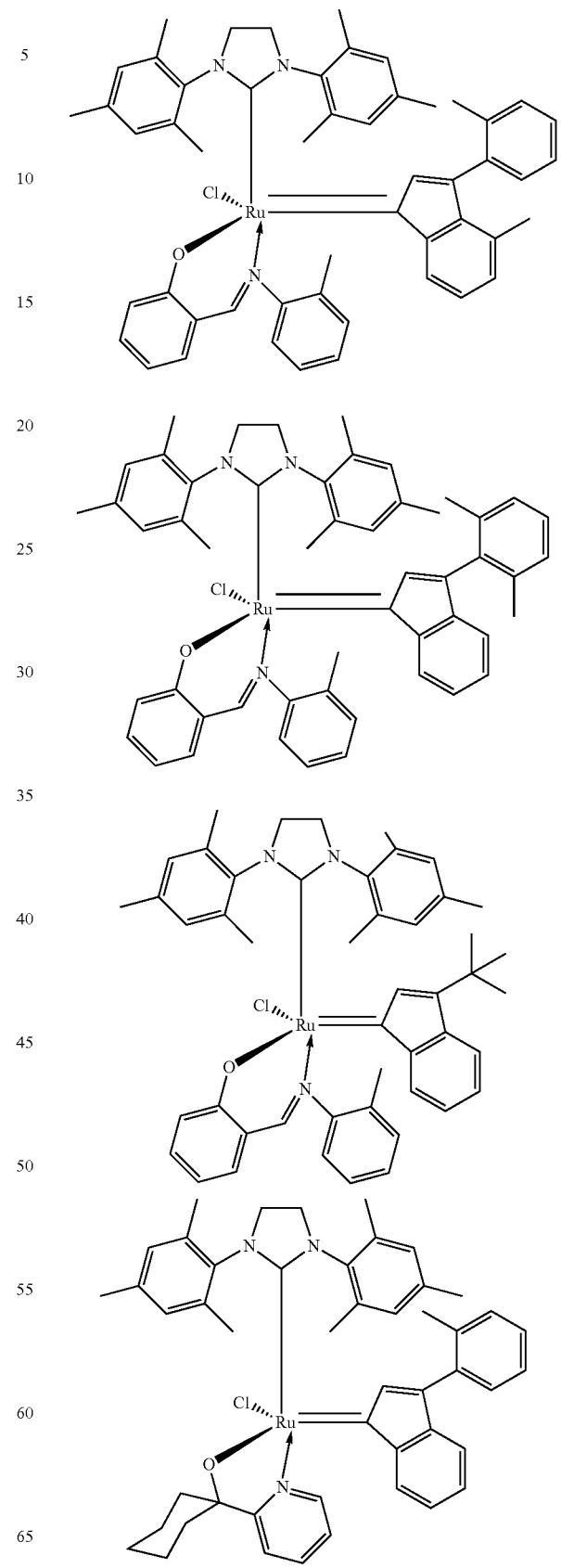

-continued
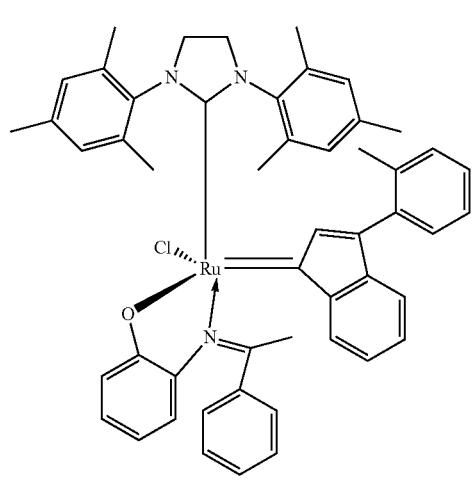
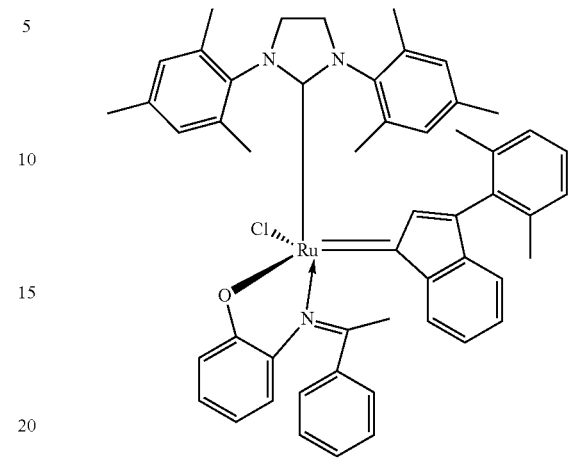
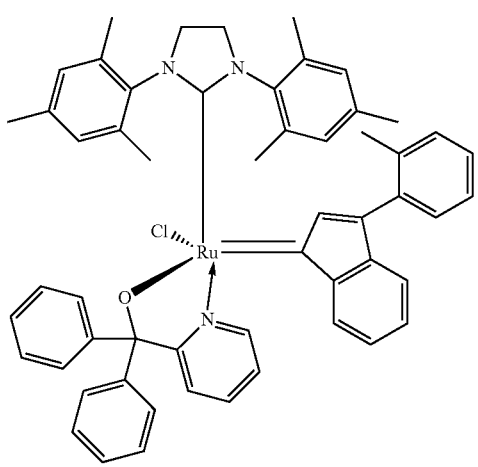
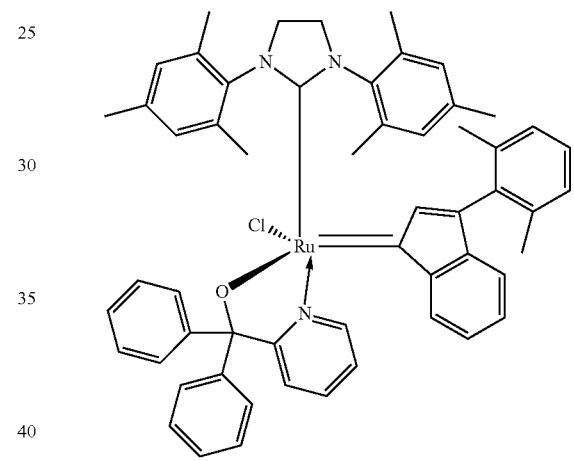
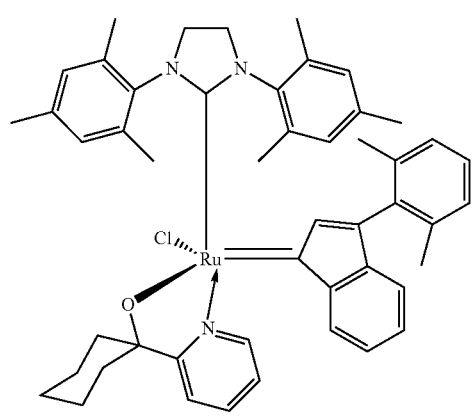
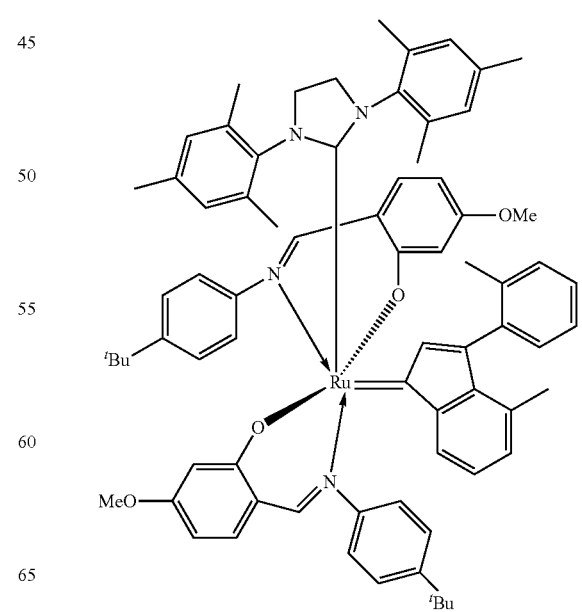

31
-continued
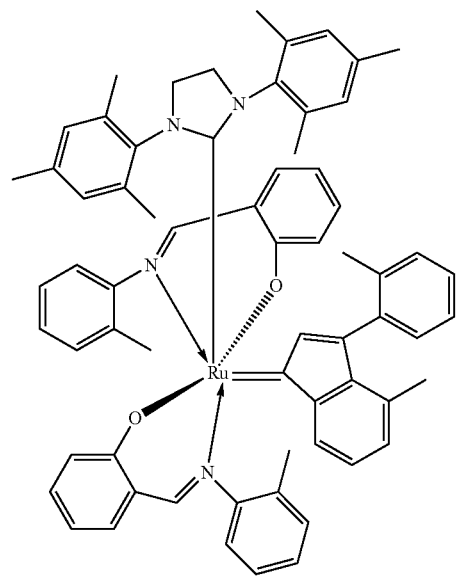
32
-continued
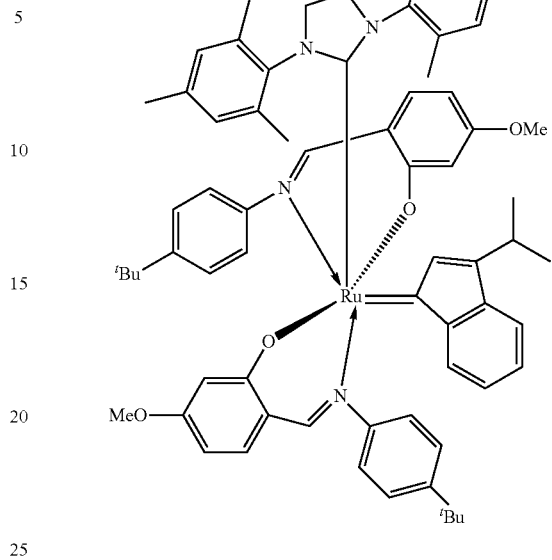
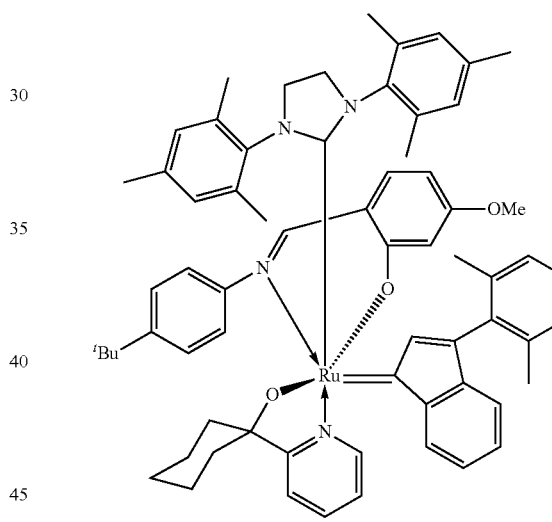
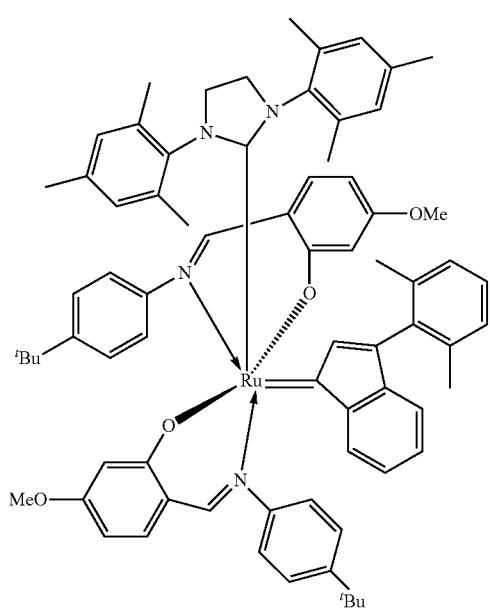
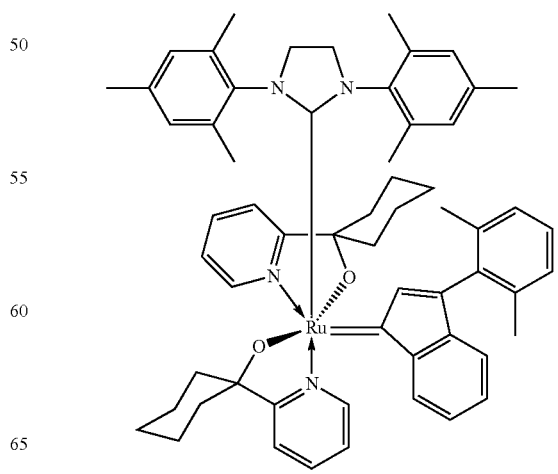

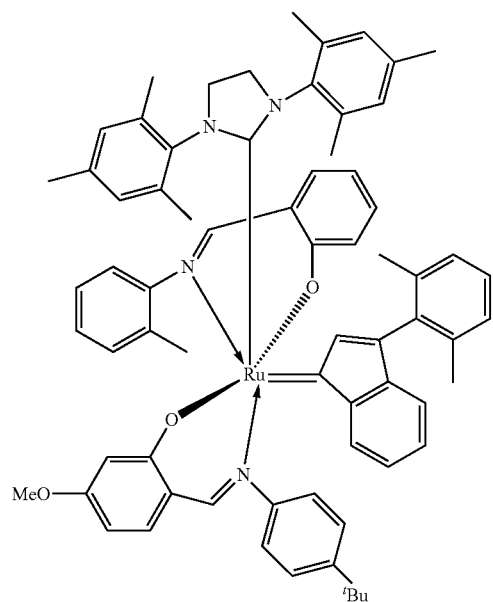

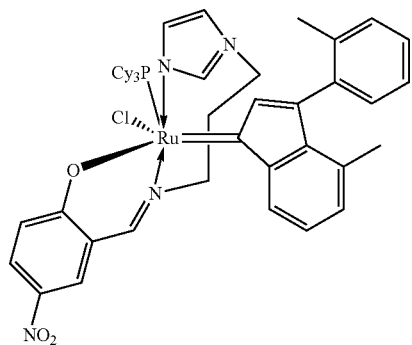

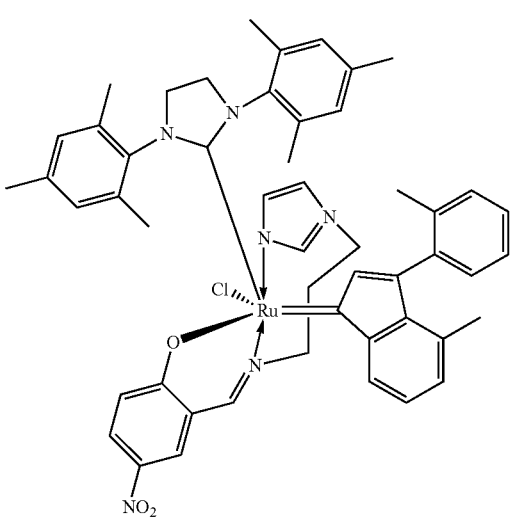

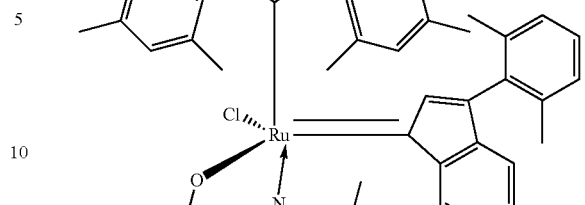

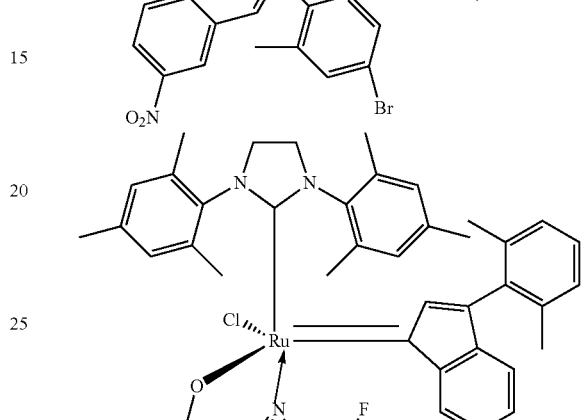

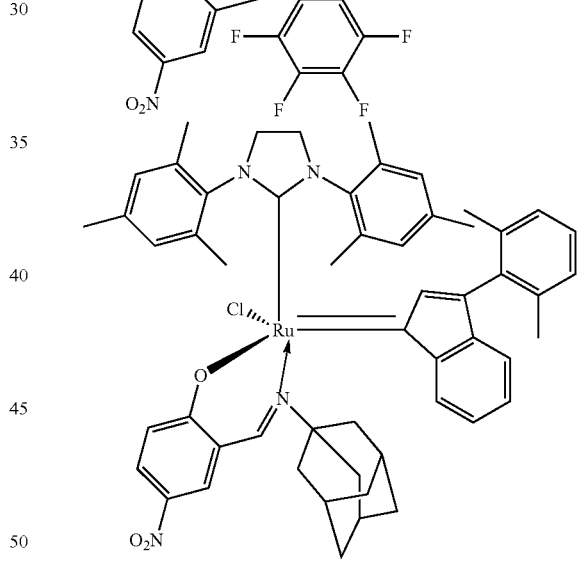

In certain embodiments, the catalyst compound employed in the olefin metathesis processes may be bound to or deposited on a solid catalyst support. The solid catalyst support will make the catalyst compound heterogeneous, which will simplify catalyst recovery. In addition, the catalyst support may increase catalyst strength and attrition resistance. Suitable catalyst supports include, without limitation, silica's, alumina's, silica-alumina's, aluminosilicates, including zeolites and other crystalline porous aluminosilicates; as well as titania's, zirconia, magnesium oxide, carbon, carbon nanotubes, graphene, Metal organic frameworks and cross-linked, reticular polymeric resins, such as functionalized cross-linked polystyrenes, e.g., chloromethyl-functionalized cross-linked polystyrenes.

The catalyst compound may be deposited onto the support by any method known to those skilled in the art, including, for example, impregnation, ion-exchange, deposition-precipitation, Π-Π interactions and vapor deposition. Alternatively, the catalyst compound may be chemically bound to the support via one or more covalent chemical bonds, for example, the catalyst compound may be immobilized by one or more covalent bonds with one or more of substituents of the indenylidene ligand or directly immobilized via one or more chemical bounds on the Group 8 metal by substituting one or more anionic ligands or immobilized via one or more chemical bounds between the ligand and the support.

If a catalyst support is used, the catalyst compound may be loaded onto the catalyst support in any amount, provided that the metathesis process proceeds to the desired metathesis products. Generally, the catalyst compound is loaded onto the support in an amount that is greater than about 0.01 wt % of the Group 8 metal, based on the total weight of the catalyst compound plus support. Generally, the catalyst compound is loaded onto the support in an amount that is less than about 20 wt % of the Group 8 metal, based on the total weight of the catalyst compound and support.

In general, acetylenic compounds useful in this invention may contain a chelating moiety of the formula (VIII)

(VIII)

wherein,
D is a leaving group;
$R^{16}$ to $R^{17}$ are as defined below;
$R^{16}$ is selected from hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkyl sulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, and wherein when $R^{16}$ is aryl, polyaryl, or heteroaryl, $R^{16}$ may be substituted with any combination of $R^1$, $R^2$, $R^3$, $R^4$, $R^5$, and $R^6$ and can be linked with any of $R^1$, $R^2$, $R^3$, $R^4$, $R^5$, and $R^6$ to form one or more cyclic aromatic or non-aromatic groups.

$R^{17}$ is selected from annulenes, having the general formula $C_nH_n$ (when n is an even number) or $C_nH_{n+1}$ (when n is an odd number). Well-know representative compounds of annulenes, but not limited, are cyclobutadiene, benzene, and cyclooctatetraene. Annulenes can be aromatic or anti-aromatic. Every H-atom from the annulene fragment can be substituted by halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkyl sulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, and wherein when $R^{17}$ is aryl, polyaryl, or heteroaryl, $R^{17}$ may be substituted with any combination of $R^1$, $R^2$, $R^3$, $R^4$, $R^5$, and can be linked with any of $R^1$, $R^2$, $R^3$, $R^4$, $R^5$ and $R^6$ to form one or more cyclic aromatic or non-aromatic groups.

Examples of suitable leaving groups include, but are not limited to, hydroxyl, halide, ester, perhalogenated phenyl, acetate, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, D is selected from hydroxyl, halide, $CF_3CO_2$, $CH_3CO_2$, $CFH_2CO_2$, $(CH_3)_3CO_3(CF_3)_2(CH_3)CO$, $(CF_3)(CH_3)_2CO$, PhO, MeO, EtO, tosylate, mesylate, or trifluoromethanesulfonate. In particular embodiments, D is advantageously hydroxyl (OH).

Preferred organic acetylenic compounds are of the formula (IX),

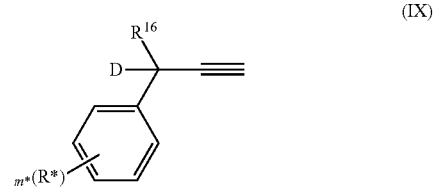

(IX)

Wherein
m* is an integer from 1 to 5;
R* is selected from $R^1$, $R^2$, $R^3$, $R^4$, $R^5$ and $R^6$, or combinations thereof, as defined above.
D and $R^{16}$ are as defined above.
Preferred organic acetylenic compounds include:

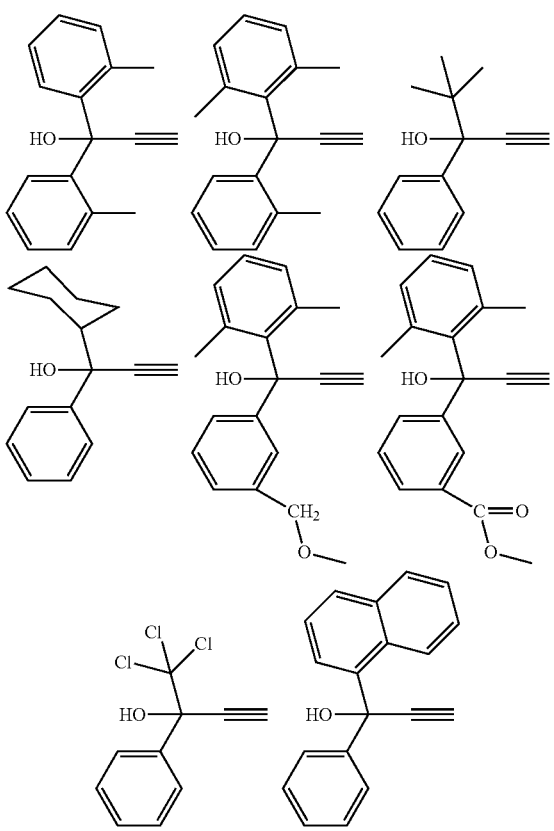

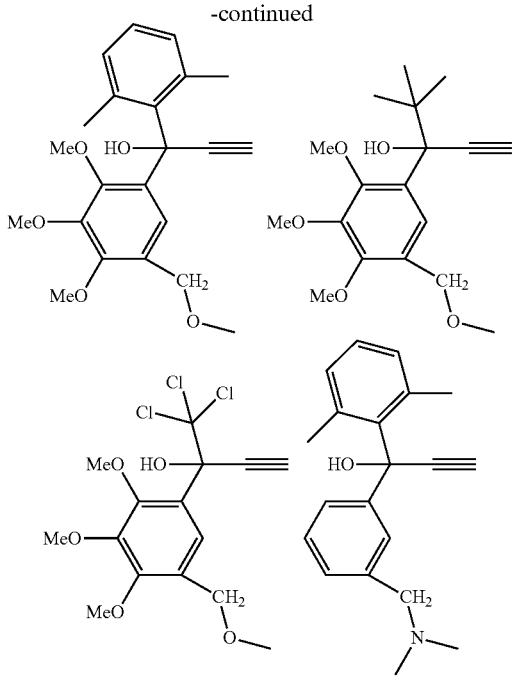

Synthesis of Metathesis Catalyst Compounds

The catalyst compounds described in this invention may be synthesized by any methods known to those skilled in the art.

Representative methods of synthesizing the Group 8 catalyst compound of the type described herein include, for example, treating a solution of the acetylenic compound in a suitable solvent, such as dioxane, with a reactant complex of a Group 8 metal, such as dichlorobis-(triphenylphosphine)ruthenium(II) and hydrogen chloride (in dioxane). The reaction mixture may be heated, for a time period appropriate to yield the desired modified indenylidene catalyst compound. Typically, removal of the volatiles and washed with hexane affords the Group 8 modified indenylidene 1$^{st}$ generation compound (Scheme 4) in high yields (>80%).

A phosphine ligand, such as tricyclohexylphosphine, cyclohexyl-phosphabicyclononane, a phosphinite or a phosphinite may be added thereafter, if desired. The reaction conditions typically include mixing the Group 8 reactant compound and the preferred phosphine ligand in a suitable solvent, e.g. dichloromethane, for a time sufficient to effectuate the phosphine ligand exchange, at a suitable temperature typically ambient, yield (>90%).

A N-Heterocyclic carbenes (NHC), such as 1,3-Bis(2,4,6-trimethylphenyl)-2-imidazolidinylidene, 1,3-bis(2,6-diisopropylphenyl)-2-imidazolidinylidene or a CAAC may be added 1$^{st}$ generation compound (Scheme 4), if desired. The reaction conditions typically include mixing the Group 8 reactant 1$^{st}$ generation compound (Scheme 4) and the preferred NHC, CAAC ligand in a suitable solvent, e.g. toluene, for a time sufficient to effectuate the phosphine ligand exchange, at a suitable temperature typically between ambient and 80° C. Addition of isopropanol followed by filtration and washing, the desired 2$^{nd}$ generation compound (Scheme 4) is obtained in high yield (>85%).

A pyridine ligand, such as pyridine, 3-Br pyridine may be added 2$^{nd}$ generation compound (Scheme 4), if desired. The reaction conditions typically include mixing the Group 8 reactant 2$^{nd}$ generation compound (Scheme 4) and the preferred pyridine ligand in as solvent, for a time sufficient to effectuate the phosphine ligand exchange, at a suitable temperature typically between ambient and 80° C. Filtration and washing gives the desired 3$^{rd}$ generation compound (Scheme 4) in high yield (>85%).

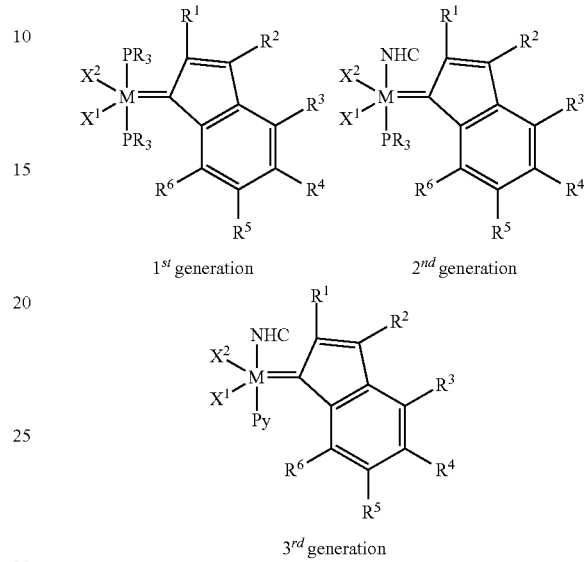

Scheme 4: different generations of non-chelating modified indenylidene catalysts.

Treating a solution of the ditopic (or multitopic) ligand, e.g. O,N-bidentate ligands, in a suitable solvent, such as THF, with a 1$^{st}$ or 2$^{nd}$ or 3$^{rd}$ generation non-chelating modified indenylidene complex (see scheme 4), e.g. (Simes)(PCy$_3$)Cl$_2$Ru(3-2-methylphenyl-5-methylphenyl-inden-1-ylidene in a 1:1 ratio and adding a required amount of silver (e.g. AgO$_2$) for a time sufficient to effectuate the ligand exchange, at a suitable temperature typically between ambient and 80° C. to yield the desired modified indenylidene catalyst compound. The reaction temperature was then lowered to room temperature, the white precipitate of PCy$_3$AgCl (byproduct) and excess of Ag$_2$O was removed by filtration and the filtrate was concentrated under reduced pressure. The isolated solid residue provides the desired product (type I) in high yield (>85%).

Treating a solution of the ditopic (or multitopic) ligand, e.g. O,N-bidentate ligands, in a suitable solvent, such as THF, with a 1$^{st}$ or 2$^{nd}$ or 3$^{rd}$ generation non-chelating modified indenylidene complex (see scheme 4), e.g. (Simes)(PCy$_3$)Cl$_2$Ru(3-2-methylphenyl-5-methylphenyl-inden-1-ylidene in a 2:1 ratio and adding an equivalent amount of silver (e.g. AgO$_2$) for a time sufficient to effectuate the ligand exchange, at a suitable temperature typically between ambient and 80° C. to yield the desired modified indenylidene catalyst compound. The reaction temperature was then lowered to room temperature, the white precipitate of PCy$_3$AgCl (byproduct) and excess of Ag$_2$O was removed by filtration and the filtrate was concentrated under reduced pressure. The isolated solid residue provides the desired product (type II) in high yield (>85%).

Treating a solution of the ditopic (or multitopic) ligand, e.g. O,N-bidentate ligands, in a suitable solvent, such as THF, with a catalyst of type I in a 1:1 ratio and adding a required amount of silver (e.g. AgO$_2$) for a time sufficient to effectuate the ligand exchange, at a suitable temperature typically between ambient and 80° C. to yield the desired modified indenylidene catalyst compound. The reaction temperature was then lowered to room temperature, the white precipitate of PCy$_3$AgCl (byproduct) and excess of Ag$_2$O was removed by filtration and the filtrate was concentrated under reduced pressure. The isolated solid residue provides the desired product (type II) in high yield.

The exchange of the ditopic (or multitopic) ligands can also be performed by generating first the salt of the ligand (Sodium, Potassium, Magnesium, Thallium salts, . . . ) as is well-know by persons skilled in the art.

Examples, but not limited, of ditopic or multitopic ligands are described in WO2005035121, European patent 1 468 004, EP 08 290 747.

While the present invention describes a variety of transition metal complexes useful in catalyzing metathesis reactions, it should be noted that such complexes may be formed in situ. Accordingly, additional ligands may be added to a reaction solution as separate compounds, or may be complexed to the metal center to form a metal-ligand complex prior to introduction to the reaction.

Synthetic protocols for representative 1,1-substituted prop-2-yn-1-ol ligands, ditopic, multitopic ligands and the corresponding ruthenium alkylidene complexes are as follows. Other substituted prop-2-yn-1-ol, ditopic, multitopic ligands and their respective metal complexes may be derived analogously.

EXAMPLE 1

2-[(4-bromo-2,6-dimethylphenylimino)methyl]-4-nitrophenoxy (PCy$_3$)(3-2-methylphenyl-5-methyl-inden-1-ylidene)Ru(II)Cl (1F)

Synthesis of (PPh$_3$)$_2$Cl$_2$Ru(3-2-methylphenyl-5-methylinden-1-ylidene) (1D)

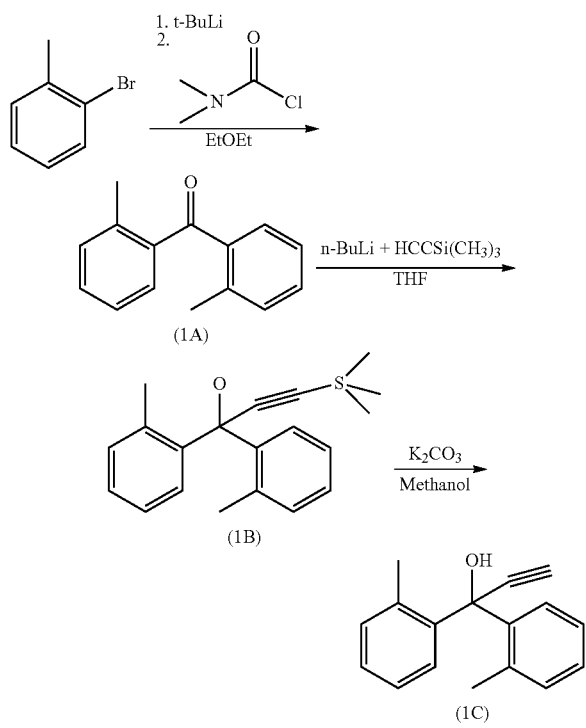

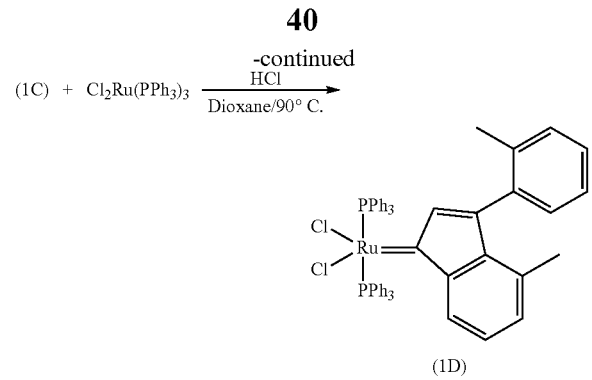

Step 1: Bis(2-methylphenyl)methanone (1A)

To a solution of 2-bromotoluene (2 eq., 2.6 ml, 21.79 mmol,) in 26 ml diethyl ether at −90° C., t-BuLi (1.9 M in pentane) (3 eq., 32.7 mmol, 17.2 ml.) was added drop wise. The solution was stirred for 30 min. at room temperature, followed by drop wise addition of N,N-dimethylcarbamoyl chloride (1 eq., 1 ml, 10.9 mmol), the reaction mixture was stirred for another 3 hours. The crude reaction mixture was quenched using 35 ml 1N HCl and diluted with diethyl ether. The organic phase was washed with water and the aqueous phase was extracted twice with diethyl ether, thereafter the ether fractions were combined and dried with anhydrous MgSO$_4$. Removal of MgSO$_4$ by filtration followed by purification using flash column chromatography (silica gel, hexane as solvent) and finally evaporation of the solvent and a white solid was obtained 0.93 g (40.6%).

$^1$H NMR (300 MHz, CDCl$_3$, TMS): δ 7.38 (td, 2H), 7.29 (td, 4H), 7.20 (td, 2H), 2.44 (s, 6H).

$^{13}$C NMR (75 MHz, CDCl$_3$): δ 200.79, 139.01, 138.17, 131.43, 131.07, 130.31, 125.42, 20.67.

Step 2: 1,1-bis-methylphenyl-3-(trimethylsilyl)prop-2-yn-1-ol (1B)

n-BuLi (2.5 M in hexanes) (1.5 eq., 5.7 ml, 14.28 mmol,) was added drop wise to stirred solution of trimethylsilylacetylene (1.5 eq., 2 ml, 14.28 mmol) in anhydrous THF (17 ml) at −90° C. under an argon atmosphere. After addition, the resulting solution was stirred for another 5 min in a cold bath followed by stirring for 30 minutes at room temperature. Thereafter, bis(2-methylphenyl)methanone (9.52 mmol, 2 g) in 17 ml dry THF was added slowly to the solution at −90° C. and the resulting mixture was allowed to heat up and refluxed for 30 min. The crude reaction mixture was quenched using 15 ml 1N HCl and diluted with diethyl ether. The organic phase was washed with water and the aqueous phase were combined and extracted twice with ether, thereafter the ether fractions were combined and dried with anhydrous MgSO$_4$. After removal of MgSO$_4$ by filtration, and evaporation of the solvent a yellow liquid was obtained in quantitative yield. The obtained product was used without further purification.

$^1$H NMR (300 MHz, CDCl$_3$, TMS): δ 7.95 (dd, 2H), 7.27 (dd, 4H), 7.15 (dd, 2H) 2.75 (s, 1H) 2.14 (s, 6H), 0.27 (d, 9H).

$^{13}$C NMR (75 MHz, CDCl$_3$): δ 141.01, 136.76, 132.37, 128.13, 127.45, 125.58, 107.10, 92.44, 75.01, 21.40, 0.00.

Step 3: 1,1-bis-2-methylphenyl-prop-2-yn-1-ol (1C)

A solution of 1,1-bis-methylphenyl-3-(trimethylsilyl)prop-2-yn-1-ol was obtained from previous step and K$_2$CO$_3$ (1 eq, 1.3 g 9.52 mmol) in dry methanol (10 ml) was stirred at room temperature for 3 h. The crude reaction mixture was quenched using 20 ml 1N HCl and diluted with diethyl ether. The organic phase was washed with water and the aqueous phase was extracted twice with diethyl ether, thereafter the ether fractions were combined and dried on anhydrous $MgSO_4$. Removal of $MgSO_4$ by filtration followed by purification using flash column chromatography (silica gel, Hexane/EtOAc=30/1) and finally evaporation of the solvent a yellowish solid (2.06 g, 92% yield for step 2+3) was obtained.

$^1$H NMR (300 MHz, $CDCl_3$, TMS): δ 7.95 (m, 2H), 7.23 (m, 4H), 7.09 (m, 2H) 2.89 (s, 1H) 2.67 (s, 1H), 2.02 (s, 6H).
$^{13}$C NMR (75 MHz, $CDCl_3$): δ 140.60, 136.33, 132.30, 128.19, 127.24, 125.58, 85.52, 76.80, 74.75, 21.16.
ESI[M-OH]: 219.1, calculated: 219.1.

Step 4: $(PPh_3)_2$ $Cl_2Ru$(3-2-methylphenyl-5-methyl-phenyl-inden-1-ylidene) (1D)

$(PPh_3)_3RuCl_2$ (1 eq., 0.575 g, 0.6 mmol) and 1,1-bis-2-methylphenyl-prop-2-yn-1-ol (compound C, 1.5 eq., 0.213 g, 0.9 mmol) were added in 4 ml HCl/dioxane solution (0.15 mol/l). The solution was heated to 90° C. for 3 hour, after which the solvent was removed under vacuum. Hexane (20 ml) was added to the flask and the solid was ultrasonically removed from the wall. The resulting suspension was filtered and washed two times using hexane (5 ml). The remaining solvent was evaporated affording a red-brown powder; 0.52 g (Yield: 95%). The product was characterized by NMR spectra $^1$H and $^{31}$P.

$^1$H NMR (300 MHz, $CDCl_3$, TMS): δ 7.56 (dd, 11 H), 7.37 (t, 6 H), 7.21-7.31 (m, 13 H), 7.09 (tetra, 3 H), 6.95 (t, 3 H), 6.47 (t, 1 H), 6.14 (s, 1 H), 2.20 (s, 3 H), 1.66 (s, 3 H).
$^{31}$P NMR (121.49 MHz, $CDCl_3$): δ 29.33.

Step 5: Synthesis of $(PCy_3)_2Cl_2Ru$(3-2-methylphenyl-5-methyl-inden-1-ylidene (1E)

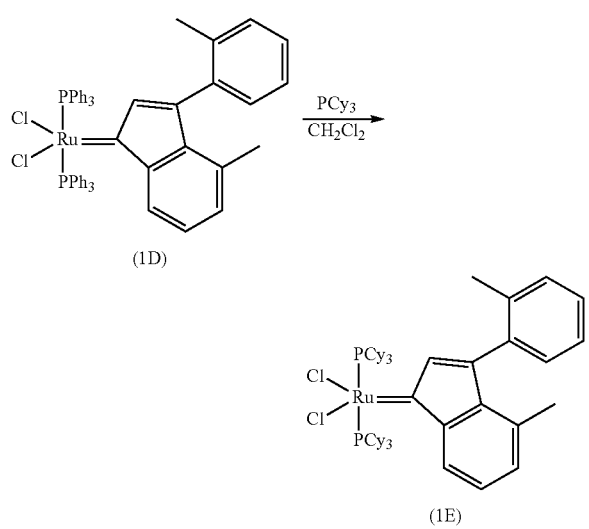

A 25 ml vial was charged with $(PPh_3)_2Cl_2Ru$(3-2-methylphenyl-5-methyl-inden-1-ylidene) (1 eq., 0.4574 g, 0.5 mmol), tricyclohexylphosphine (3 eq., 0.42 g, 1.5 mmol) and dichloromethane (10 ml). After completion of the reaction (1 h) the resulting slurry was dried under vacuum and 20 ml isopropanol was added. Filtration afforded a red-brown powder, which after washing with 5 ml isopropanol (2×) and drying under vacuum afforded 0.44 g of catalyst (Yield: 93%). The product was characterized by NMR spectra $^1$H and $^{31}$P.

$^1$H NMR (300 MHz, $CDCl_3$, TMS): δ 8.54 (d, 1 H), 7.24-7.29 (m, 1 H), 7.10-7.17 (m, 4 H), 7.07 (s, 1 H), 7.02 (d, 1 H), 2.61 (d, 6 H), 2.22 (s, 3 H), 1.18-1.96 (m, 63 H).
$^{31}$P NMR (121.49 MHz, $CDCl_3$): δ 31.75, 31.56.
Characteristic values of $^1$H and $^{31}$P: H—C8: 8.54 ppm (d, 1 H) and P: 31.75 and 31.56 ppm.

Step 6: Synthesis of 2-[(4-bromo-2,6-dimethylphenylimino)methyl]-4-nitrophenoxy $(PCy_3)$(3-2-methylphenyl-5-methyl-inden-1-ylidene)Ru(II)Cl (1F)

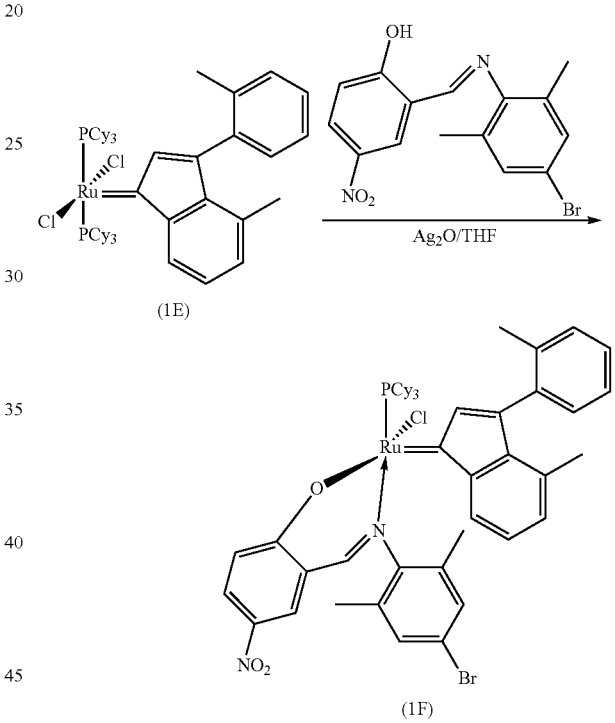

$(PCy_3)_2Cl_2Ru$(3-2-methylphenyl-5-methyl-inden-1-ylidene (0.53 mmol) and 2-[(4-bromo-2,6-dimethylphenylimino)methyl]-4-nitrophenol (0.53 mmol) (synthesized according the literature), silver(I) oxide (0.32 mmol) were added to a Schlenk flask under argon. Dry THF (20 mL) was transferred to the Schlenk flask and then heated (40° C.) and stirred for a period of 4 h followed by cooling to room temperature. The white precipitate of $PCy_3AgCl$ (byproduct) and excess of $AgO_2$ was removed by filtration. The filtrate was collected in a Schlenk flask and the solvent was removed by evaporation under reduced pressure.

The reaction mixture was investigated on $^1$H and $^{31}$P NMR, which revealed quantitative transformation to complex 1F.

Characteristic values of $^1$H and $^{31}$P: H—C8: 6.75 ppm (d, 1H) and P: 39.65 ppm.

The isolated solid residue was recrystallized from pentane to provide the catalyst. Yield after recrystallization: 75%.

EXAMPLE 2

Synthesis of (S-IMes)(2-[(2-methylphenylimino)methyl]-4-nitrophenoxy) (3-2-methylphenyl-5-methyl-inden-1-ylidene)Ru(II)Cl (2B)

Step 1: Synthesis of (S-IMes)(PCy₃)Cl₂Ru(3-2-methylphenyl-5-methyl-inden-1-ylidene) (2A)

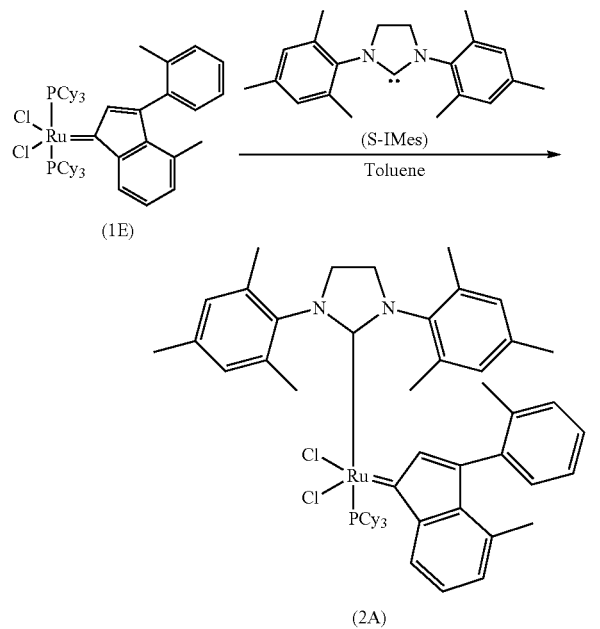

S-IMes=saturated 1,3-bis(mesityl)-imidazolidine-2-ylidene (1,3-Bis(2,4,6-trimethylphenyl)-2-imidazolidinylidene)

A 10 mL vial was charged with (PCy₃)₂Cl₂Ru(3-2-methylphenyl-5-methyl-inden-1-ylidene) (1 eq., 0.3804 g, 0.4 mmol) and 5-IMes (1.1 eq., 0.134 g, 0.44 mmol). Dry toluene (3 ml) was added under inert atmosphere. The mixture was vigorously stirred at 50° C. for 30 minutes and dried under vacuum followed by addition of 10 ml isopropanol. After filtration and washing (two times 5 ml isopropanol), an orange powder was obtained; 0.33 g (Yield: 84%). The product was characterized by NMR spectra $^1$H, $^{13}$C, and $^{31}$P.

$^1$H NMR (300 MHz, CDCl₃, TMS): δ 8.47 (d, 1 H), 7.44 (dd, 1 H), 7.20-7.28 (m, 2 H), 7.04-7.11 (m, 3 H), 6.99 (d, 1 H), 6.93 (s, 1 H), 6.88 (d, 1 H), 6.81 (s, 1 H), 6.05 (s, 1 H), 3.70-4.07 (m, 4 H), 2.74 (s, 3 H), 2.68 (s, 3 H), 2.38 (s, 3 H), 2.33 (s, 3 H), 2.14 (s, 3 H), 2.02 (s, 3 H), 1.87 (s, 3 H), 0.86-1.83 (m, 36 H).

$^{13}$C NMR (75 MHz, CDCl₃): δ 294.06, 293.96, 217.16, 216.19, 143.91, 140.11, 139.79, 139.52, 139.39, 138.77, 138.29, 136.94, 136.85, 136.27, 135.69, 134.04, 130.70, 130.01, 129.88, 129.57, 128.94, 128.58, 128.14, 127.25, 127.13, 126.27, 125.30, 125.05, 52.68, 52.64, 52.29, 52.26, 33.09, 32.87, 29.47, 29.24, 27.70, 27.57, 26.20, 21.18, 20.91, 20.32, 20.15, 19.36, 18.97, 18.92, 18.44.

$^{31}$P NMR (121.49 MHz, CDCl₃): δ 26.75.

Step 2: Synthesis of (S-IMes)(2-[(2-methylphenylimino)methyl]-4-nitrophenoxy)(3-2-methylphenyl-5-methyl-inden-1-ylidene)Ru(II)Cl (2B)

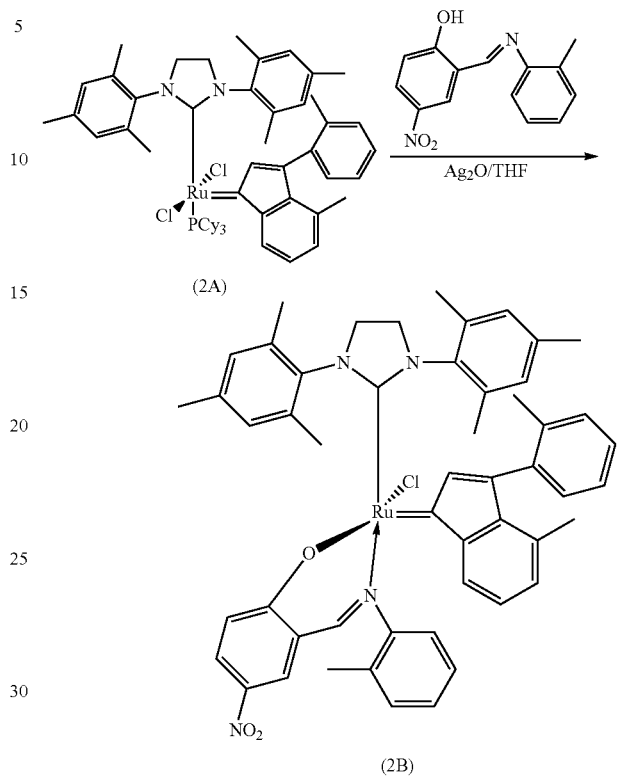

(Simes)(PCy₃)Cl₂Ru(3-2-methylphenyl-5-methylphenyl-inden-1-ylidene)(0.51 mmol) and 2-[(2-methylphenylimino)methyl]-4-nitrophenol (0.51 mmol) and silver(I) oxide (0.32 mmol) were added to a Schlenk flask under argon. Dry THF (20 mL) was transferred to the Schlenk flask and then heated (40° C.) and stirred for a period of 4 h followed by cooling to room temperature. The white precipitate of PCy₃AgCl (byproduct) and excess of AgO₂ was removed by filtration. The filtrate was collected in a Schlenk flask and the solvent was removed by evaporation under reduced pressure.

The reaction mixture was investigated on $^1$H and $^{31}$P NMR, which revealed quantitative transformation to complex 2B.

Characteristic values of $^1$H: H—C8: 8.39 ppm (d, 1H). (no $^{31}$P NMR peak present in the complex)

The isolated solid residue provided the catalyst in 85% yield.

EXAMPLE 3

(S-IMes)(2-[(2-chlorophenylimino)methyl]-4-nitrophenoxy) (3-2-methylphenyl-5-methyl-inden-1-ylidene)Ru(II)Cl (3A)

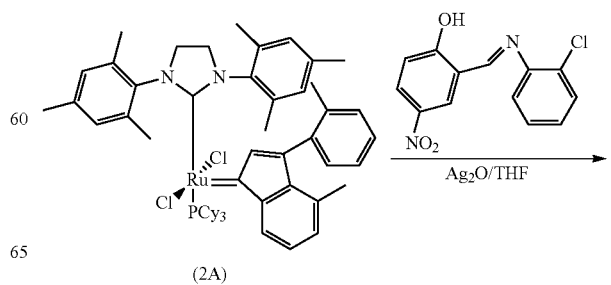

-continued

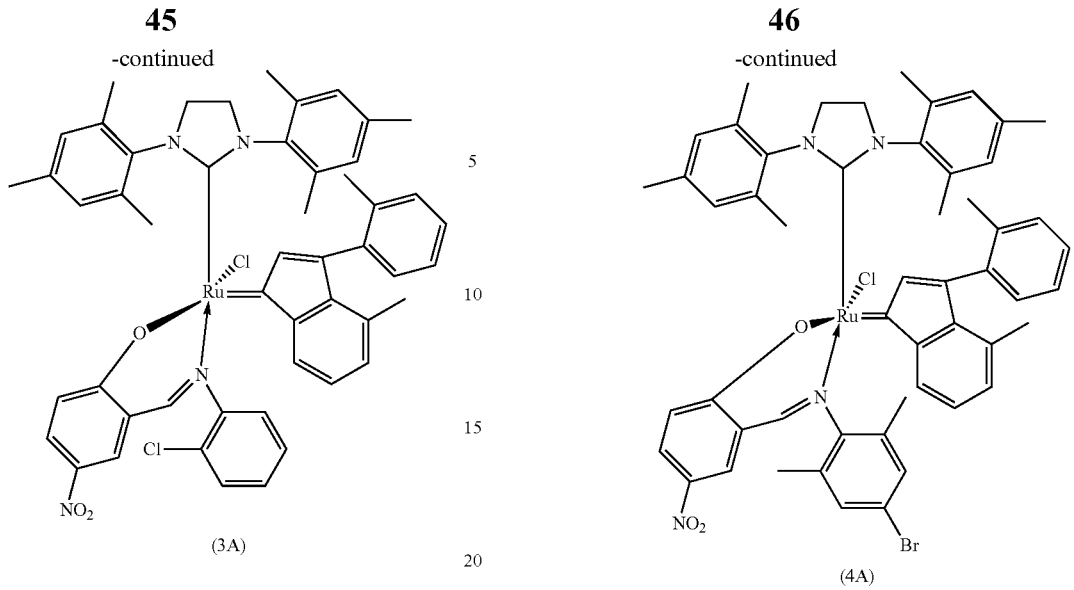

(3A)

(4A)

(Simes)(PCy$_3$)Cl$_2$Ru(3-2-methylphenyl-5-methylphenyl-inden-1-ylidene) (0.51 mmol) and 2-[(2-chlorophenylimino)methyl]-4-nitrophenol (0.51 mmol) and silver(I) oxide (0.32 mmol) were added to a Schlenk flask under argon. Dry THF (20 mL) was transferred to the Schlenk flask and then heated (40° C.) and stirred for a period of 4 h followed by cooling to room temperature. The white precipitate of PCy$_3$AgCl (byproduct) and excess of AgO$_2$ was removed by filtration. The filtrate was collected in a Schlenk flask and the solvent was removed by evaporation under reduced pressure.

The reaction mixture was investigated on $^1$H and $^{31}$P NMR, which revealed quantitative transformation to complex 3A.

Characteristic values of $^1$H: H—C8: 8.33 ppm (d, 1H). (no $^{31}$P NMR peak present in the complex)

The isolated solid residue provided the catalyst in 87% yield.

(Simes)(PCy$_3$)Cl$_2$Ru(3-2-methylphenyl-5-methyl-inden-1-ylidene (0.51 mmol) and 2-[(4-bromo-2,6-dimethylphenylimino)methyl]-4-nitrophenol (0.53 mmol) and silver(I) oxide (0.32 mmol) were added to a Schlenk flask under argon. Dry THF (20 mL) was transferred to the Schlenk flask and then heated (40° C.) and stirred for a period of 4 h followed by cooling to room temperature. The white precipitate of PCy$_3$AgCl (byproduct) and excess of AgO$_2$ was removed by filtration. The filtrate was collected in a Schlenk flask and the solvent was removed by evaporation under reduced pressure.

The reaction mixture was investigated on $^1$H and $^{31}$P NMR, which revealed quantitative transformation to complex 4A.

Characteristic values of $^1$H: H—C8: 8.45 ppm (d, 1H). (no $^{31}$P-NMR peak present in the complex)

The isolated solid residue provided the catalyst in 89% yield.

EXAMPLE 4

Synthesis of (S-IMes)(2-[(4-bromo-2,6-dimethylphenylimino)methyl]-4-nitrophenoxy) (3-2-methylphenyl-5-methyl-inden-1-ylidene)Ru(II)Cl (4A)

EXAMPLE 5

Synthesis of (S-IMes)(2-[(2,6-dimethylphenylimino)methyl]-4-nitrophenoxy) (3-2-methylphenyl-5-methyl-inden-1-ylidene)Ru(II)Cl (5A)

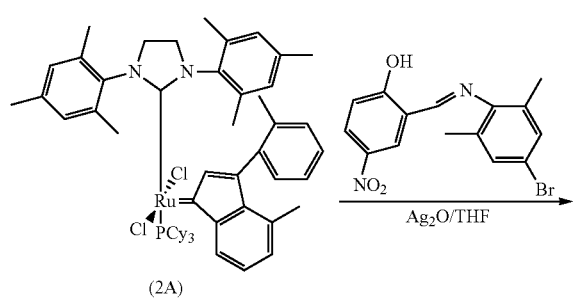

(2A)

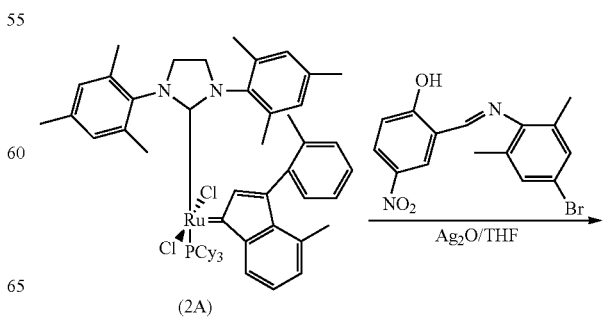

(2A)

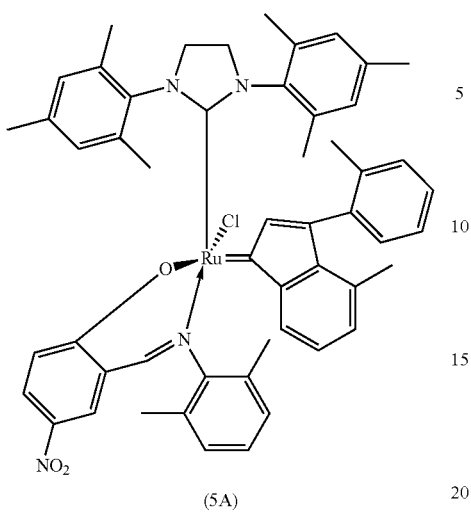

(5A)

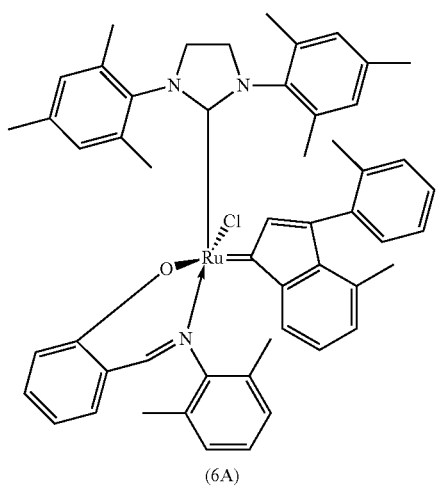

(6A)

(Simes)(PCy$_3$)Cl$_2$Ru(3-2-methylphenyl-5-methyl-inden-1-ylidene (0.51 mmol) and 2-[(2,6-dimethylphenylimino)methyl]-4-nitrophenol (0.53 mmol) and silver(I) oxide (0.32 mmol) were added to a Schlenk flask under argon. Dry THF (20 mL) was transferred to the Schlenk flask and then heated (40° C.) and stirred for a period of 4 h followed by cooling to room temperature. The white precipitate of PCy$_3$AgCl (byproduct) and excess of AgO$_2$ was removed by filtration. The filtrate was collected in a Schlenk flask and the solvent was removed by evaporation under reduced pressure.

The reaction mixture was investigated on $^1$H and $^{31}$P-NMR, which revealed quantitative transformation to complex 5A.

Characteristic values of $^1$H: H—C8: 8.87 ppm (d, 1H). (no $^{31}$P-NMR peak present in the complex)

The isolated solid residue provided the catalyst in 91% yield.

(Simes)(PCy$_3$)Cl$_2$Ru(3-2-methylphenyl-5-methyl-inden-1-ylidene (0.51 mmol) and 2-[(2,6-dimethylphenylimino)methyl]-phenol (0.53 mmol) and silver(I) oxide (0.32 mmol) were added to a Schlenk flask under argon. Dry THF (20 mL) was transferred to the Schlenk flask and then heated (40° C.) and stirred for a period of 4 h followed by cooling to room temperature. The white precipitate of PCy$_3$AgCl (byproduct) and excess of AgO$_2$ was removed by filtration. The filtrate was collected in a Schlenk flask and the solvent was removed by evaporation under reduced pressure.

The reaction mixture was investigated on $^1$H and $^{31}$P-NMR, which revealed quantitative transformation to complex X6A.

Characteristic values of $^1$H: H—C8: 9.10 ppm (d, 1 H). (no $^{31}$P-NMR peak present in the complex)

The isolated solid residue provided the catalyst in 91% yield.

EXAMPLE 6

Synthesis of (S-IMes)(2-[(2,6-dimethylphenylimino)methyl]phenoxy) (3-2-methylphenyl-5-methyl-inden-1-ylidene)Ru(II)Cl (6A)

EXAMPLE 7

Synthesis of (S-IMes)(2-[(2,6-dimethylphenylimino)methyl]-4-methoxyphenoxy) (3-2-methylphenyl-5-methyl-inden-1-ylidene)Ru(II)Cl (7A)

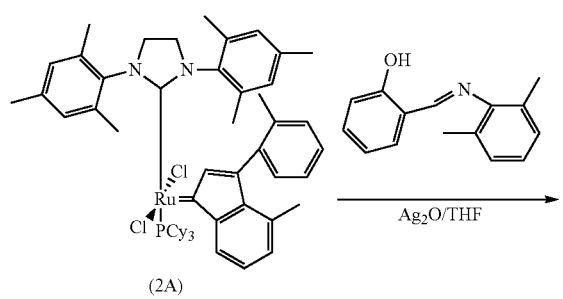

(2A)

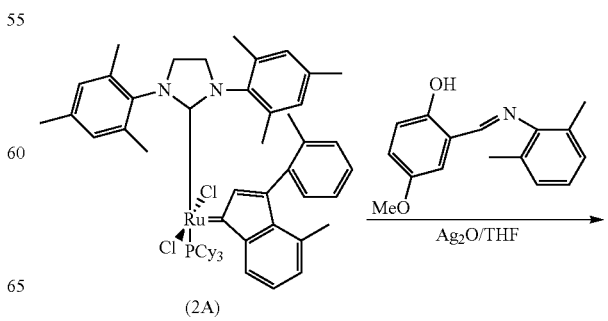

(2A)

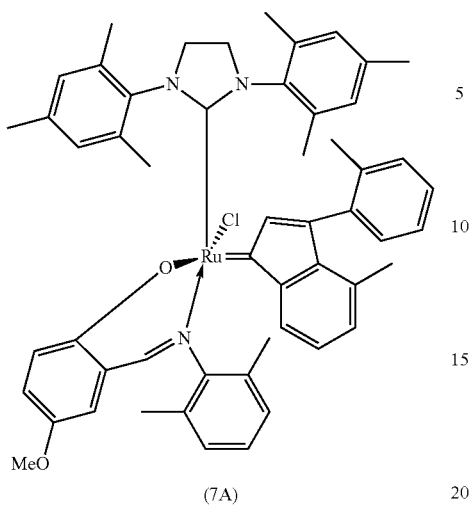

(7A)

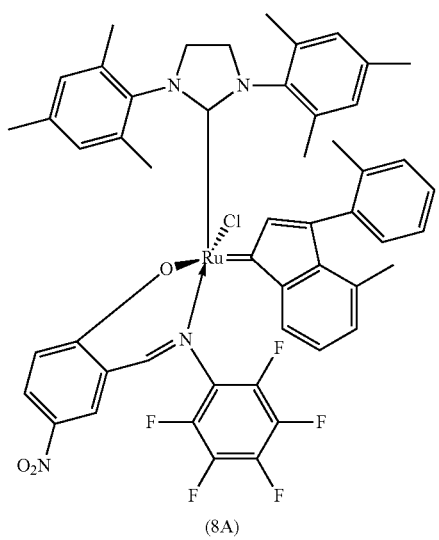

(8A)

(Simes)(PCy$_3$)Cl$_2$Ru(3-2-methylphenyl-5-methyl-inden-1-ylidene) (0.51 mmol) and 2-[(2,6-dimethylphenylimino)methyl]-4-methoxyphenol (0.53 mmol) and silver(I) oxide (0.32 mmol) were added to a Schlenk flask under argon. Dry THF (20 mL) was transferred to the Schlenk flask and then heated (40° C.) and stirred for a period of 4 h followed by cooling to room temperature. The white precipitate of PCy$_3$AgCl (byproduct) and excess of AgO$_2$ was removed by filtration. The filtrate was collected in a Schlenk flask and the solvent was removed by evaporation under reduced pressure.

The reaction mixture was investigated on $^1$H and $^{31}$P-NMR, which revealed quantitative transformation to complex 7A.

Characteristic values of $^1$H: H—C8: 9.15 ppm (d, 1H). (no $^{31}$P-NMR peak present in the complex)

The isolated solid residue provided the catalyst in 87% yield.

EXAMPLE 8

Synthesis of (S-IMes)(2-[(pentafluorophenylimino)methyl]-4-nitrophenoxy) (3-2-methylphenyl-5-methyl-inden-1-ylidene)Ru(II)Cl (8A)

(Simes)(PCy$_3$)Cl$_2$Ru(3-2-methylphenyl-5-methyl-inden-1-ylidene) (0.51 mmol) and 2-[pentafluorophenylimino)methyl]-4-nitrophenol (0.53 mmol) and silver(I) oxide (0.32 mmol) were added to a Schlenk flask under argon. Dry THF (20 mL) was transferred to the Schlenk flask and then heated (40° C.) and stirred for a period of 4 h followed by cooling to room temperature. The white precipitate of PCy$_3$AgCl (byproduct) and excess of AgO$_2$ was removed by filtration. The filtrate was collected in a Schlenk flask and the solvent was removed by evaporation under reduced pressure.

The reaction mixture was investigated on $^1$H and $^{31}$P-NMR, which revealed quantitative transformation to complex 8A.

Characteristic values of $^1$H: H—C8: 8.25 ppm (d, 1 H). (no $^{31}$P-NMR peak present in the complex)

The isolated solid residue provided the catalyst in 82% yield.

EXAMPLE 9

Synthesis of (S-IMes)(2-[(3s,5s,7s)-adamantan-1-ylimino methyl]-4-nitrophenoxy)(3-2-methylphenyl-5-methyl-inden-1-ylidene)Ru(II)Cl (9A)

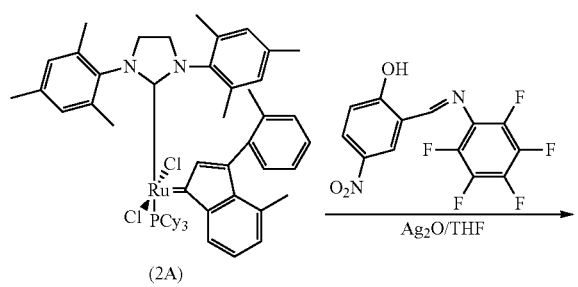

(2A)

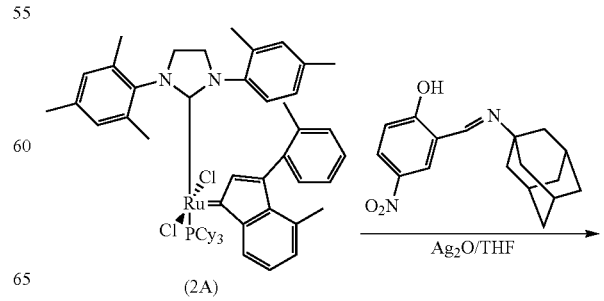

(2A)

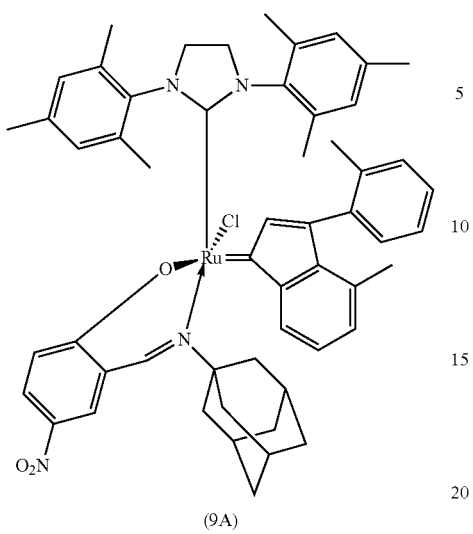

(9A)

(Simes)(PCy$_3$)Cl$_2$Ru(3-2-methylphenyl-5-methyl-inden-1-ylidene) (0.51 mmol) and 2-[(3s,5s,7s)-adamantan-1-yliminomethyl]-4-nitrophenol (0.51 mmol) and silver(I) oxide (0.31 mmol) were added to a Schlenk flask under argon. Dry THF (20 mL) was transferred to the Schlenk flask and then heated (40° C.) and stirred for a period of 4 h followed by cooling to room temperature. The white precipitate of PCy$_3$AgCl (byproduct) and excess of AgO$_2$ was removed by filtration. The filtrate was collected in a Schlenk flask and the solvent was removed by evaporation under reduced pressure.

The reaction mixture was investigated on $^1$H and $^{31}$P NMR, which revealed quantitative transformation to complex 9A.

Characteristic values of $^1$H: H—C8: 8.39 ppm (d, 1 H). (no $^{31}$P NMR peak present in the complex)

The isolated solid residue provided the catalyst in 84% yield.

EXAMPLE 10

Synthesis of (2-[(2-methylphenylimino)methyl]-4-nitrophenoxy) (3-2-methylphenyl-5-methyl-inden-1-ylidene)Ru(II)Cl (10D)

Synthesis of (PPh$_3$)$_2$Cl$_2$Ru(3-i-propyl-inden-1-ylidene) (10B)

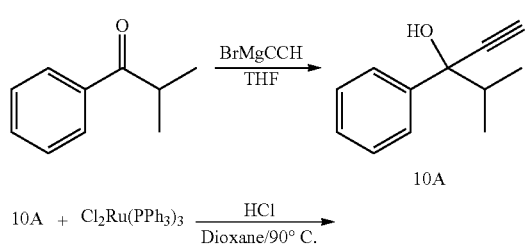

Step 1: 1-i-propyl-1-phenyl-prop-2-yn-1-ol (10A)

Ethynylmagnesium bromide (1.2 eq, 12.7 mmol, 25.4 ml) (0.5M in THF) was added to (i-propyl)(phenyl)methanone (1 eq., 10.6 mmol, 1.57 g) in dry THF (7 ml). The resulting solution was allowed to heat up under reflux overnight. The crude mixture was quenched by addition of 1N HCl (15 ml) and diluted with diethyl ether. The organic layer was separated; the aqueous layer was extracted twice with diethyl ether. The organic layers were combined dried on anhydrous MgSO$_4$, filtered, and concentrated under vacuum. The product obtained after column chromatography (Hexane: EtOAc 20:1) is a yellow liquid 1.75 g yield 95%.

$^1$H NMR (300 MHz, CDCl$_3$): δ 7.61 (dt, 2H), 7.22-7.36 (m, 3H), 2.66 (s, 1H), 2.50 (s, 1H), 2.09 (sept, 1H), 1.06 (d, 3H), 0.81 (d, 3H).

$^{13}$C NMR (75 MHz, CDCl$_3$): δ 143.42, 127.95, 127.74, 126.14, 85.03, 77.07, 74.99, 40.16, 17.90, 17.38.

Step 2: (PPh$_3$)$_2$Cl$_2$Ru(3-i-propyl-inden-1-ylidene) (10B)

(PPh$_3$)$_3$RuCl$_2$ (1 eq., 0.575 g, 0.6 mmol) and 1-(i-propyl)-1-phenylprop-2-yn-1-ol (compound 18A, 1.5 eq., 0.144 g, 0.9 mmol) were added in 4 ml HCl/dioxane solution (0.15 mol/1). The solution was heated to 90° C. for 3 hour, after which the solvent was removed under vacuum. Hexane (20 ml) was added to the flask and the solid was ultrasonically removed from the wall. The resulting suspension was filtered and washed two times using hexane (5 ml). The remaining solvent was evaporated affording a red-brown powder; 0.48 g (Yield: 93%). The product was characterized by NMR spectra $^{31}$P.

$^{31}$P NMR (121.49 MHz, CDCl$_3$): δ 29.55.

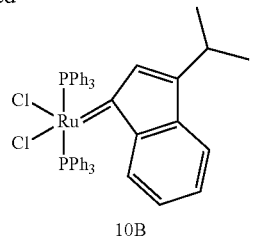

10B

Step 3: Synthesis of (PCy$_3$)$_2$Cl$_2$Ru(3-i-isopropyl-inden-1-ylidene) (10C)

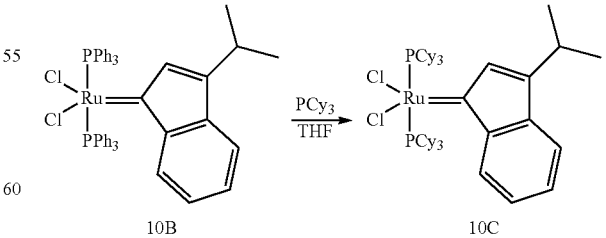

A 25 ml vial was charged with (PPh$_3$)$_2$Cl$_2$Ru(3-i-propyl-inden-1-ylidene) (1 eq., 0.4260 g, 0.5 mmol), tricyclohexylphosphine (3 eq., 0.42 g, 1.5 mmol) and dichloromethane (10 ml). After completion of the reaction (1 h) the resulting slurry was dried under vacuum and 20 ml isopropanol was added. Filtration afforded a red brown powder, which after washing with 5 ml isopropanol (2×) and drying under vacuum afforded 0.40 g of catalyst (Yield: 90%). The product was characterized by NMR spectra $^1$H and $^{31}$P.

Characteristic values of $^1$H and $^{31}$P: H—C8: 8.57 ppm (d, 1 H) and P: 31.44 ppm.

Step 4: Synthesis of (2-[(2-methylphenylimino) methyl]-4-nitrophenoxy)(3-2-methylphenyl-5-methyl-inden-1-ylidene)Ru(II)Cl (10D)

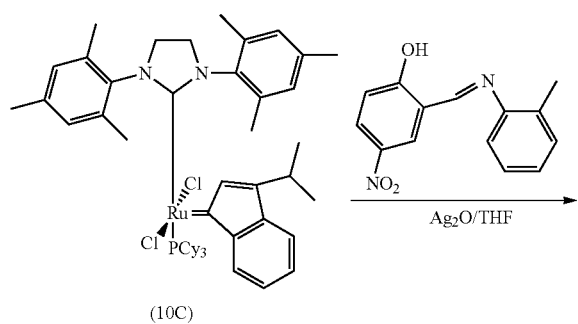

(10C)

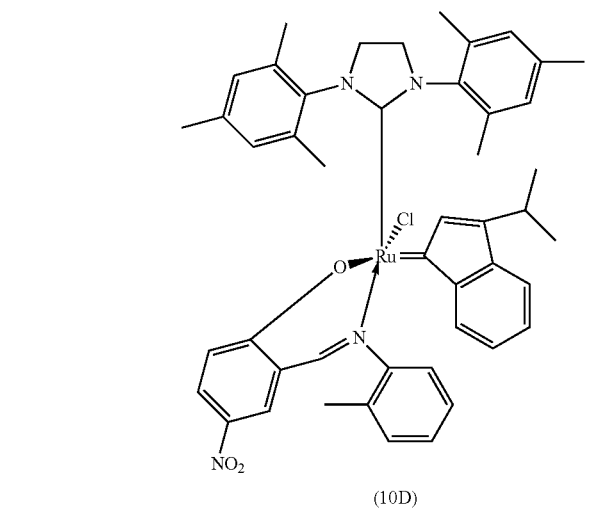

(10D)

(Simes)(PCy$_3$)Cl$_2$Ru(3-isopropyl-inden-1-ylidene) (0.50 g, 0.55 mmol) and 2-[(2-methylphenylimino)methyl]-4-nitrophenol (0.14 g, 0.55 mmol), and silver(I) oxide (0.33 mmol) were added to a Schlenk flask under argon. Dry THF (20 mL) was transferred to the Schlenk flask and then heated (40° C.) and stirred for a period of 4 h followed by cooling to room temperature. The white precipitate of PCy$_3$AgCl (byproduct) and excess of AgO$_2$ was removed by filtration. The filtrate was collected in a Schlenk flask and the solvent was removed by evaporation under reduced pressure.

The reaction mixture was investigated on $^1$H and $^{31}$P-NMR, which revealed quantitative transformation to complex 10D.

Characteristic values of $^1$H: H—C8: 8.29 ppm (d, 1 H). (no $^{31}$P-NMR peak present in the complex)

The isolated solid residue provided the catalyst in 84% yield.

EXAMPLE 11

Synthesis of (PCy$_3$)(2-[(1-imidazole-3-propylimino) methyl]-phenoxy) (3-2-methylphenyl-5-methyl-inden-1-ylidene)Ru(II)Cl (11B)

Step 1: Synthesis of (1-imidazole-3-propylimino)methyl-phenol (11A)

Salicylaldehyde (37.54 mmol, 4.00 mL), 1-(3-aminopropyl)imidazole (37.54 mmol, 4.50 mL) and 15 ml ethyl alcohol were added to a 100 ml flask and refluxed for 4 hours. The resulting yellow solution was cooled overnight, filtered and washed with cold ethanol (3×1 mL). Bright yellow crystals were isolated in 90% yield.

$^1$H NMR (300 MHz, CDCl$_3$) δ 13.09 (s, 1H), 8.25 (s, 1H), 7.39 35 (s, 1H), 7.26 (t, J=7.8 Hz, 1H), 7.18 (d, J=8.2 Hz, 1H), 7.01 (s, 1H), 6.93-6.79 (m, 3H), 4.00 (t, J=6.9 Hz, 2H), 3.48 (t, J=6.5 Hz, 2H), 2.12 (p, J=6.7 Hz, 2H). $^{13}$C NMR (75 MHz, CDCl$_3$) δ 166.10, 160.90, 137.11, 132.57, 131.42, 129.79, 118.99, 116.98, 40 77.48, 76.64, 55.86, 44.30, 31.78 MS (EI, 70 eV, rel. intensity): 229 (100, M$^+$).

Step 2: Synthesis of Synthesis of (PCy$_3$)(2-[(1-imidazole-3-propylimino)methyl]-phenoxy) (3-2-methylphenyl-5-methyl-inden-1-ylidene)Ru(II)Cl (11B)

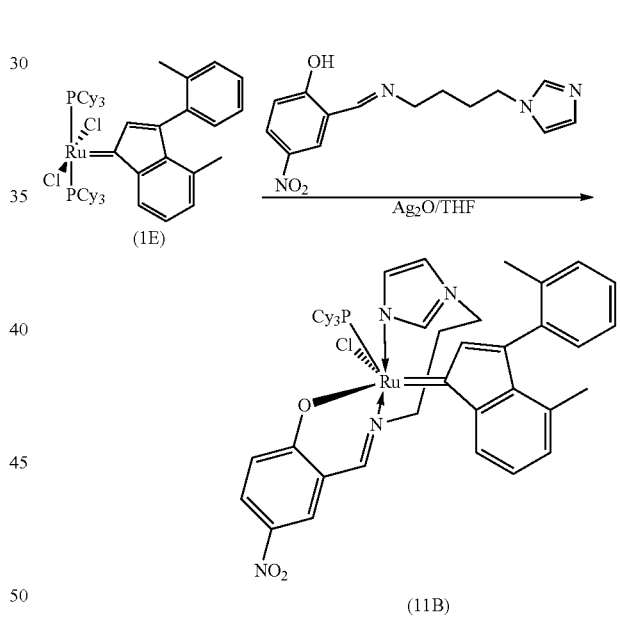

(11B)

(PCy$_3$)$_2$Cl$_2$Ru(3-2-methylphenyl-5-methyl-inden-1-ylidene (0.53 mmol) and (1-imidazole-3-propylimino) methyl-phenol (0.53 mmol), silver(I) oxide (0.32 mmol) were added to a Schlenk flask under argon. Dry THF (20 mL) was transferred to the Schlenk flask and then heated (50° C.) and stirred for a period of 4 h followed by cooling to room temperature. The white precipitate of PCy$_3$AgCl (byproduct) and excess of AgO$_2$ was removed by filtration. The filtrate was collected in a Schlenk flask and the solvent was removed by evaporation under reduced pressure.

The reaction mixture was investigated on $^1$H and $^{31}$P NMR, which revealed quantitative transformation to complex 11B.

Characteristic values of $^1$H and $^{31}$P: H—C8: 7.25 ppm (d, 1 H) and P: 36.95 ppm.

The isolated solid residue provided the catalyst in 75% yield.

EXAMPLE 12

Synthesis of (S-IMes)(2-[(2-methylphenylimino) methyl]phenoxy)$_2$(3-2-methylphenyl-5-methyl-inden-1-ylidene)Ru(II) (12)

Route A: Starting from (Simes)(PCy$_3$)Cl$_2$Ru(3-2-methylphenyl-5-methylphenyl-inden-1-ylidene) (2A)

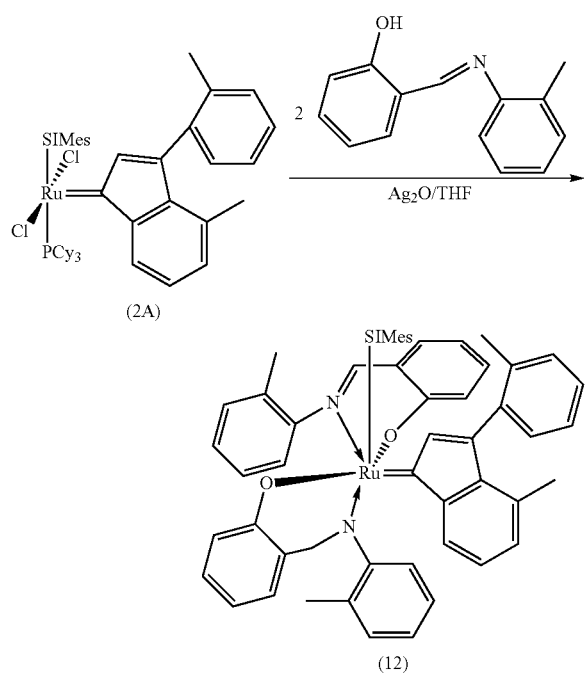

(2A)

(12)

(Simes)(PCy$_3$)Cl$_2$Ru(3-2-methylphenyl-5-methylphenyl-inden-1-ylidene) (0.51 mmol) and 2-[(2-methylphenylimino)methyl]phenol (1.1 mmol) and silver(I) oxide (0.65 mmol) were added to a Schlenk flask under argon. Dry THF (20 mL) was transferred to the Schlenk flask and then heated (40° C.) and stirred for a period of 5 h followed by cooling to room temperature. The white precipitate of PCy$_3$AgCl (byproduct) and excess of AgO$_2$ was removed by filtration. The filtrate was collected in a Schlenk flask and the solvent was removed by evaporation under reduced pressure. Addition of 2 mL CH$_2$Cl$_2$ and an excess of cold pentane precipitate the catalyst as a deep red powder, Yield: 85%.

The reaction mixture was investigated on $^1$H and $^{31}$P NMR, which revealed quantitative transformation to complex 12.

Characteristic values of $^1$H: H—C8: 8.11 ppm (d, 1 H). (no $^{31}$P NMR peak present in the complex)

Figure 2:
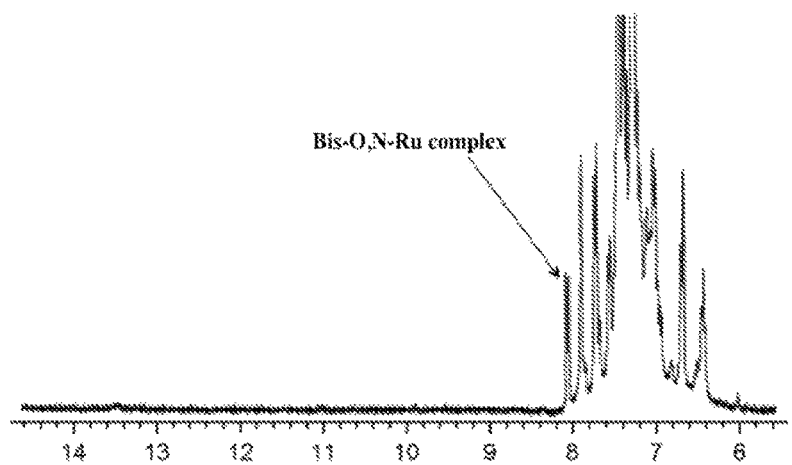
FIG. 2 is reaction progress after 5 h during the synthesis of catalyst 12.

The reaction progress has been monitored using H-NMR, in FIG. 1 the reaction progress after 1 h is displayed. It is clear that this is still a mixture of the starting Ru-precursor, the ditopic O,N-ligand, the mono O,N-ruthenium complex and the bis O,N-ruthenium complex. FIG. 2 is Reaction progress after 5 h confirming completion of the reaction.

Route B: Starting from (SIMes)(2-[(2-methylphenylimino)methyl]phenoxy) (3-2-methylphenyl-5-methyl-inden-1-ylidene)Ru(II)Cl

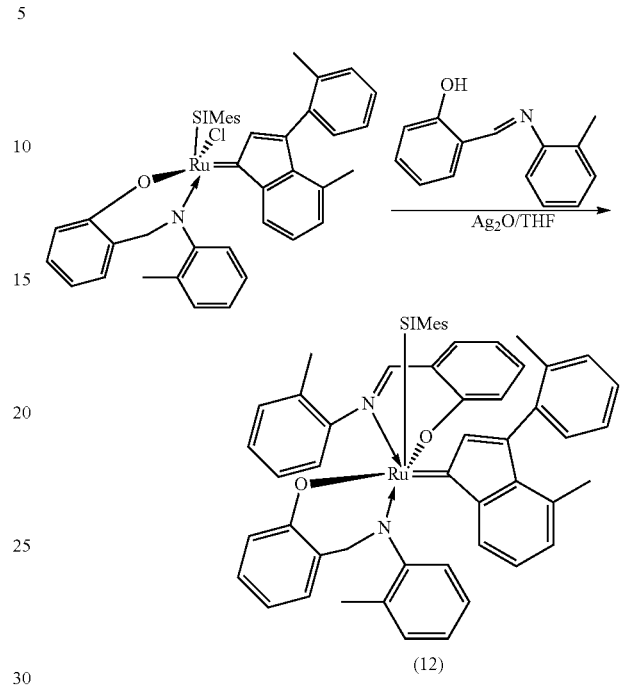

(12)

(SIMes)(2-[(2-methylphenylimino)methyl]phenoxy) (3-2-methylphenyl-5-methyl-inden-1-ylidene)Ru(II)Cl (0.51 mmol) and 2-[(2-methylphenylimino)methyl]phenol (0.52 mmol) and silver(I) oxide (0.32 mmol) were added to a Schlenk flask under argon. Dry THF (20 mL) was transferred to the Schlenk flask and then heated (40° C.) and stirred for a period of 5 h followed by cooling to room temperature. The white precipitate of PCy$_3$AgCl (byproduct) and excess of AgO$_2$ was removed by filtration. The filtrate was collected in a Schlenk flask and the solvent was removed by evaporation under reduced pressure. Addition of 2 mL CH$_2$Cl$_2$ and an excess of cold pentane precipitate the catalyst as a deep red powder, Yield: 85%.

The reaction mixture was investigated on $^1$H and $^{31}$P-NMR, which revealed quantitative transformation to complex 12.

Characteristic values of $^1$H: H—C8: 8.11 ppm (d, 1 H). (no $^{31}$P-NMR peak present in the complex)

Performance of the Catalysts of Present Invention

EXAMPLE 13

Comparison of Commercial Available Catalyst (N) with Catalyst of this Invention 5A, 6A and 7A for RCM of DEDAM Using Activation [a]

Figure 3:
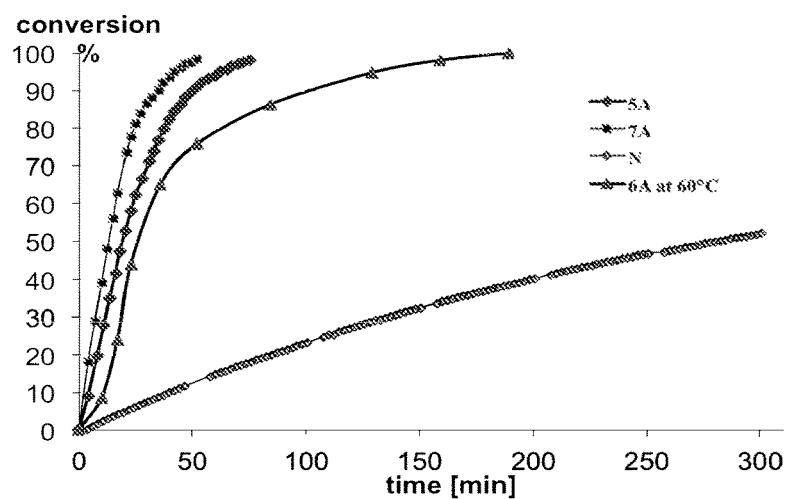
FIG. 3 is comparison between commercial catalyst N and 5A, 6A and 7A of this invention for the ring closing metathesis (RCM) of diethyldiallylmalonate (DEDAM) using activation.

FIG. 3 is comparison between commercial catalysts N and 5A, 6A and 7A for the ring-closing metathesis of diethyl-diallylmalonate (DEDAM) using activation ([a] using catalyst N and chemically activated 5A, 6A and 7A at 0.5 mol %, 20 eq of PhSiCl$_3$, substrate loading: 0.41 mmol DEDAM, temperature: 20° C., solvent: 0.60 mL CDCl$_3$, conversion determined by $^1$H NMR).

Upon chemical activation, complexes 6A and 7A significantly outperform the commercial complex N at ambient temperature.

EXAMPLE 14

Figure 4:
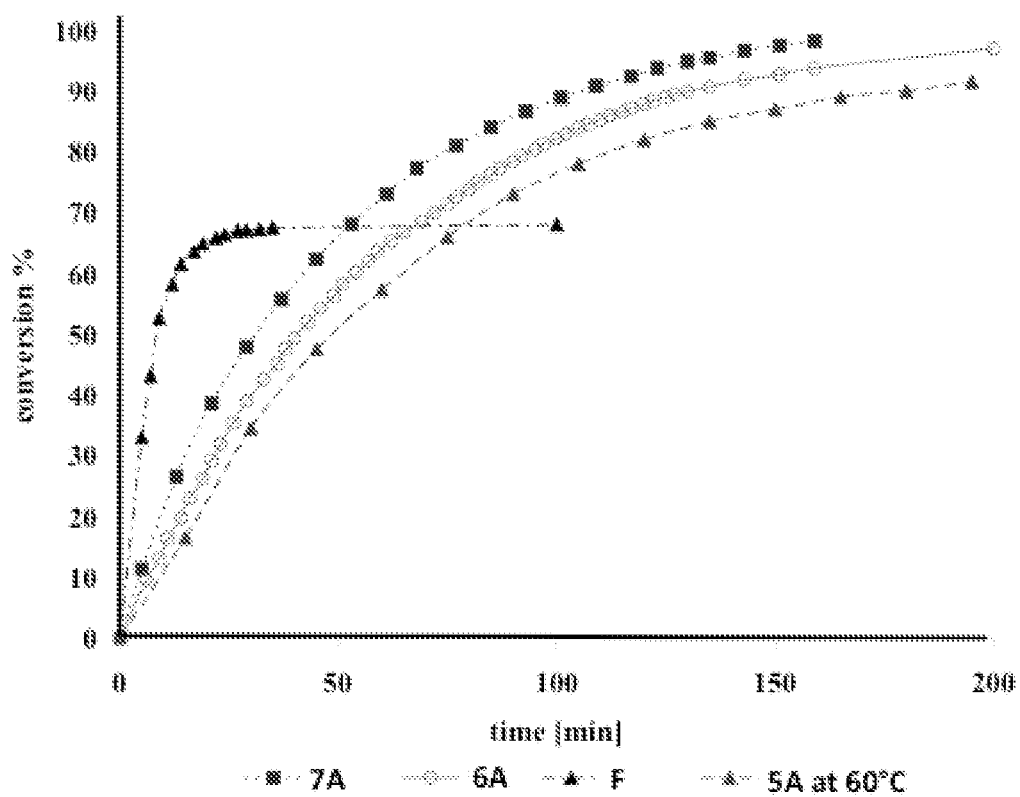
FIG. 4 is comparison between catalyst F and 5A-7A at a 0.1 mol % loading for the RCM of DEDAM.

Effect of Catalyst Loading, Comparison of Commercial Available Catalyst (N) with Newly Developed Catalyst 5A, 6A and 7A for RCM of DEDAM after Activation FIG. 4 is comparison between catalysts F and 5A-7A at a 0.1 mol % loading for the RCM of DEDAM ([a] using catalyst F and chemically activated 5A-7A at 0.1 mol %, 10 eq of PhSiCl$_3$, substrate loading: 0.41 mmol DEDAM, temperature: 20° C., solvent: 0.60 mL CDCl$_3$, conversion determined by $^1$H NMR).

At lower catalyst loadings, catalyst lifetime becomes increasingly important. All of the Schiff base-containing catalysts described herein, upon activation by PhSiCl$_3$, yield quantitative RCM of DEDAM at a catalyst loading of 0.1 mol % in CDCl$_3$, at room temperature with the exception of 5A which requires 60° C. In all cases, the performance of the salicylaldimine systems 5A-7A is superior to that of the commercial available complex F.

EXAMPLE 15

Comparison of Commercial Available Catalysts (N) with Newly Developed Catalyst for RCM of DEDAM in Protic Solvent MeOH at 50° C.

TABLE 1

Comparison of TON (Turn Over Number) of reported catalysts and catalyst of this invention

| Catalyst | TON[a] | Ref |
|---|---|---|
| 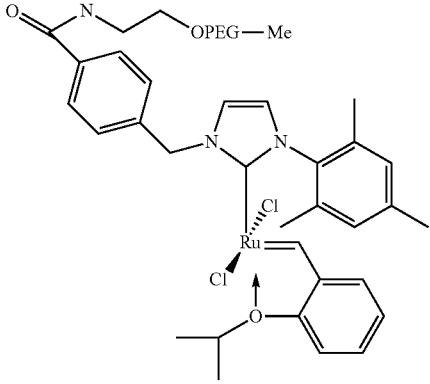 | 8 | Grubbs R. et al. Tetrahedron Letters 2005, 46, 2577-2580. |
| 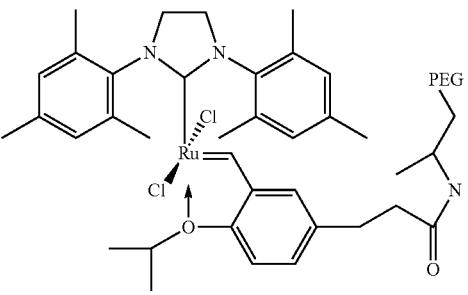 | 7 | Blechert S. et al. Bioorganic & Medicinal Chemistry Letters 2002, 12, 1873-1876. |
| 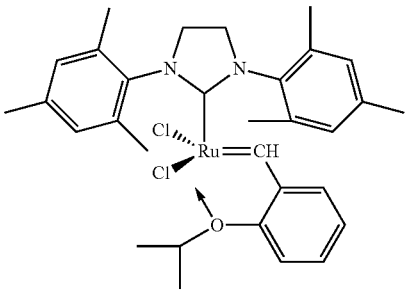 | 14 | Blechert S. et al. Bioorganic & Medicinal Chemistry Letters 2002, 12, 1873-1876. |

TABLE 1-continued

Comparison of TON (Turn Over Number) of reported catalysts and catalyst of this invention

| Catalyst | TON[a] | Ref |
|---|---|---|
| [structure with H₂IMES, Ru=CH-Ph, N⁺(CH₃)₃ Cl⁻, Br] | 19 | Raines R. et al. Advanced Synthesis & Catalysis 2007, 349, 395-404. |
| [Ru complex structure with mesityl imidazolidine, O₂N-phenoxide, adamantyl-N, biphenyl-indenylidene] | 60 | This invention |
| [Ru complex structure with mesityl imidazolidine, O₂N-phenoxide, pentafluorophenyl-N, biphenyl-indenylidene] | 189 | This invention |

TABLE 1-continued

Comparison of TON (Turn Over Number) of reported catalysts and catalyst of this invention

| Catalyst | TON[a] | Ref |
|---|---|---|
|  | 190 | This invention |

[a]TON = Turn over Number; RCM of DEDAM using 0.5 mol % catalyst in MeOH-$d_4$ at 50° C.

EXAMPLE 16

Comparison of Commercial Available Catalysts Catalyst of this Invention for RCM of DEDAM-2

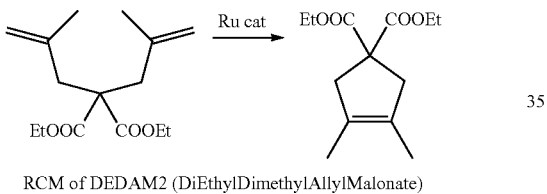

RCM of DEDAM2 (DiEthylDimethylAllylMalonate)

It is well known that DEDAM-2 is a difficult substrate to ring-close since it bears a methyl group on each double bond which introduce severe sterical hindering for the catalyst.

TABLE 2

Comparison of the catalysts for the reluctance substrate DEDAM-2

| Catalyst | Loading (mol %) | T (° C.) | TON[a,b] |
|---|---|---|---|
|  | 0.5 | 100 | 44 |

TABLE 2-continued
Comparison of the catalysts for the reluctance substrate DEDAM-2
| Catalyst | Loading (mol %) | T (° C.) | TON[a,b] |
|---|---|---|---|
| 4A | 0.5 | 100 | 136 |
| 13* | 0.5 | 100 | 110 |
| 14** | 0.5 | 100 | 37 |
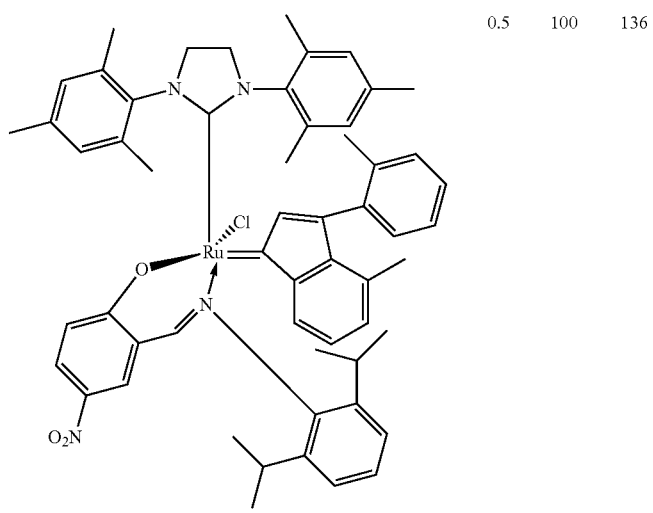
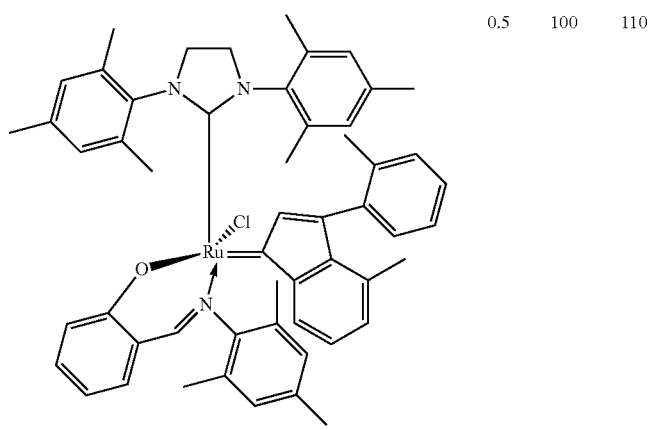
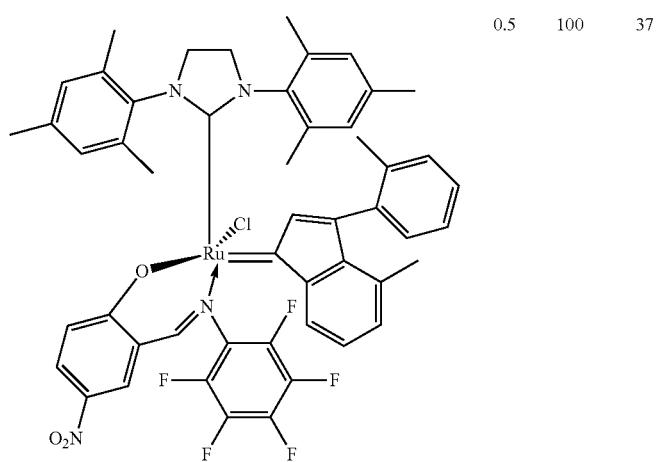

TABLE 2-continued

Comparison of the catalysts for the reluctance substrate DEDAM-2

| Catalyst | Loading (mol %) | T (° C.) | TON[a,b] |
|---|---|---|---|
| 8A H₂IMES / Cl—Ru=CH—Ph / Cl, PCy₃ | 5 | 100 | 7 |
| H₂IMES / Cl—Ru=CH—Ph / Cl, PCy₃ | 5 | 30 | 3[c] |
| Mod. H2 | 2.5 | 60 | 38[d] |

[a]Conversion obtained by ¹H NMR.
[b]Performed in toluene.
[c]Performed in CD₂Cl₂, data from ref. (*Organometallics* 2006, 25, 5740).
[d]Performed in C₆D₆, data from ref. (*Org. Lett.* 2007, 9, 1589).
*The catalyst has been prepared according to the description of 4A except that 2-[(2,6-diisopropylphenylimino)methyl]-4-nitrophenol was applied as ditopic ligand.
**The catalyst has been prepared according to the description of 4A except that 2-[(2,4,6-trimethylphenylimino)methyl]-phenol was applied as ditopic ligand.

The catalysts of this invention show 100% conversion at a 5 mol % loading. Decreasing the catalyst loading to 0.5 mol % leads to a TON of 136 for 13 and 110 for 14. These results outperform the previous highest TON of 38 for Mod. 112 (modified Hoveyda catalyst) and represent a 20-fold increase compared with the standard Grubbs 2$^{nd}$ generation catalyst. Therefore, 13 and 14 represent an excellent answer to 'a major challenge for the design of new more efficient catalysts'.

EXAMPLE 17

Influence of the Amount of Activator on the Performance of Catalyst 6A of this Invention for RCM of DEDAM

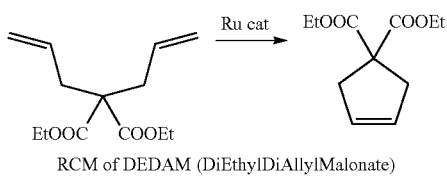 [SMILES: C=CCC(CC=C)(C(=O)OCC)C(=O)OCC ; CCOC(=O)C1(C(=O)OCC)CC=CC1]

RCM of DEDAM (DiEthylDiAllylMalonate)

Conditions: 0.5 mol % catalyst, variable eq of PhSiCl₃, substrate loading: 0.41 mmol DEDAM, temperature: 20° C., solvent: 0.60 mL CDCl₃, conversion determined by ¹H NMR.

Figure 5:
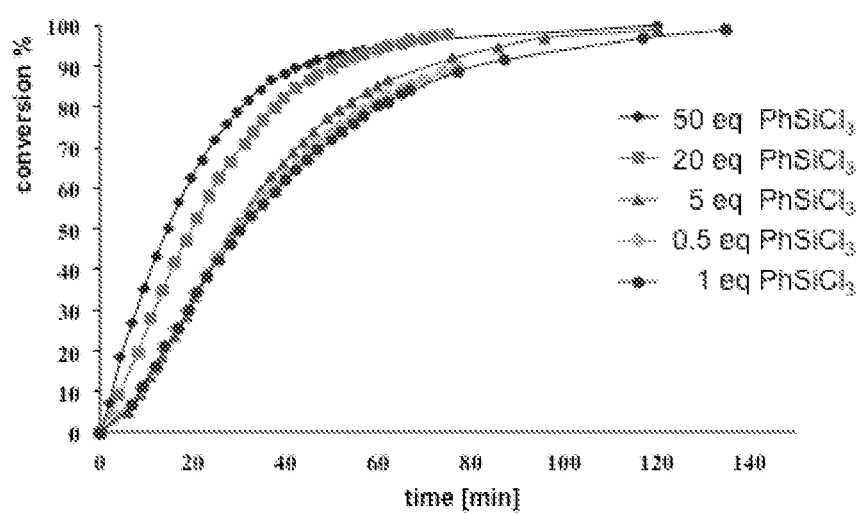
FIG. 5 is influence of activator amount on the catalytic performance for RCM of DEDAM.

FIG. 5 is influence of activator amount (from top to bottom the amount decreases from 50 eq. to 0.5 eq PhSiCl₃) on the catalytic performance for RCM of DEDAM.

It is clear that no longer an excess of activator is required to activate the catalysts of this invention and clearly outperforms the systems described in EP 1 577 282; EP 1 757 613. Moreover, an excess of activator is not immediately decomposing the catalyst demonstrating the robustness of the systems.

EXAMPLE 18

Monitoring Ring Opening Metathesis Polymerization (ROMP) of Dicyclopentadiene (DCPD)

The required amount was of catalyst was dissolved in a minimum amount of dichloromethane (CH₂Cl₂), and thereafter added to 80 g of DCPD which contains the required amount of activator (here PhSiCl₃ was used). The mixture was stirred and the polymerization reaction was monitored as a function of time starting at 20° C. by a thermocouple which was placed inside the reaction mixture to collect the temperature data. catalyst/DCPD: 1/60000.

The catalysts used are 4A, 8A, 9A and 12. For catalyst 4A and 8A the catalyst/activator=1/5 while for the 9A and 12 the catalyst/activator=1/0.5.

Figure 6:
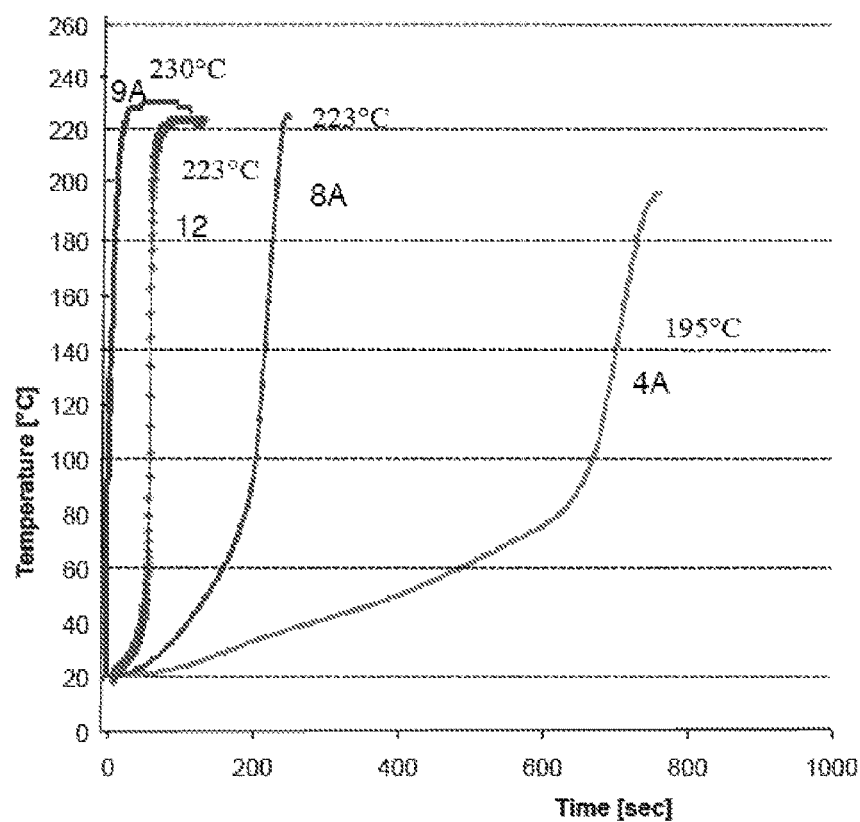
FIG. 6 is ROMP of DCPD using catalyst 4A, 8A, 9A and 12 of this invention.

FIG. 6 is ROMP of DCPD using catalyst 4A, 8A, 9A and 12 of this invention.

A ruthenium catalysts Verpoort (WO 03/062253) and Telene (WO 2011/009721 A1) comprising one and two bidentate Schiff base ligand respectively have been used as a reference catalyst; see table 3.

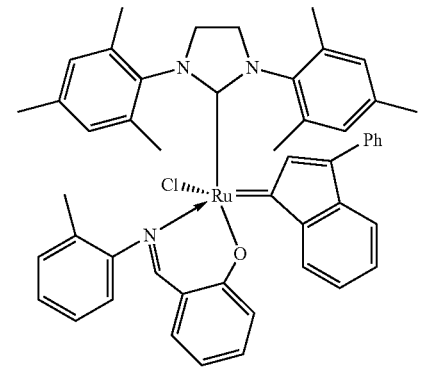

Verpoort (VP)

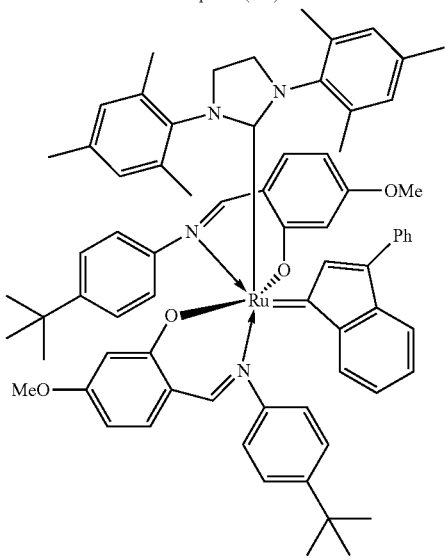

Telene (T)

It is clear that the catalysts of this invention outperform the catalysts described in WO 2011009721 and (WO 03/062253; Tetrahedron Lett., 2002, 43, 9101-9104; (b) J. Mol. Catal. A: Chem., 2006, 260, 221-226; (c) J. Organomet. Chem., 2006, 691, 5482-5486).

Introducing extra groups, substituents on the indenylidene part of the catalysts result in more steric strain in the molecule which promotes the initiation of the catalyst once it is activated.

TABLE 3

Comparison between existing catalyst (T and VP) and catalysts of this invention (4A, 8A, 9A and 12) for the ROMP of DCPD

| Catalyst | Latency | Cocatalyst | Cl/Ru | DCPD/Ru | $T_{max}$ (° C.) | $Tg_1$ (° C.) | $Tg_2$ (° C.) |
|---|---|---|---|---|---|---|---|
| 9A | fair | PhSiCl$_3$ | 0.5 | 50000 | 230 | 170 | 179 |
| 8A | Good | PhSiCl$_3$ | 5 | 50000 | 223 | 168 | 175 |
| 4A | Good | PhSiCl$_3$ | 5 | 50000 | 195 | 160 | 169 |
| 12 | Good | PhSiCl$_3$ | 0.5 | 50000 | 223 | 171 | 179 |
| T* | Good | PhSiCl$_3$ | 2 | 30000 | 217 | 171 | 178 |
| VP* | Good | PhSiCl$_3$ | 45 | 30000 | 215 | 156 | 169 |

*for reference only

All catalysts of this invention show an excellent latency towards DCPD (with 9A a fair latency), they are inactive at room temperature. All catalysts of this invention show an improved stability and are superior to other catalysts used as a reference (T and VP), see table 3.

Upon chemical activation, the catalyst of type I-I, e.g. 12 and 9A, according to the present invention, demonstrate an increased initiation compared to the reference catalyst (T and VP) because it requires only less than 1 equivalent of PhSiCl$_3$ to generate a highly active system. When the ROMP of DCPD is catalysed by the chemically activated VP complex (reference), under the same conditions (less than 1 equivalent of PhSiCl$_3$) a low catalytic activity was observed.

Moreover the ratio catalyst/monomer is increased with 66% compared to the reference catalysts (T and VP) which clearly stress out their superior performance of the catalysts of the present invention

EXAMPLE 19

Monitoring Ring Opening Metathesis Polymerization (ROMP) of Cyclo-Octadiene (COD)

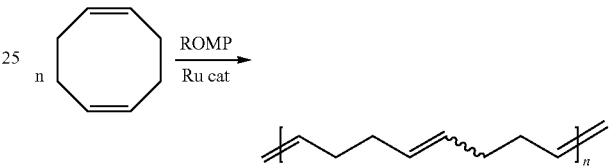

After charging an NMR tube with the appropriate amount of catalyst dissolved in deuterated solvent (CDCl$_3$), COD was added. The polymerization reaction was monitored as a function of time at 20° C. by integrating olefinic $^1$H-signals of the formed polymer (5.38-4.44 ppm) and the consumed monomer (5.58 ppm).

catalyst/COD: 1/3000, catalyst concentration: 0.452 mM.

TABLE 4

ROMP of COD (3000 equiv).

| Catalyst/PhSiCl$_3$ (equiv)$^a$ | T [° C.] | time [min] | Conv. [%] | cis [%]$^b$ | TOF (h$^{-1}$) |
|---|---|---|---|---|---|
| G2$^{[c]}$/0 | RT | 30 | 100 | 13 | 6 000 |
| F/0 | RT | 45 | 100 | 60 | 600$^{[d]}$ |
| N/0 | RT | 300 | 100 | 70 | 600 |
| VP/20 | RT | 10 | 100 | 9 | 18 000 |
| 6A/5 | RT | 5 | 100 | 5 | 36 000 |
| 7A/5 | RT | 5 | 100 | 20 | 36 000 |

$^a$Conditions: Catalyst concentration: 0.453 mM, solvent: CDCl$_3$, temperature: 20° C., conversion determined by $^1$H NMR.
$^b$Percent olefin with cis configuration in the polymer backbone; ratio based on data from $^1$H and $^{13}$C NMR spectra ($^{13}$C NMR spectroscopy: δ = 32.9 ppm allylic carbon trans; δ = 27.6 ppm allylic carbon cis).
$^{[c]}$see Nature 2007, 450, 243-251.].
$^{[d]}$monomer/catalyst = 300.

The catalysts of this invention are superior compared with other catalysts, the obtained TON is at least 2 times higher compared with catalyst VP and even 6 times higher or more compared with the other catalysts.

EXAMPLE 20

In-Situ Activation Using TiCl$_4$/iPrOH of Catalyst 4A for the ROMP of Dicyclopentadiene (DCPD)

This example demonstrates the possibility of in-situ activation of the catalysts of this invention. Here 40 g of DCPD in which TiCl$_4$ is present is mixed with 40 g of DCPD in which iPrOH and the catalyst are present. In the total DCPD mixture (80 g) a thermocouple is place to follow the temperature increase during the polymerization. From the plot it follows that all monomers are converted since a high temperature of 200° C. is reached. The ratio DCPD/catalyst/Lewis acid-alcohol=30000/1/10-10 and 30000/1/5-5.

Figure 7:
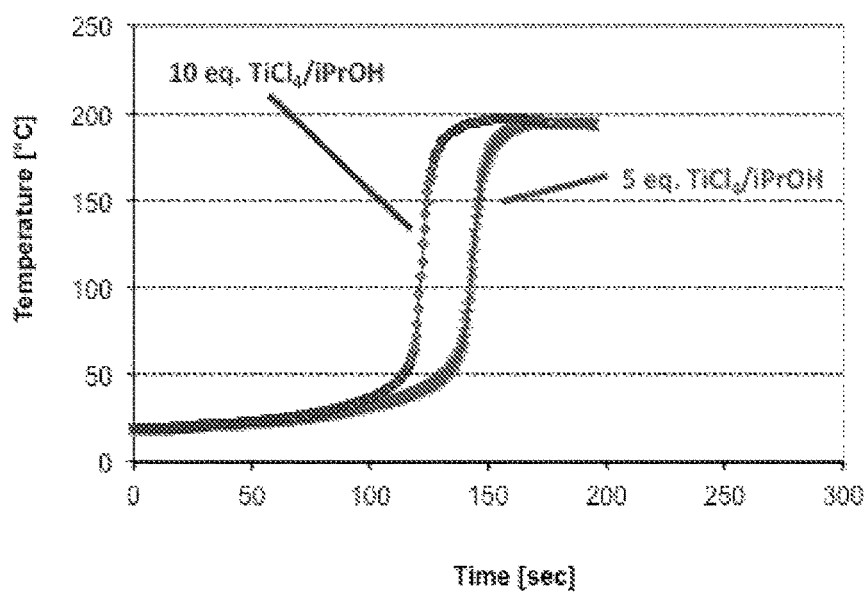
FIG. 7 is ROMP of DCPD using in-situ activation.

FIG. 7 is ROMP of DCPD using in-situ activation of catalyst 4A.

This excellent results confirms that all kinds of combinations between Lewis acids and RYH molecules can be used for in-situ activation of the catalysts of this invention as described in the description

EXAMPLE 21

Removal of the Residual Ruthenium (11B) from the Reaction Mixture

Subsequent to the RCM or cross-metathesis applications, in order to remove the residual ruthenium in final metathesis products, the reaction mixtures were passed through silica gel (3 g per 0.006 mmol of catalyst 11B) with different eluents (see Table 5). The silica gel can also be introduced directly into the reaction mixture. Complete decolorization was observed within 10 minutes of intense stirring. The ruthenium content of some selected metathesis products were determined by ICP-MS analysis. Using a basic filtration through silica gel, the ruthenium content of the products with an initial ruthenium content of 500 ppm were reduced to 1 ppm.

TABLE 5

Residual ruthenium from reaction mixtures after column chromatography.

| Entry | Product | Eluent | Ru content (ppm) |
|---|---|---|---|
| 1 | EtOOC COOEt (cyclopentene diester) | $CH_2Cl_2$ | 1 |
|   |   | Toluene | 1 |
| 2 | Self-metathesis product of methy-10-undecenoate | $CH_2Cl_2$ | 1 |
|   |   | Toluene | 3 |

EXAMPLE 22

Cross Metathesis of FAME (Fatty Acid Methyl Esters) Using Catalyst 4A 50 ml of a methyl ester mixture (consisting of 92.0% methyl oleate and 2.9% Methyl linoleate, percentages are based on a calibrated GC-Method) in the presence of 150 ppm of the catalyst (4A) is heated at 50° C. for 1 hour. After completion of the reaction 27% dimethyldiesters and 24% of 9-octadecene is obtained.

The invention claimed is:

1. A Group 8 transition metal catalyst having a general structure of formula (I) or (II):

wherein

M is a Group 8 transition metal;

$R^1$, $R^4$, $R^5$, and $R^6$ are hydrogen and $R^2$ and $R^3$ are identical or different and selected from phenyl, substituted phenyl, heteroatom-containing aryl, hydrocarbyl, substituted hydrocarbyl, or substituted heteroatom-containing hydrocarbyl;

wherein alternatively $R^2$ and $R^3$, including the ring carbon atoms to which they are attached, generate one or more cyclic structures, including aromatic structures;

$X^1$ represents an anionic ligand;

$L^1$ represents a neutral electron donor;

$A^1$ and $A^2$ are identical or different and are selected from the group consisting of oxygen, sulphur, selenium, NR"", PR"", and POR"";

E represents a donor atom selected from the group consisting of nitrogen, phosphorus, oxygen, sulphur, and selenium; wherein in case of oxygen, sulphur and selenium, R is omitted for double bonded E or R remains for a single bonded E;

wherein in case of Group 16 atoms, the bond between C and E is a single bond and a R' is bound to C;

$C^1$ and $C^2$ are carbon atoms linked to each other via a single or double bond wherein in case of a single bond each carbon atom bears an extra substituent $R^{C1}$ and $R^{C2}$;

R, R', R", R'" and R"" are identical or different and selected from H, hydrocarbyl, substituted hydrocarbyl, heteroatom containing hydrocarbyl, substituted heteroatom-containing hydrocarbyl, or a functional group;

wherein alternatively two directly adjacent radicals from the group of R, R', R", R'" and R"", including the atoms to which they are attached, generate one or more cyclic structures, including aromatic structures;

$R^{C1}$ and $R^{C2}$ are identical or different and are as defined for R', R", R'" and R"".

2. The catalyst according to claim 1, wherein M is Ru or Os.

3. The catalyst according to claim 1, wherein $L^1$ is selected from the group consisting of phosphine, sulphonated phosphine, phosphate, phosphinite, phosphonite, phosphite, arsine, stibine, ether, amine, amide, sulfoxide, carboxyl, nitrosyl, pyridine, substituted pyridine, pyrazine, thiocarbonyl, thioether, triazole carbene, N-heterocyclic carbene (NHC), substituted NHC, and a cyclic alkyl amino carbene.

4. The catalyst according to claim 1, wherein ligand $L^1$ represents a phosphine ligand having the formula $P(Q^1)_3$, wherein $Q^1$ are identical or different and are alkyl, cycloalkyl, cyclopentyl, cyclohexyl, neopentyl, aryl, $C_1$-$C_{10}$ alkyl-phosphabicyclononane, $C_3$-$C_{20}$ cycloalkyl phosphabicyclononane, a $C_6$-$C_{24}$ aryl or $C_1$-$C_{10}$-alkyl-phosphinite ligand, a $C_6$-$C_{24}$ aryl or $C_1$-$C_{10}$ alkyl phosphonite ligand, a $C_6$-$C_{24}$ aryl or $C_1$-$C_{10}$ alkyl phosphite-ligand, a $C_6$-$C_{24}$ aryl or $C_1$-$C_{10}$ alkyl arsine ligand, a $C_6$-$C_{24}$ aryl or $C_1$-$C_{10}$ alkyl amine ligand, a pyridine ligand, a $C_6$-$C_{24}$ aryl or $C_1$-$C_{10}$ alkyl-sulfoxide ligand, a $C_6$-$C_{24}$-aryl or $C_1$-$C_{10}$ alkyl ether ligand, or a $C_6$-$C_{24}$ aryl or $C_1$-$C_{10}$ alkyl amide ligand; or a sulfonated phosphine ligand of formula $P(Q^2)_3$, wherein $Q^2$ represents a mono- or poly-sulfonated $Q^1$-ligand.

5. The catalyst according to claim 1, wherein ligand $L^1$ represents a nitrogen-containing ligand selected from pyridine, picolines (α-, (β-, and γ-picoline), lutidines (2,3-, 2,4-, 2,5-, 2,6-, 3,4- and 3,5-lutidine), collidine (2,4,6-trimethylpyridine), trifluoromethylpyridine, phenylpyridine, 4-(dimethylamino) pyridine, chloropyridines (2-, 3- and 4-chloropyridine), bromopyridines (2-, 3- and 4-bromopyridine), nitropyridines (2-, 3- and 4-nitropyridine), bipyridine, picolylimine, gamma-pyran, phenanthroline, pyrimidine, bipyrimide, pyrazine, indole, coumarine, carbazole, pyrazole, pyrrole, imidazole, oxazole, thiazole, dithiazole, isoxazole, isothiazole, quinoline, bisquinoline, isoquinoline, bisisoquinoline, acridine, chromene, phenazine, phenoxazine, phenothiazine, triazine, thianthrene, purine benzimidazole, bisimidazole, bisoxazole pyrrole, imidazole or phenylimidazole.

6. The catalyst according to claim 4, wherein $Q^1$ is $C_1$-$C_{10}$ alkyl, $C_3$-$C_{20}$ cycloalkyl, or $C_6$-$C_{24}$ aryl.

7. The catalyst according to claim 1, wherein ligand $L^1$ represents a N-heterocyclic carbene (NHC) having a general structure of formula (IIIa) or (IIIb),

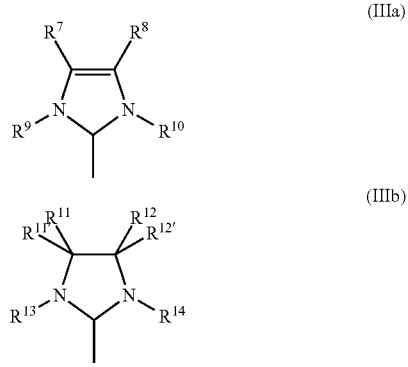

wherein
$R^7$-$R^{14}$, $R^{11'}$, $R^{12'}$ are identical or different and are hydrogen, straight or branched $C_1$-$C_{30}$ alkyl, $C_3$-$C_{20}$ cycloalkyl, $C_2$-$C_{20}$ alkenyl, $C_2$-$C_{20}$ alkynyl, $C_6$-$C_{24}$ aryl, $C_1$-$C_{20}$ carboxylate, $C_1$-$C_{20}$ alkoxy, $C_2$-$C_{20}$ alkenyloxy, $C_2$-$C_{20}$ alkynyloxy, $C_6$-$C_{20}$ aryloxy, $C_2$-$C_{20}$ alkoxycarbonyl, $C_1$-$C_{20}$ alkylthio, $C_6$-$C_{20}$ arylthio, $C_1$-$C_{20}$ alkylsulfonyl, $C_1$-$C_{20}$ alkyl sulfonate, $C_6$-$C_{20}$ aryl sulfonate or $C_1$-$C_{20}$ alkyl sulfinyl, one or more of the radicals $R^7$-$R^{14}$, $R^{11'}$, $R^{12'}$ may independently of one another be substituted by one or more substituents, straight or branched $C_1$-$C_{10}$ alkyl, $C_3$-$C_8$ cycloalkyl, $C_1$-$C_{10}$ alkoxy or $C_6$-$C_{24}$ aryl.

8. The catalyst according to claim 1, wherein ligand $L^1$ represents a cyclic alkyl amino carbene (CAAC) having a general structure of Formula (VI):

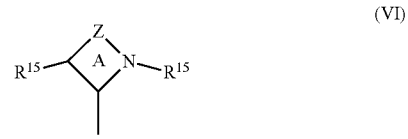

wherein the ring A is a 4-, 5-, 6-, or 7-membered ring, and Z is a linking group comprising from one to four linked vertex atoms selected from the group consisting of C, O, N, B, Al, P, S and Si with available valences occupied by hydrogen, oxo or R-substituents, wherein R is independently selected from the group consisting of $C_1$ to $C_{12}$ hydrocarbyl groups, substituted $C_1$ to $C_{12}$ hydrocarbyl groups, and halides, and each $R^{15}$ is independently a hydrocarbyl group or substituted hydrocarbyl group having 1 to 40 carbon atoms.

9. The catalyst according to claim 8, wherein $R^{15}$ is methyl, ethyl, propyl, isobutyl, n-butyl, pentyl, cyclopentyl, hexyl, cyclohexyl, octyl, cyclooctyl, nonyl, decyl, cyclodecyl, dodecyl, cyclododecyl, mesityl, adamantyl, phenyl, benzyl, toluyl, chlorophenyl, phenol, or substituted phenol.

10. The catalyst according to claim 1, wherein $X^1$ is selected from hydrogen, halogen, nitrate, pseudohalogen, straight-chain or branched $C_1$-$C_{30}$-alkyl, $C_6$-$C_{24}$ aryl, $C_1$-$C_{20}$ alkylthiol, $C_6$-$C_{24}$ arylthiol, $C_1$-$C_{20}$ alkoxy, $C_6$-$C_{24}$ aryloxy, $C_2$-$C_{24}$ alkoxycarbonyl, $C_6$-$C_{20}$ aryloxycarbonyl, $C_2$-$C_{20}$ acyl, $C_2$-$C_{20}$ acyloxy, $C_3$-$C_{20}$ alkyl diketonate, $C_6$-$C_{24}$ aryl diketonate, $C_1$-$C_{20}$ carboxylate, $C_1$-$C_{20}$ alkylsulfonato, $C_5$-$C_{20}$ arylsulfonato, $C_1$-$C_{20}$ alkylsulfanyl, $C_5$-$C_{20}$ arylsulfanyl, $C_1$-$C_{20}$ alkylsulfinyl, or $C_5$-$C_{20}$ arylsulfinyl.

11. The catalyst according to claim 1, wherein $X^1$ denotes fluoride, chloride, bromide, iodide, nitrate, benzoate, $C_1$-$C_5$ carboxylate, $C_1$-$C_5$ alkyl, phenoxy, $C_1$-$C_5$ alkoxy, $C_1$-$C_5$ alkylthiolate, $C_6$-$C_{24}$ alkylthiolate, $C_6$-$C_{24}$ aryl or $C_1$-$C_5$ alkyl sulfonate.

12. The catalyst according to claim 1, wherein $X^1$ is chloride, nitrate, $CF_3COO$, $CH_3COO$, $CFH_2COO$, $(CH_3)_3CO$, $(CF_3)_2(CH_3)CO$, $(CF_3)(CH_3)_2CO$, PhO (phenoxy), $C_6F_5O$ (pentafluorophenoxy), MeO (methoxy), EtO (ethoxy), p-$CH_3$-$C_6H_4$—$SO_3$(tosylate), $CH_3SO_3$(mesylate) or $CF_3SO_3$ (trifluoromethanesulfonate).

13. The catalyst according to claim 1, wherein R, R', R", R''' and R'''' are identical or different and represent hydrogen, halogen, hydroxyl, aldehyde, keto, thiol, $CF_3$, nitro, nitroso, cyano, thiocyano, isocyanates, carbodiimide, carbamate, thiocarbamate, dithiocarbamate, amino, amido, imino, ammonium, silyl, sulphonate (—$SO_3^-$), —$OSO_3^-$, —$PO_3^-$, —$OPO_3^-$, acyl, acyloxy, alkyl, cycloalkyl, alkenyl, cycloalkenyl, substituted alkenyl, heteroalkenyl, heteroatom-containing alkynyl, alkenylene, alkynyl, substituted alkynyl, aryl, substituted aryl, heteroaryl, carboxylate, alkoxy, alkenyloxy, alkynyloxy, aryloxy, alkaryl, aralkyl, alkaryloxy, aralkyloxy, alkoxycarbonyl, alkylamino-, alkylthio-, arylthio, alkylsulfonyl, alkylsulfinyl, dialkylamino, alkylammonium, alkylsilyl or alkoxysilyl, and
wherein alternatively two directly adjacent radicals selected from the group consisting of R, R', R", R''' and R'''', including the atoms to which they are attached, generate one or more cyclic structures, including aromatic structures.

14. A supported catalyst comprising the catalyst according to claim 1 and a support.

15. The supported catalyst according to claim 14 wherein the support is selected from the group consisting of porous inorganic solids, amorphous or paracrystalline materials, crystalline molecular sieves, modified layered materials, inorganic oxides, organic polymers, carbon, carbon nanotubes, graphene, metal organic frameworks, cross-linked, reticular polymeric resins, functionalized cross-linked polystyrenes, and chloromethyl-functionalized cross-linked polystyrenes and wherein the catalyst is deposited onto the support by impregnation, ion-exchange, deposition-precipitation, π-π interactions and vapor deposition; alternatively, the catalyst is chemically bound to the support via one or more covalent bonds.

16. A method for making a Group 8 transition metal catalyst having a general structure of formula (I) or (II) according to claim 1, comprising contacting a precursor compound of the formula $(X^1X^2ML_3)$ or $(X^1X^2ML_4)$ with an acetylenic compound, and at least one ditopic or multitopic ligand;

wherein for the precursor compound,

M is a Group 8 transition metal;

$X^1$ and $X^2$ are identical or different and represent an anionic ligand; and $L_3$ and $L_4$ represent a neutral electron donor ligand.

17. The method according to claim 16, wherein the acetylenic compound is represented by general formula (IX)

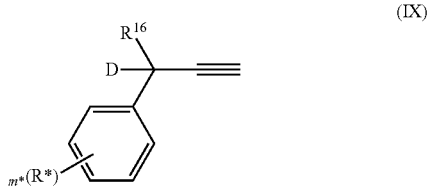

(IX)

wherein

D is a leaving group and selected from hydroxyl, halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethane-sulfonate $R^{16}$ is selected from hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, and wherein when $R^{16}$ is aryl, or heteroaryl, $R^{16}$ is substituted with any combination of $R^1$, $R^2$, $R^3$, $R^4$, $R^5$, and $R^6$ and may be linked with any of $R^1$, $R^2$, $R^3$, $R^4$, $R^5$, and $R^6$ to form one or more cyclic aromatic or non-aromatic groups;

m* is an integer from 1 to 5;

R* represents hydrogen, halogen, hydroxyl, aldehyde, keto, thiol, $CF_3$, nitro, nitroso, cyano, thiocyano, isocyanates, carbodiimide, carbamate, thiocarbamate, dithiocarbamate, amino, amido, imino, ammonium, silyl, sulphonate ($-SO_3^-$), $-OSO_3^-$, $-PO_3^-$, or $-OPO_3^-$, acyl, acyloxy, alkyl, cycloalkyl, alkenyl, cycloalkenyl, substituted alkenyl, heteroalkenyl, heteroatom-containing alkynyl, alkenylene, alkynyl, substituted alkynyl, aryl, substituted aryl, heteroaryl, carboxylate, alkoxy, alkenyloxy, alkynyloxy, aryloxy, alkaryl, aralkyl, alkaryloxy, aralkyloxy, alkoxycarbonyl, alkylamino, alkylthio, arylthio, alkylsulfonyl, alkylsulfinyl, dialkylamino, alkylammonium, alkylsilyl or alkoxysilyl, wherein alternatively two directly adjacent radicals selected from the group consisting of R, R', R", R''' and R'''', including the atoms to which they are attached, generating one or more cyclic structures, including aromatic structures.

18. The method according to claim 16, wherein the method comprises a first step of:

contacting $X^1X^2ML_3$ or $X^1X^2ML_4$ and the acetylenic compound in a molar ratio between 1 to 20 and adding to a mixture of acid/solvent; heating the mixture between 40° C. and 200° C. for a time less than 10 hours; removing the solvent and adding a non-polar solvent; filtering and washing the resulting precipitate using the same non-polar solvent; and obtaining, after drying, a modified indenylidene complex; and a second step of:

treating a solution of the ditopic or multitopic ligand in a suitable solvent with non-chelating modified indenylidene complex in a molar ratio and adding an amount of silver for a time sufficient to effectuate ligand exchange, at a temperature between ambient and 80° C. to yield a modified indenylidene catalyst compound; then lowering a reaction temperature to room temperature, removing by-product and excess of silver by filtration and concentrating a filtrate under reduced pressure; isolating a solid residue, and providing the Group 8 transition metal catalyst having general structure of formula (I) or (II).

19. A method for making a Group 8 transition metal catalyst having a general structure of formula (I) or (II) according to claim 1, comprising a first step of:

contacting $X^1X^2ML_3$ or $X^1X^2ML_4$ and an acetylenic compound in a molar ratio between 1 to 20 in a mixture of acid/solvent; heating the mixture between 40° C. and 200° C. for a time less than 10 hours; removing the solvent and adding a non-polar solvent; filtering and washing the resulting precipitate using the same non-polar solvent; and obtaining, after drying, a modified indenylidene complex; wherein $X^1$ and $X^2$ are identical or different and represent an anionic ligand and $L_3$ and $L_4$ represent a neutral electron donor ligand; wherein the modified indenylidene complex is a first generation compound or a second generation compound produced by mixing the first generation compound and a N-heterocyclic carbene (NHC) ligand or a cyclic alkyl amino carbene (CAAC) ligand in a suitable solvent for a time sufficient to effectuate ligand exchange, or a third generation compound produced by mixing the second generation compound and pyridine as solvent, for a time sufficient to effectuate phosphine ligand exchange; and a second step of:

treating a solution of a ditopic or multitopic ligand in a suitable solvent with the modified indenylidene complex in a required molar ratio and adding a required amount of silver for a time sufficient to effectuate ligand exchange, at a suitable temperature between ambient and 80° C. to yield a modified indenylidene catalyst compound; then lowering the reaction temperature to room temperature, removing by-product and excess of silver by filtration and concentrating a filtrate under reduced pressure; isolating a solid residue and providing the Group 8 transition metal catalyst having a general structure of formula (I) or (II), wherein the NHC ligand has a general structure of formula (IIIa) or (IIIb),

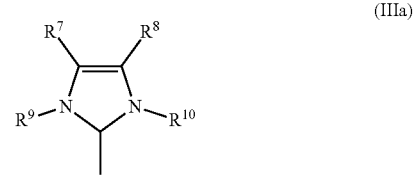

(IIIa)

-continued

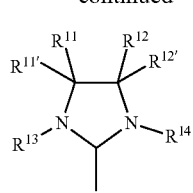

(IIIb)

wherein
$R^7$-$R^{14}$, $R^{11'}$, $R^{12'}$ are identical or different and are hydrogen, straight or branched $C_1$-$C_{30}$ alkyl, $C_3$-$C_{20}$ cycloalkyl, $C_2$-$C_{20}$ alkenyl, $C_2$-$C_{20}$ alkynyl, $C_6$-$C_{24}$ aryl, $C_1$-$C_{20}$ carboxylate, $C_1$-$C_{20}$ alkoxy, $C_2$-$C_{20}$ alkenyloxy, $C_2$-$C_{20}$, alkynyloxy, $C_6$-$C_{20}$ aryloxy, $C_2$-$C_{20}$ alkoxycarbonyl, $C_1$-$C_{20}$ alkylthio, $C_6$-$C_{20}$ arylthio, $C_1$-$C_{20}$ alkylsulfonyl, $C_1$-$C_{20}$ alkyl sulfonate, $C_6$-$C_{20}$ aryl sulfonate or $C_1$-$C_{20}$ alkyl sulfinyl, and one or more of the radicals $R^7$-$R^{14}$, $R^{11'}$, $R^{12'}$ may independently of one another be substituted by one or more substituents, straight or branched $C_1$-$C_{10}$ alkyl, $C_3$-$C_8$ cycloalkyl, $C_1$-$C_{10}$ alkoxy or $C_6$-$C_{24}$ ary; and
wherein the CAAC ligand has a general structure of Formula (VI):

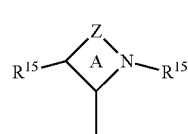

(VI)

wherein the ring A is a 4-, 5-, 6-, or 7-membered ring, and Z is a linking group comprising from one to four linked vertex atoms selected from the group consisting of C, O, N, B, Al, P, S and Si with available valences occupied by hydrogen, oxo or R-substituents, wherein R is independently selected from the group consisting of $C_1$ to $C_{12}$ hydrocarbyl groups, substituted $C_1$ to $C_{12}$ hydrocarbyl groups, and halides, and each $R^{15}$ is independently a hydrocarbyl group or substituted hydrocarbyl group having 1 to 40 carbon atoms.

20. The method according to claim 19, wherein the molar ratio of $X^1X^2ML_3$ or $X^1X^2ML_4$ and the acetylenic compound is between 1 to 15.

21. The method according to claim 20, wherein the molar ratio of $X^1X^2ML_3$ or $X^1X^2ML_4$ and the acetylenic compound is between 1 to 10.

22. The method according to claim 19, wherein the acid of acid/solvent in the first step is a Brønsted or a Lewis acid; an acid concentration in the solvent is lower than 5 mol/L.

23. The method according to claim 22, wherein the Brønsted acid is HF, HCl, HBr, or HI.

24. The method according to claim 19, comprising heating the mixture between 50° C. and 150° C. in the first step.

25. An activation method comprising:
bringing the catalyst according to claim 1 into contact with an activator under conditions such that said activator is able to at least partly cleave a bond between the transition metal and at least one ditopic/multitopic ligand of the catalyst.

26. The method according to claim 25, wherein the activator is selected from Brønsted acids.

27. The method according to claim 26, wherein the Brønsted acid is selected from the group consisting of HCl, HBr, $H_2SO_4$, $CH_3COOH$, and sulphonic acid resins.

28. The method according to claim 25, wherein the activator is a Lewis acid selected from the group consisting of:
$M^a$(I) halides,
compounds represented by the formula $M^aX_{2-y}R^a_y$ ($0 \leq y \leq 2$),
compounds represented by the formula $M^aX_{3-y}R^a_y$ ($0 \leq y \leq 3$);
compounds represented by the formula $M^aX_{4-y}R^a_y$ ($0 \leq y \leq 4$);
compounds represented by the formula $M^aX_{5-y}R^a_y$ ($0 \leq y \leq 5$);
compounds represented by the formula $M^aX_{6-y}R^a_y$ ($0 \leq y \leq 6$);
wherein
$R^a$ represents alkyl, cycloalkyl, alkenyl, cycloalkenyl, substituted alkenyl, heteroalkenyl, heteroatom-containing alkynyl, alkenylene, alkynyl, substituted alkynyl, aryl, substituted aryl, heteroaryl, carboxylate, alkoxy, alkenyloxy, alkynyloxy, aryloxy, alkaryl, aralkyl, alkaryloxy, aralkyloxy, alkoxycarbonyl, alkylamino-, alkylthio-, arylthio, alkylsulfonyl, alkylsulfinyl, dialkylamino, alkylammonium, alkylsilyl or alkoxysilyl,
X is an atom of the halogen group and is identical or different in the case where more than one halogen atom is present, and
$M^a$ is an atom having an atomic mass from 27 to 124 and is selected from the group consisting of Groups IB, IIB, IIIA, IVB, IVA and VA of the Periodic Table of elements.

29. The method according to claim 28, wherein the Lewis acid has a structure of $M^aX_{3-y}R^a_y$ in case of Si and Ti, and has a structure of $M^aX_{2-y}R^a_y$ in case of Al.

30. An activation method comprising: bringing the catalyst according to claim 1 into contact with an acid wherein the acid is an acid generated in situ from the contact of a molecule of formula RYH with a Lewis acid which at least contains one halogen atom or from a photo-acid generator under conditions such that the acid is able to at least partly cleave a bond between the transition metal and at least one ditopic/multitopic ligand; wherein Y is selected from the group consisting of oxygen, sulphur and selenium, and R is as defined hereinabove.

31. The method according to claim 30, wherein the conditions include:
a molar ratio between the acid and the catalyst of above 0.2 and below 80;
a contact time from 2 seconds to 150 hours and;
a contact temperature from about −100° C. to about +100° C.

32. A process to produce alpha-olefin comprising contacting an unsaturated fatty acid with an alkene and the catalyst according to claim 1 wherein the alpha olefin produced has at least one more carbon atom than the alkene.

33. A process to produce alpha-olefin comprising contacting an unsaturated fatty acid ester and/or an unsaturated fatty acid alkyl ester with an alkene and the catalyst according to claim 1 wherein the alpha olefin produced has at least one more carbon atom than the alkene.

34. A process to produce polymers or thermoset networks comprising a step of combining a mixture A containing a cyclic olefin or a mixture of cyclic olefins and a catalyst of the formula I or II as defined claim 1 and a mixture B containing a cyclic olefin or a mixture of cyclic olefins and an activator wherein the process is a casting process, a reaction-injection molding (RIM) process, a resin transfer molding (RTM) process, a vacuum infusion and vacuum forming process or a reactive rotational molding (RRM) process, wherein the activator is a Lewis acid selected from the group consisting of:

$M^a(I)$ halides, compounds represented by the formula $M^aX_{2-y}R^a_y$ (0≤y≤2);

compounds represented by the formula $M^aX_{3-y}R^a_y$ (0≤y≤3);

compounds represented by the formula $M^aX_{4-y}R^a_y$ (0≤y≤4);

compounds represented by the formula $M^aX_{5-y}R^a_y$ (0≤y≤5);

compounds represented by the formula $M^aX_{6-y}R^a_y$ (0≤y≤6);

wherein $R^a$ represents alkyl, cycloalkyl, alkenyl, cycloalkenyl, substituted alkenyl, heteroalkenyl, heteroatom-containing alkynyl, alkenylene, alkynyl, substituted alkynyl, aryl, substituted aryl, heteroaryl, carboxylate, alkoxy, alkenyloxy, alkynyloxy, aryloxy, alkaryl, aralkyl, alkaryloxy, aralkyloxy, alkoxycarbonyl, alkylamino-, alkylthio-, arylthio, alkylsulfonyl, alkylsulfinyl, dialkylamino, alkylammonium, alkylsilyl or alkoxysilyl, X is an atom of the halogen group and identical or different in the case where more than one halogen atom is present, and $M^a$ is an atom having an atomic mass from 27 to 124 and is selected from the group consisting of Groups IB, IIB, IIIA, IVB, IVA and VA of the Periodic Table of elements.

35. A Group 8 transition metal catalyst having a general structure of formula (VII):

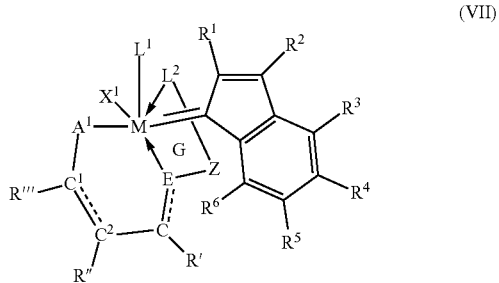

wherein

M is a Group 8 transition metal;

$R^1$, $R^4$, $R^5$, and $R^6$ are hydrogen;

$R^2$ and $R^3$ are identical or different and selected from phenyl, substituted phenyl, heteroatom-containing aryl, hydrocarbyl, substituted hydrocarbyl, or substituted heteroatom-containing hydrocarbyl;

wherein alternatively $R^2$ and $R^3$, including the ring carbon atoms to which they are attached, generate one or more cyclic structures, including aromatic structures;

$X^1$ represents an anionic ligand;

$L^1$ and $L^2$ are identical or different and represent neutral electron donor ligands;

$L^1$ and $X^1$ may be joined to form a multidentate monoanionic group and may form a single ring of up to 30 non-hydrogen atoms or a multinuclear ring system of up to 30 non-hydrogen atoms;

$A^1$ is selected from the group consisting of oxygen, sulphur, selenium, NR'''', PR'''', and POR'''';

E represents a donor atom selected from the group consisting of nitrogen, phosphorus, oxygen, sulphur, and selenium; wherein in case of oxygen, sulphur and selenium, Z-$L^2$ is omitted for double bonded E or Z-$L^2$ remains and C bears R' for a single bonded E; wherein in case of nitrogen, and phosphorus, the bond between C and E is a double bond and Z-$L^2$ remains;

$C^1$ and $C^2$ are carbon atoms linked to each other via a single or double bond wherein in case of a single bond each carbon atom bears an extra substituent $R^{C1}$ and $R^{C2}$;

R', R", R'" and R"" are identical or different and selected from H, hydrocarbyl, substituted hydrocarbyl, heteroatom containing hydrocarbyl, substituted heteroatom-containing hydrocarbyl, or a functional group;

wherein alternatively two directly adjacent radicals from the group of R', R", R'" and R"", including the atoms to which they are attached, generate one or more cyclic structures, including aromatic structures;

$R^{C1}$ and $R^{C2}$ are identical or different and are as defined for R', R", R'" and R"";

$A^1$ and $X^1$ are joined to form a dianionic ligand and form a single ring of up to 30 non-hydrogen atoms or a multinuclear ring system of up to 30 non-hydrogen atoms;

wherein the ring G is a 4-, 5-, 6-, 7-, 8-, 9- or 10-membered ring, and Z is a linking group comprising from one to seven linked vertex atoms selected from the group consisting of C, O, N, P, S and Si with available valences occupied by hydrogen, halogen, hydroxyl, aldehyde, keto, thiol, $CF_3$, nitro, nitroso, cyano, thiocyano, isocyanates, carbodiimide, carbamate, thiocarbamate, dithiocarbamate, amino, amido, imino, ammonium, silyl, sulphonate ($—SO_3^-$), $—OSO_3^-$, $—PO_3^-$, $—OPO_3^-$, acyl, acyloxy, alkyl, cycloalkyl, alkenyl, cycloalkenyl, substituted alkenyl, heteroalkenyl, heteroatom-containing alkynyl, alkenylene, alkynyl, substituted alkynyl, aryl, substituted aryl, heteroaryl, carboxylate, alkoxy, alkenyloxy, alkynyloxy, aryloxy, alkaryl, aralkyl, alkaryloxy, aralkyloxy, alkoxycarbonyl, alkylamino-, alkylthio-, arylthio, alkylsulfonyl, alkylsulfinyl, dialkylamino, alkylammonium, alkylsilyl or alkoxysilyl, where alternatively two directly adjacent vertex atoms from Z generate one or more cyclic structures, including aromatic structures.

36. The catalyst according to claim 35, wherein M is Ru or Os.

37. The catalyst according to claim 35, wherein $L^1$ is selected from phosphine, sulphonated phosphine, phosphate, phosphinite, phosphonite, phosphite, arsine, stibine, ether, amine, amide, sulfoxide, carboxyl, nitrosyl, pyridine, substituted pyridine, pyrazine, thiocarbonyl, thioether, triazole carbene, N-heterocyclic carbene (NHC), substituted NHC, or a cyclic alkyl amino carbene; or wherein $L^1$ represents a phosphine ligand having the formula $P(Q^1)_3$ wherein $Q^1$ are identical or different and are alkyl, cycloalkyl, cyclopentyl, cyclohexyl, neopentyl, aryl, $C_1$-$C_{10}$ alkyl-phosphabicyclononane, $C_3$-$C_{20}$ cycloalkyl phosphabicyclononane, $C_6$-$C_{24}$ aryl or $C_1$-$C_{10}$ -alkyl-phosphinite ligand, a $C_6$-$C_{24}$ aryl or $C_1$-$C_{10}$ alkyl phosphonite ligand, a $C_6$-$C_{24}$ aryl or $C_1$-$C_{10}$ alkyl phosphite-ligand, a $C_6$-$C_{24}$ aryl or $C_1$-$C_{10}$ alkyl arsine ligand, a $C_6$-$C_{24}$aryl or $C_1$-$C_{10}$ alkyl amine ligand, a pyridine ligand, a $C_6$-$C_{24}$ aryl or $C_1$-$C_{10}$ alkyl-sulfoxide ligand, a $C_6$-$C_{24}$-aryl or $C_1$-$C_{10}$ alkyl ether ligand or a $C_6$-$C_{24}$ aryl or $C_1$-$C_{10}$ alkyl amide ligand, or a sulfonated phosphine ligand of formula $P(Q^2)_3$ wherein $Q^2$ represents a mono-or poly-sulfonated $Q^1$-ligand;

or wherein $L^1$ represents a nitrogen-containing ligand selected from pyridine, picolines (α-, (β-, and γ-picoline), lutidines (2,3-, 2,4-, 2,5-, 2,6-, 3,4- and 3,5-lutidine), collidine (2,4,6-trimethylpyridine), trifluoromethylpyridine, phenylpyridine, 4-(dimethylamino) pyridine, chloropyridines (2-, 3- and 4-chloropyridine), bromopyridines (2-, 3- and 4-bromopyridine), nitropyridines (2-, 3- and 4-nitropyridine), bipyridine, picolylimine, gamma-pyran, phenanthroline, pyrimidine, bipyrimide, pyrazine, indole, coumarine, carbazole, pyrazole, pyrrole, imidazole, oxazole, thiazole, dithiazole, isoxazole, isothiazole, quinoline, bisquinoline, isoquinoline, bisisoquinoline, acridine, chromene, phenazine, phenoxazine, phenothiazine, triazine, thianthrene, purine benzimidazole, bisimidazole, bisoxazole pyrrole, imidazole or phenylimidazole; or wherein $L^1$ represents a N-heterocyclic carbene (NHC) having a general structure of formula (IIIa) or (IIIb),

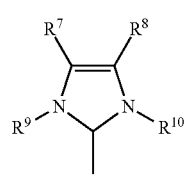

(IIIa)

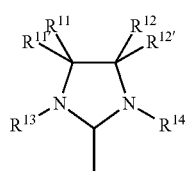

(IIIb)

wherein $R^7$-$R^{14}$, $R^{11'}$, $R^{12'}$ are identical or different and are hydrogen, straight or branched $C_1$-$C_{30}$ alkyl, $C_3$-$C_{20}$ cycloalkyl, $C_2$-$C_{20}$ alkenyl, $C_2$-$C_{20}$ alkynyl, $C_6$-$C_{24}$ aryl, $C_1$-$C_{20}$ carboxylate, $C_1$-$C_{20}$ alkoxy, $C_2$-$C_{20}$ alkenyloxy, $C_2$-$C_{20}$ alkynyloxy, $C_6$-$C_{20}$ aryloxy, $C_2$-$C_{20}$ alkoxycarbonyl, $C_1$-$C_{20}$ alkylthio, $C_6$-$C_{20}$ arylthio, $C_1$-$C_{20}$ alkylsulfonyl, $C_1$-$C_{20}$ alkyl sulfonate, $C_6$-$C_{20}$ aryl sulfonate or $C_1$-$C_{20}$ alkyl sulfinyl, and one or more of the radicals $R^7$-$R^{14}$, $R^{11'}$, $R^{12'}$ may independently of one another be substituted by one or more substituents, straight or branched $C_1$-$C_{10}$ alkyl, $C_3$-$C_8$ cycloalkyl, $C_1$-$C_{10}$ alkoxy or $C_6$-$C_{24}$ aryl; or wherein $L^1$ represents a cyclic alkyl amino carbene (CAAC) having a general structure of Formula (VI):

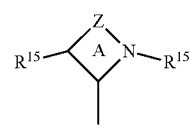

(VI)

wherein the ring A is a 4-, 5-, 6-, or 7-membered ring, and Z is a linking group comprising from one to four linked vertex atoms selected from the group consisting of C, O, N, B, Al, P, S and Si with available valences occupied by hydrogen, oxo or R-substituents, wherein R' is independently selected from the group consisting of $C_1$ to $C_{12}$ hydrocarbyl groups, substituted $C_1$ to $C_{12}$ hydrocarbyl groups, and halides, and each $R^{15}$ is independently a hydrocarbyl group or substituted hydrocarbyl group having 1 to 40 carbon atoms.

38. The catalyst according to claim 37, wherein $Q^1$ is $C_1$-$C_{10}$ alkyl, $C_3$-$C_{20}$ cycloalkyl, or $C_6$-$C_{24}$ aryl.

39. The catalyst according to claim 37, wherein $R^{15}$ is methyl, ethyl, propyl, isobutyl, n-butyl, pentyl, cyclopentyl, hexyl, cyclohexyl, octyl, cyclooctyl, nonyl, decyl, cyclodecyl, dodecyl, cyclododecyl, mesityl, adamantyl, phenyl, benzyl, toluyl, chlorophenyl, phenol, or substituted phenol.

40. The catalyst according to claim 35, wherein $X^1$ is selected from hydrogen, halide, nitrate, pseudohalogen, straight-chain or branched $C_1$-$C_{30}$-alkyl, $C_6$-$C_{24}$ aryl, $C_1$-$C_{20}$ alkylthiol, $C_6$-$C_{24}$ arylthiol, $C_1$-$C_{20}$ alkoxy, $C_6$-$C_{24}$ aryloxy, $C_2$-$C_{24}$ alkoxycarbonyl, $C_6$-$C_{20}$ aryloxycarbonyl, $C_2$-$C_{20}$ acyl, $C_2$-$C_{20}$ acyloxy, $C_3$-$C_{20}$ alkyl diketonate, $C_6$-$C_{24}$ aryl diketonate, $C_1$-$C_{20}$ carboxylate, $C_1$-$C_{20}$ alkylsulfonato, $C_5$-$C_{20}$ arylsulfonato, $C_1$-$C_{20}$ alkylsulfanyl, $C_5$-$C_{20}$ arylsulfanyl, $C_1$-$C_{20}$ alkylsulfinyl, or $C_5$-$C_{20}$ arylsulfinyl, any of which, with the exception of hydrogen and halide, are further substituted with one or more groups selected from halide, $C_1$-$C_6$ alkyl, $C_1$-$C_6$ alkoxy, and $C_5$-$C_{20}$ aryl; or wherein $X^1$ and $A^1$ are joined to form a dianionic group and form a single ring of up to 30 non-hydrogen atoms or a multinuclear ring system of up to 30 non-hydrogen atoms; or wherein $L^1$ and $X^1$ are joined to form a multidentate monoanionic group and form a single ring of up to 30 non-hydrogen atoms or a multinuclear ring system of up to 30 non-hydrogen atoms; or wherein, $X^1$ denotes fluoride, chloride, bromide iodide, nitrate, benzoate, $C_1$-$C_5$ carboxylate, $C_1$-$C_5$ alkyl, phenoxy, $C_1$-$C_5$ alkoxy, $C_1$-$C_5$ alkylthiolate, $C_6$-$C_{24}$ arylthiolate, $C_6$-$C_{24}$ aryl or $C_1$-$C_5$ alkyl sulfonate; or wherein $X^1$ is chloride, nitrate, $CF_3COO$, $CH_3COO$, $CFH_2COO$, $(CH_3)_3CO$, $(CF_3)_2(CH_3)CO$, $(CF_3)(CH_3)_2 CO$, PhO (phenoxy), $C_6F_5O$ (pentafluorophenoxy), MeO (methoxy), EtO (ethoxy), p-$CH_3$—$C_6H_4$—$SO_3$ (tosylate), $CH_3SO_3$ (mesylate) or $CF_3SO_3$ (trifluoromethanesulfonate).

41. A method for making a Group 8 transition metal catalyst having a general structure of formula (VII) according to claim 35, comprising contacting a precursor compound of the formula $(X^1X^2ML_3)$ or $(X^1X^2ML_4)$ with an acetylenic compound, and at least one ditopic or multitopic ligand;

wherein for the precursor compound,

M is a Group 8 transition metal;

$X^1$ and $X^2$ are identical or different and represent an anionic ligand; and $L_3$ and $L_4$ represent a neutral electron donor ligand.

42. A process to produce polymers or thermoset networks comprising a step of combining a mixture A containing a cyclic olefin or a mixture of cyclic olefins and a catalyst of the formula VII as defined claim 35 and a mixture B containing a cyclic olefin or a mixture of cyclic olefins and an activator wherein the process is a casting process, a reaction-injection molding (RIM) process, a resin transfer molding (RTM) process, a vacuum infusion and vacuum forming process or a reactive rotational molding (RRM) process, wherein the activator is a Lewis acid selected from the group consisting of:

$M^a$(I) halides, compounds represented by the formula $M^a X_{2-y} R^a_y$ ($0 \leq y \leq 2$);

compounds represented by the formula $M^a X_{3-y} R^a_y$ ($0 \leq y \leq 3$);

compounds represented by the formula $M^a X_{4-y} R^a_y$ ($0 \leq y \leq 4$);

compounds represented by the formula $M^a X_{5-y} R^a_y$ ($0 \leq y \leq 5$);

compounds represented by the formula $M^a X_{6-y} R^a_y$ ($0 \leq y \leq 6$);

wherein $R^a$ represents alkyl, cycloalkyl, alkenyl, cycloalkenyl, substituted alkenyl, heteroalkenyl, heteroatom-containing alkynyl, alkenylene, alkynyl, substituted alkynyl, aryl, substituted aryl, heteroaryl, carboxylate, alkoxy, alkenyloxy, alkynyloxy, aryloxy, alkaryl, aralkyl, alkaryloxy, aralkyloxy, alkoxycarbonyl, alkylamino-, alkylthio-, arylthio, alkylsulfonyl, alkylsulfinyl, dialkylamino, alkylammonium, alkylsilyl or alkoxysilyl, X is an atom of the halogen group and identical or different in the case where more than one halogen atom is present, and $M^a$ is an atom having an atomic mass from 27 to 124 and is selected from the group consisting of Groups IB, IIB, IIIA, IVB, IVA and VA of the Periodic Table of elements.

* * * * *